United States Patent
Thunuguntla et al.

(10) Patent No.: US 11,028,054 B2
(45) Date of Patent: Jun. 8, 2021

(54) 1, 4, 6-TRISUBSTITUTED-2-ALKYL-1H-BENZO[D]IMIDAZOLE DERIVATIVES AS DIHYDROOROTATE OXYGENASE INHIBITORS

(71) Applicant: Merck Patent GmbH, Darmstadt (DE)

(72) Inventors: Siva Sanjeeva Rao Thunuguntla, Hyderabad (IN); Subramanya Hosahalli, Bangalore (IN); Sunil Kumar Panigrahi, Boudh (IN); Matthias Schwarz, Gland (CH); Michael Arit, Alsbach (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/488,151

(22) PCT Filed: Feb. 23, 2018

(86) PCT No.: PCT/EP2018/054602
§ 371 (c)(1),
(2) Date: Aug. 22, 2019

(87) PCT Pub. No.: WO2018/154088
PCT Pub. Date: Aug. 30, 2018

(65) Prior Publication Data
US 2020/0140395 A1 May 7, 2020

(30) Foreign Application Priority Data

Feb. 24, 2017 (IN) .............................. 201741006586

(51) Int. Cl.
| | |
|---|---|
| C07D 235/08 | (2006.01) |
| C07D 401/10 | (2006.01) |
| C07D 403/10 | (2006.01) |
| C07D 413/10 | (2006.01) |
| C07D 235/24 | (2006.01) |
| C07D 417/10 | (2006.01) |

(52) U.S. Cl.
CPC ......... *C07D 235/24* (2013.01); *C07D 235/08* (2013.01); *C07D 401/10* (2013.01); *C07D 403/10* (2013.01); *C07D 413/10* (2013.01); *C07D 417/10* (2013.01)

(58) Field of Classification Search
CPC .. C07D 235/08; C07D 401/10; C07D 403/10; C07D 413/10
See application file for complete search history.

(56) References Cited

FOREIGN PATENT DOCUMENTS

| | | |
|---|---|---|
| WO | 2010/115736 A2 | 10/2010 |
| WO | 2014/128669 A2 | 8/2014 |

OTHER PUBLICATIONS

Golub et al., Science, vol. 286, Oct. 15, 1999, pp. 531-537. (Year: 1999).*
Batt, Inhibitors of dihydroorotate dehydrogenase. Expert Opinion on Therapeutic Patents. 1999;9(1):41-54.
Walse et al., The structures of human dihydroorotate dehydrogenase with and without inhibitor reveal conformational flexibility in the inhibitor and substrate binding sites. Biochemistry. 2008;47(34):8929-8936.
International Search Report and Written Opinion for Application No. PCT/EP2018/054602, dated Jul. 10, 2018, 8 pages.

* cited by examiner

*Primary Examiner* — Laura L Stockton
(74) *Attorney, Agent, or Firm* — McCarter & English, LLP; Steven G. Davis; Michael J. DeGrazia

(57) ABSTRACT

The present invention provides 1, 4, 6-trisubstituted-2-alkyl-1H-benzo[d]imidazole derivatives as dihydroorotate oxygenase inhibitor compounds of formula (I), which may be therapeutically useful as DHODH inhibitors, in which $R_1$ to $R_3$ and 'm' have the meanings given in the specification, and pharmaceutically acceptable salts or stereoisomer thereof that are useful in the treatment and prevention in diseases or disorder, in particular their use in diseases or disorder where there is an advantage in inhibiting DHODH. The present invention also provides methods for synthesizing 1, 4, 6-trisubstituted-2-alkyl-1H-benzo[d]imidazole derivatives of formula (I). The present invention also provides pharmaceutical formulations comprising at least one of the DHODH inhibitor compound of formula (I) together with a pharmaceutically acceptable carrier, diluent or excipient.

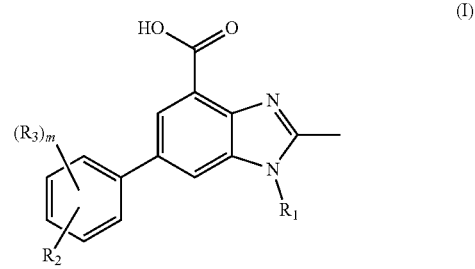

16 Claims, No Drawings

1, 4, 6-TRISUBSTITUTED-2-ALKYL-1H-BENZO[D]IMIDAZOLE DERIVATIVES AS DIHYDROOROTATE OXYGENASE INHIBITORS

CROSS-REFERENCE TO RELATED APPLICATIONS

This application is a 35 U.S.C. § 371 national stage filing of International Application No. PCT/EP2018/054602, filed on Feb. 23, 2018 which in turn claims priority to Indian Provisional Application No. 201741006586, filed Feb. 24, 2017. The entire contents of each of the foregoing applications are incorporated herein by reference.

FIELD OF INVENTION

The present invention relates to novel 1, 4, 6-trisubstituted-2-alkyl-1H-benzo[d]imidazole derivatives of formula (I) which are inhibitors of dihydroorotate dehydrogenase.

The invention also relates to the process for the preparation of the compounds of the present invention thereof, pharmaceutical compositions comprising them, and their use for the treatment and prevention of disease or disorder, in particular their use in diseases or disorders associated, where there is an advantage in inhibiting DHODH.

BACKGROUND OF THE INVENTION

DHODH is a protein that catalyzes one of the steps in denovo pyrimidine nucleotide biosynthetic pathway. (Greene et al. Biochem Pharmacol 1995, 50:861-7; Davis J. P et al. FASEB J 1996, 10(6): Abst C23). It catalyzes the only oxidation/reduction reaction in that pathway, which is the step of converting DHO (dihydroorotate) to orotate with the aid of flavin cofactor and an electron acceptor. Inhibitors of dihydroorotate dehydrogenase have been found to possess wider applications as chemotherapeutic agents. (Kensler et al. 1989 in: Design of Enzyme Inhibitors as Drugs; Sandler, M., and Smith, H. J. Eds., pp 379-401 Oxford Univ Press, Oxford England; Cody et al. Am. J. Clin. Oncol. 16, 526-528 (1993)).

As an example for DHODH inhibitors, the quinoline derivative Brequinar (6-Fluoro-2-(2'-fluoro[1,1'-biphenyl]-4-yl)-3-methyl-4-quinolinecarboxylic Acid) exhibits an anticancer activity towards L1210 murine leukemia. (Andreson L W. Et al. Cancer Commun. 1989; 1(6):381-7; Chen S F. et al. Cancer Res. 1986 October; 46(10):5014-9). It has also been shown that Brequinar potentiates 5-fluorouracil antitumor activity in a murine model colon 38 tumor by tissue-specific modulation of uridine nucleotide pools. (G Pizzorno et al. Cancer Res. 1992 Apr. 1; 52:1660-5).

DHODH inhibitors may also be useful in the treatment of viral mediated diseases (see U.S. Pat. No. 6,841,561). Furthermore, inhibition of DHODH is known to be among promising target for treating transplant rejection, rheumatoid arthritis, psoriasis as well as autoimmune diseases (Kovarik, J. M. et al. Expert Opin. Emerg. Drugs 2003, 8, 47; Allison, A. C. Transplantation Proc. (1993) 25(3) Suppl. 2, 8-18); Makowka, L., Immunolog Rev. (1993) 136, 51-70; Davis J. P et al. Biochemistry 1996, 35:1270-3).

Leflunomide, a well-known DHODH inhibitor is a synthetic drug currently marketed, a low-molecular weight drug of the isoxazole class (see EP0527736, JP 1993506425, JP 1999322700, JP 1999343285, U.S. Pat. Nos. 5,494,911, 5,532,259, WO19991017748) and used in the treatment of Rheumatoid arthritis and is also under evaluation for use in the treatment of inflammatory bowel disease and chronic allograft rejection.

In vivo, Leflunomide is quickly transformed in its active metabolite Teriflunomide that exerts its anti-inflammatory, antiproliferative and immunosuppressive effects via mechanisms that are not completely understood. Teriflunomide is not only a potential inhibitor of protein tyrosine kinase in vivo but a 100-1,000-fold greater inhibitor of DHODH (Davis J. P et al. FASEB J 1996, 10(6): Abst C23; Davis J. P et al. Biochemistry 1996, 35:1270-3).

With the rise in number of patients affected by autoimmune and related diseases, there is unmet need for new drugs that can treat such diseases more effectively. There is still a crucial need for immunosuppressive agents, that are further useful in a wide variety of autoimmune and chronic inflammatory diseases, including systemic lupus erythematosus, chronic rheumatoid arthritis, multiple sclerosis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. They may also be useful as part of chemotherapeutic regimens for the treatment of cancers, lymphomas and leukaemia's, alone or in combination with antitumoral compounds well known by the one skilled in the art.

SUMMARY OF INVENTION

The present invention relates to 1, 4, 6-trisubstituted-2-alkyl-1H-benzo[d]imidazole derivatives as dihydroorotate-oxygenase inhibitors (also known as Dihydroorotate dehydrogenase inhibitors). These derivatives may be useful as medicament in treatment of autoimmune and inflammatory disorders such as multiple sclerosis, rheumatoid arthritis and diseases like cancer.

In particular, the present invention relates to compounds of formula (I):

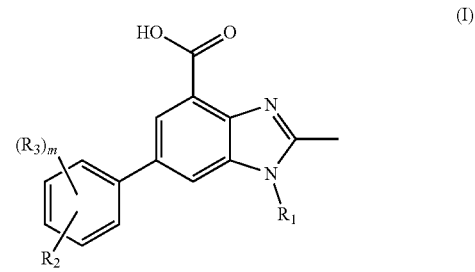

or a pharmaceutically acceptable salt, solvate, tautomer, hydrate, stereoisomer and mixture of isomers, or N-oxide thereof;

wherein;

$R_1$ is hydrogen or linear or branched $C_1$-$C_6$ alkyl;

$R_2$ is an optionally substituted Cb, an optionally substituted Het or —O—$(CH_2)_p$Cb'; wherein the optional substituent, at each occurrence, is independently selected from one or more occurrences of $R_4$;

$R_3$ is hydrogen, halogen, linear or branched $C_1$-$C_6$ alkyl or —$OR_5$;

$R_4$ is independently selected from hydrogen, halogen, linear or branched $C_1$-$C_6$ alkyl, —$(CH_2)_pO(CH_2)_qR_7$, —$(CH_2)_pS(=O)_xR_5$, —$C(R_5)=NOR_5$, —$(CH_2)_p$Het' and —$(CH_2)_pNR_5$ $(CH_2)_qR_6$;

$R_5$ is independently selected from hydrogen and linear or branched $C_1$-$C_6$ alkyl;

$R_6$ is independently selected from hydrogen, linear or branched $C_1$-$C_6$ alkyl, —(CO)Het, Cb', Het', —$CF_3$, —C≡$CR_5$, —$N(R_5)_2$, —$S(=O)_xR_5$ and —$OR_5$;

$R_7$ is independently selected from hydrogen, linear or branched $C_1$-$C_6$ alkyl, Cb', Het', —$CF_3$, —C≡$CR_5$, —$N(R_5)_2$ or —$S(=O)_xR_5$;

Cb and Cb' independently represents a monocyclic, a fused or non-fused bicyclic, saturated, unsaturated or aromatic carbocyclic ring system having 3 to 14 carbon atoms; wherein the Cb and Cb' are optionally substituted with 'n' occurrences of $R_7$;

Het and Het' independently represents a 3- to 14-membered, monocyclic, a fused or non-fused bicyclic, saturated, unsaturated or aromatic heterocyclic ring system having at least 1 to 4 heteroatom or heterogroup selected from N, O, S, CO, NH, SO and $SO_2$; wherein the Het and Het' are optionally substituted with 'n' occurrences of $R_8$;

$R_8$, at each occurrence, is independently selected from halogen, hydroxy, oxo and linear or branched $C_1$-$C_6$ alkyl;

'm' is 0 to 4; 'n', 'p' and 'q' independently represents 0 to 3; and 'x' is 0 to 2.

In yet another aspect of the present invention, it relates to process for preparation of novel 1, 4, 6 trisubstituted-2-alkyl-1H-benzo[d]imidazole derivatives of formula (I).

In a further aspect of the present invention, it relates to the pharmaceutical composition comprising 1, 4, 6-trisubstituted-2-alkyl-1H-benzo[d]imidazole derivatives of formula (I) and processes for preparing thereof.

In yet further another aspect of the present invention, the invention relates to the use of compounds of formula (I) and pharmaceutically acceptable derivatives, solvates, tautomers, salts and stereoisomers thereof, including mixtures thereof in all ratios as a medicament, by inhibiting dihydroorotate oxygenase enzyme activity in treating disorder like multiple sclerosis and other diseases such as inflammatory disorders, rheumatoid arthritis and cancer.

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

DETAILED DESCRIPTION OF THE INVENTION

The singular forms "a", "an" and "the" encompass plural references unless the context clearly indicates otherwise.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as the event or circumstance where the alkyl is not substituted.

The term "optionally substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

"Alkyl" or "linear or branched $C_1$-$C_6$ alkyl" refers to a hydrocarbon chain that may be a linear or branched chain, containing the indicated number of carbon atoms, for example, a $C_1$-$C_6$ alkyl group may have from 1 to 6 (inclusive) carbon atoms in it. Examples of $C_1$-$C_4$ and $C_1$-$C_6$ alkyl groups include, but are not limited to, methyl, ethyl, propyl, butyl, pentyl, hexyl, isopropyl, isobutyl, sec-butyl, tert-butyl, isopentyl, neopentyl, and isohexyl. An alkyl group can be unsubstituted or substituted with one or more suitable groups.

"Aryl" or "aromatic carbocyclic ring" refers to an optionally substituted monocyclic, bicyclic or polycyclic aromatic carbocyclic ring system of about 6 to 14 carbon atoms. Examples of a $C_6$-$C_{14}$ aryl group include, but are not limited to phenyl, naphthyl, biphenyl, anthryl, tetrahydronaphthyl, fluorenyl, indanyl, biphenylenyl, and acenaphthyl. Aryl group which can be unsubstituted or substituted with one or more suitable groups.

"Cb and Cb'" refers to a monocyclic, a fused or non-fused bicyclic, saturated, unsaturated or aromatic carbocyclic ring system having 3 to 14 carbon atoms. Examples of carbocyclic ring group include, but are not limited to Aryl and cycloalkyl. Cb group which can be unsubstituted or substituted with one or more suitable groups.

"Cycloalkyl" refers to a non-aromatic, saturated or unsaturated, monocyclic, bicyclic or polycyclic hydrocarbon ring system. Representative examples of a cycloalkyl include, but are not limited to, cyclopropyl, cyclopentyl, cycloheptyl, cyclooctyl, decahydronaphthalen-1-yl, octahydro-1H-inden-2-yl and decahydro-1H-benzo[7] annulen-2-yl. A cycloalkyl can be unsubstituted or substituted with one or more suitable groups.

"Haloalkyl" refers to an alkyl group, as defined above, wherein one or more of the alkyl group's hydrogen atoms has been replaced with —F, —Cl, —Br, or —I. Examples of a haloalkyl group include, but are not limited to, —$CH_2F$, —$CCl_3$, —$CF_3$, —$CH_2CF_3$, —$CH_2CH(Br)CH_3$, —$CH_2CH$ (Cl)CH$_2$CH$_3$, —CH(F)CH$_2$CH$_3$ and —C(CH$_3$)$_2$(CH$_2$Cl). A haloalkyl group can be unsubstituted or substituted with one or more suitable groups;

"Halogen" or "halo" includes fluorine, chlorine, bromine or iodine.

"Het and Het'" refers to a monocyclic, a fused or non-fused bicyclic, saturated, unsaturated or aromatic heterocyclic ring system of 3 to 14 member having at least 1 to 4 heteroatom or heterogroup selected from N, O, S atoms and/or a group CO, SO or SO$_2$, Examples of heterocyclic ring group include, but are not limited to heteroaryl and heterocycloalkyl. Het group which can be unsubstituted or substituted with one or more suitable groups. Exemplary Het groups include azitidinyl, pyrrolidinyl, pyrrolidine-2-one, piperdinyl, 1-methyl piperdinyl, piperazinyl, morpholinyl, thiomorpholine 1,1-dioxide, thiomorpholinyl, thiazolidinyl, 4,5-dimethyloxazolyl, 1,3-dioxolanyl, 1,4-dioxanyl and the like.

"Heterocycloalkyl" refers to a non-aromatic saturated or unsaturated monocyclic or polycyclic ring system of 3 to 10 member having at least one heteroatom or heterogroup selected from O, N, S, SO or —SO$_2$. Additionally, each of any two hydrogen atoms on the same carbon atom of the heterocyclyl ring can be replaced by an oxygen atom to form an oxo (=O) substituent. Exemplary heterocyclyl groups include azitidinyl, pyrrolidinyl, piperdinyl, piperazinyl, morpholinyl, thiomorpholinyl, thiazolidinyl, 1,3-dioxolanyl, 1,4-dioxanyl and the like. A heterocyclyl group can be unsubstituted or substituted with one or more suitable groups;

"Heteroaryl" or "aromatic heterocyclic ring" refers to a monocyclic, bicyclic, or polycyclic aromatic ring system containing at least one heteroatom selected from oxygen, sulfur or nitrogen. Examples of C$_1$-C$_{10}$ heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic C$_1$-C$_9$heteroaryl groups include those where a phenyl, pyridine, pyrimidine or pyridazine ring is fused to a 5 or 6-membered monocyclic heterocyclyl, heteroaryl ring having one or two nitrogen atoms in the ring, one nitrogen atom together with either one oxygen or one sulfur atom in the ring, or one O or S ring atom. A heteroaryl group can be unsubstituted or substituted with one or more suitable groups.

"Heteroatom" refers to a sulfur, nitrogen, or oxygen atom.

"Hydroxy" refers to —OH group.

"3-14-membered ring containing 0-3 heteroatoms" refers to a monocyclic or bicyclic aromatic or non-aromatic cyclic rings in which 1-4 of the ring carbon atoms have been independently replaced with a N, O or S atom. Representative examples of a 3- to 8-membered ring include, but are not limited to morpholine, pyrrole, cyclobytyl, phenyl, pyridine, pyridinone, tetrahydroisoquinoline.

As used herein, the term 'compound(s)' comprises the compounds disclosed in the present invention. Preferably, the term 'compound(s)' comprises the compounds of formula (I).

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "therapeutically effective amount" refers to that amount of the compound being administered sufficient to prevent development of or alleviate to some extent one or more of the symptoms of the condition or disorder being treated.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

"Pharmaceutically acceptable salt" refers to the salts of the compounds, that is pharmaceutically acceptable and that possesses the desired pharmacological activity of the parent compound. Pharmaceutically acceptable salts of the compounds of this invention include those derived from suitable inorganic and organic acids and bases. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methane sulfonic acid, ethane sulfonic acid, 1,2-ethane-disulfonic acid, 2-hydroxyethanesulfonic acid, benzene sulfonic acid, 4-chlorobenzenesulfonic acid, 2-naphthalenesulfonic acid, 4-toluenesulfonic acid, camphor sulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxyl naphthoic acid, salicylic acid, stearic acid, muconic acid, and the like.

The term "stereoisomers" refers to any enantiomers, diastereoisomers, or geometrical isomers of the compounds of formula (I), (IA) and (IB); wherever they are chiral or when they bear one or more double bonds. When the compounds of the formula (I), (IA) and (IB), and related formulae are chiral, they can exist in racemic or in optically active form. It should be understood that the invention encompasses all stereochemical isomeric forms, including diastereomeric, enantiomeric and epimeric forms, as well as d-isomers and l-isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E) and zusammen (Z) isomers as well as the appropriate mixtures thereof.

The present invention provides 1, 4, 6-trisubstituted-2-alkyl-1H-benzo[d]imidazole derivatives of formula (I) useful as dihydroorotateoxygenase inhibitors.

The present invention further provides pharmaceutical compositions comprising the said 1, 4, 6-trisubstituted-2-alkyl-1H-benzo[d]imidazole derivatives as therapeutic agents.

In certain embodiments, the present invention provides compounds of formula (I):

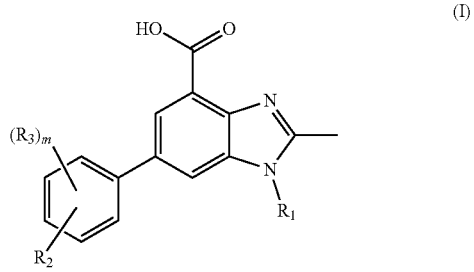

(I)

or a pharmaceutically acceptable salt, solvate, tautomer, hydrate, stereoisomer and mixture of isomers, or N-oxide thereof;
wherein;
$R_1$ is hydrogen or linear or branched $C_1$-$C_6$ alkyl;
$R_2$ is an optionally substituted Cb, an optionally substituted Het or —O—$(CH_2)_p$Cb'; wherein the optional substituent, at each occurrence, is independently selected from one or more occurrences of $R_4$;
$R_3$ is hydrogen, halogen, linear or branched $C_1$-$C_6$ alkyl or —$OR_5$;
$R_4$ is independently selected from hydrogen, halogen, linear or branched $C_1$-$C_6$ alkyl, —$(CH_2)_pO(CH_2)_qR_7$, —$(CH_2)_pS(=O)_xR_5$, —$C(R_5)=NOR_5$, —$(CH_2)_p$Het' and —$(CH_2)_pNR_5(CH_2)_qR_6$;
$R_5$ is independently selected from hydrogen and linear or branched $C_1$-$C_6$ alkyl;
$R_6$ is independently selected from hydrogen, linear or branched $C_1$-$C_6$ alkyl, —(CO)Het, Cb', Het', —$CF_3$, —C≡$CR_5$, —$N(R_5)_2$, —$S(=O)_xR_5$ and —$OR_5$;
$R_7$ is independently selected from hydrogen, linear or branched $C_1$-$C_6$ alkyl, Cb', Het', —$CF_3$, —C≡$CR_5$, —$N(R_5)_2$ or —$S(=O)_xR_5$;
Cb and Cb' independently represents a monocyclic, a fused or non-fused bicyclic, saturated, unsaturated or aromatic carbocyclic ring system having 3 to 14 carbon atoms; wherein the Cb and Cb' are optionally substituted with 'n' occurrences of $R_7$;
Het and Het' independently represents a 3- to 14-membered, monocyclic, a fused or non-fused bicyclic, saturated, unsaturated or aromatic heterocyclic ring system having at least 1 to 4 heteroatom or heterogroup selected from N, O, S, CO, NH, SO and $SO_2$; wherein the Het and Het' are optionally substituted with 'n' occurrences of $R_8$;

$R_8$, at each occurrence, is independently selected from halogen, hydroxy, oxo and linear or branched $C_1$-$C_6$ alkyl;
'm' is 0 to 4; 'n', 'p' and 'q' independently represents 0 to 3; and 'x' is 0 to 2.

The embodiment below are illustrative of the present invention and are not intended to limit the claims to the specific embodiments exemplified.

According to yet another embodiment of the present invention, the compound of formula (I) is a compound of formula (IA):

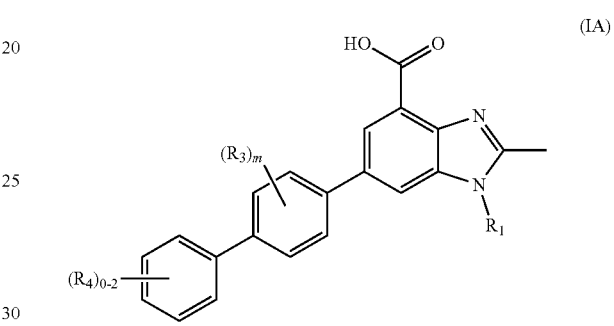

(IA)

or a pharmaceutically acceptable salt or a stereoisomer thereof; wherein $R_1$, $R_3$, $R_4$ and 'm' are same as defined in formula (I).

According to yet another embodiment of the present invention, the compound of formula (I) is a compound of formula (IB):

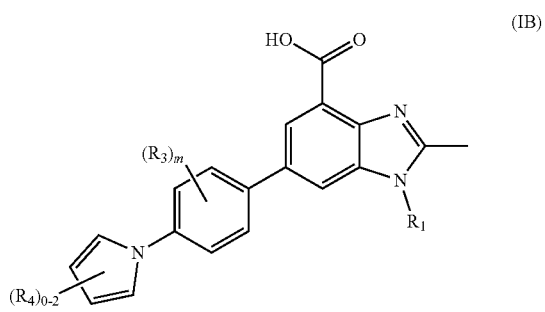

(IB)

or a pharmaceutically acceptable salt or a stereoisomer thereof; wherein $R_1$, $R_3$, $R_4$ and 'm' are same as defined in formula (I).

In particular embodiment, wherein $R_1$ group is hydrogen and the remaining groups are same as defined in formula (I).

1, 4, 6-trisubstituted-2-alkyl-1H-benzo[d]imidazole derivatives of formula (I) of the present invention wherein $R_1$ is hydrogen, also includes all tautomeric forms. Preferred tautomeric forms are represented by the following formulae (Ia and Ia').

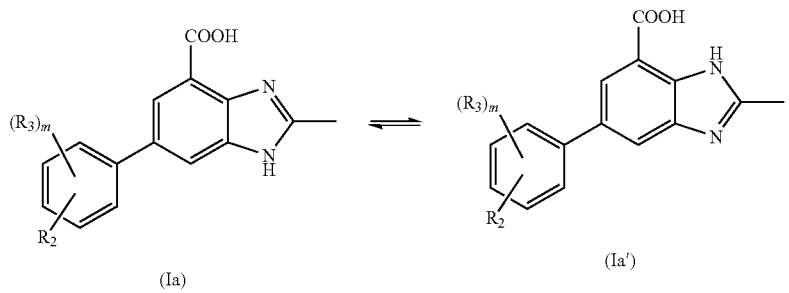

or a pharmaceutically acceptable salt or a stereoisomer thereof; wherein $R_2$, $R_3$ and 'm' are as same as defined in formula (I).

In certain embodiments, $R_2$ represents an optionally substituted Cb and the remaining groups are same as defined in formula (I).

In certain embodiments, wherein $R_2$ represents an optionally substituted Het and the remaining groups are same as defined in formula (I).

In another particular embodiment, wherein $R_2$ group represents an —O—$(CH_2)_p$Cb and the remaining groups are same as defined in formula (I).

In another embodiment, Cb represents phenyl optionally substituted with one or more occurrences of $R_4$ and the remaining groups are same as defined in formula (I).

In another embodiment, the above said Het represents pyrrole, pyrazole, pyridyl, or isoxazole; wherein each said groups are optionally substituted with one or more occurrences of $R_4$ and the remaining groups are same as defined in formula (I).

In another embodiment, $R_4$ represents hydrogen, halogen, hydroxy, linear or branched $C_1$-$C_6$ alkyl, —$(CH_2)_p$Het', —$(CH_2)_p NR_5 (CH_2)_q R_6$, —$(CH_2)_p O (CH_2)_q R_7$, wherein $R_5$ represents hydrogen; and $R_6$ and $R_7$ independently represents Cb' and Het'.

In another embodiment, the above said Cb' represents phenyl, cyclopropyl and Het' represents piperidine, morpholine, 3-fluoro pyrrolidine, thiomorpholine 1,1-dioxide and the remaining groups are same as defined in formula (I).

In another embodiment of the present invention, it provides the process for preparation of 1, 4, 6-trisubstituted-2-alkyl-1H-benzo[d]imidazole derivatives of formula (I).

The procedure for the compounds of formula (I) is detailed herein below in the specification stepwise including the general synthesis of various intermediates involved in process of manufacture of the compounds according to the present invention.

In yet another particular embodiment of the present invention, the compound of formula (I) is:

| Example No | IUPAC names |
|---|---|
| 1. | 6-([1,1'-biphenyl]-4-yl)-2-methyl-1H-benzo[d]imidazole-4-carboxylic acid; |
| 2. | 6-(3',5'-difluoro-[1,1'-biphenyl]-4-yl)-2-methyl-1H-benzo[d]imidazole-4-carboxylic acid; |
| 3. | 6-(3',4'-difluoro-[1,1'-biphenyl]-4-yl)-2-methyl-1H-benzo[d]imidazole-4-carboxylic acid; |
| 4. | 6-(2',3'-difluoro-[1,1'-biphenyl]-4-yl)-2-methyl-1H-benzo[d]imidazole-4-carboxylic acid; |
| 5. | 6-(2'-fluoro-[1,1'-biphenyl]-4-yl)-2-methyl-1H-benzo[d]imidazole-4-carboxylic acid; |
| 6. | 6-(4'-fluoro-[1,1'-biphenyl]-4-yl)-2-methyl-1H-benzo[d]imidazole-4-carboxylic acid; |
| 7. | 2-methyl-6-(4-(pyridin-3-yl)phenyl)-1H-benzo[d]imidazole-4-carboxylic acid; |
| 8. | 6-(3'-fluoro-[1,1'-biphenyl]-4-yl)-2-methyl-1H-benzo[d]imidazole-4-carboxylic acid.; |
| 9. | 2-methyl-6-(4-(pyridin-4-yl)phenyl)-1H-benzo[d]imidazole-4-carboxylic acid; |
| 10. | 6-(3'-methoxy-[1,1'-biphenyl]-4-yl)-2-methyl-1H-benzo[d]imidazole-4-carboxylic acid; |
| 11. | 2-methyl-6-(3'-(trifluoromethoxy)-[1,1'-biphenyl]-4-yl)-1H-benzo[d]imidazole-4-carboxylic acid; |
| 12. | 6-(2',5'-difluoro-[1,1'-biphenyl]-4-yl)-2-methyl-1H-benzo[d]imidazole-4-carboxylic acid; |
| 13. | 2-methyl-6-(4'-(trifluoromethoxy)-[1,1'-biphenyl]-4-yl)-1H-benzo[d]imidazole-4-carboxylic acid; |
| 14. | 6-(4'-methoxy-[1,1'-biphenyl]-4-yl)-2-methyl-1H-benzo[d]imidazole-4-carboxylic acid; |
| 15. | 6-(3'-(benzyloxy)-[1,1'-biphenyl]-4-yl)-2-methyl-1H-benzo[d]imidazole-4-carboxylic acid; |
| 16. | 6-(3'-hydroxy-[1,1'-biphenyl]-4-yl)-2-methyl-1H-benzo[d]imidazole-4-carboxylic acid; |
| 17. | 6-(2'-(benzyloxy)-[1,1'-biphenyl]-4-yl)-2-methyl-1H-benzo[d]imidazole-4-carboxylic acid; |
| 18. | 6-(2'-methoxy-[1,1'-biphenyl]-4-yl)-2-methyl-1H-benzo[d]imidazole-4-carboxylic acid; |
| 19. | 6-(4'-(benzyloxy)-[1,1'-biphenyl]-4-yl)-2-methyl-1H-benzo[d]imidazole-4-carboxylic acid; |
| 20. | 6-(4'-hydroxy-[1,1'-biphenyl]-4-yl)-2-methyl-1H-benzo[d]imidazole-4-carboxylic acid; |
| 21. | 6-(2'-fluoro-3'-methoxy-[1,1'-biphenyl]-4-yl)-2-methyl-1H-benzo[d]imidazole-4-carboxylic acid; |
| 22. | 6-(3'-(benzyloxy)-5'-fluoro-[1,1'-biphenyl]-4-yl)-2-methyl-1H-benzo[d]imidazole-4-carboxylic acid; |
| 23. | 6-(2'-hydroxy-[1,1'-biphenyl]-4-yl)-2-methyl-1H-benzo[d]imidazole-4-carboxylic acid; |

| Example No | IUPAC names |
|---|---|
| 24. | 2-methyl-6-(3'-methyl-[1,1'-biphenyl]-4-yl)-1H-benzo[d]imidazole-4-carboxylic acid; |
| 25. | 2-methyl-6-(2'-methyl-[1,1'-biphenyl]-4-yl)-1H-benzo[d]imidazole-4-carboxylic acid; |
| 26. | 2-methyl-6-(4'-(piperidin-1-ylmethyl)-[1,1'-biphenyl]-4-yl)-1H-benzo[d]imidazole-4-carboxylic acid.2,2,2-trifluoroacetic acid; |
| 27. | 6-(4'-((isopropylamino)methyl)-[1,1'-biphenyl]-4-yl)-2-methyl-1H-benzo[d]imidazole-4-carboxylic acid.2,2,2-trifluoroacetic acid; |
| 28. | 2-methyl-6-(4'-(pyrrolidin-1-ylmethyl)-[1,1'-biphenyl]-4-yl)-1H-benzo[d]imidazole-4-carboxylic acid.2,2,2-trifluoroacetic acid; |
| 29. | 2-methyl-6-(4'-(thiomorpholinomethyl)-[1,1'-biphenyl]-4-yl)-1H-benzo[d]imidazole-4-carboxylic acid.2,2,2-trifluoroacetic acid; |
| 30. | 6-(4'-((3,3-difluoropiperidin-1-yl)methyl)-[1,1'-biphenyl]-4-yl)-2-methyl-1H-benzo[d]imidazole-4-carboxylic acid.2,2,2-trifluoroacetic acid; |
| 31. | 2-methyl-6-(3'-(piperidin-1-ylmethyl)-[1,1'-biphenyl]-4-yl)-1H-benzo[d]imidazole-4-carboxylic acid.2,2,2-trifluoroacetic acid; |
| 32. | 2-methyl-6-(3'-(pyrrolidin-1-ylmethyl)-[1,1'-biphenyl]-4-yl)-1H-benzo[d]imidazole-4-carboxylic acid.2,2,2-trifluoroacetic acid; |
| 33. | 2-methyl-6-(3'-(thiomorpholinomethyl)-[1,1'-biphenyl]-4-yl)-1H-benzo[d]imidazole-4-carboxylic acid; |
| 34. | 6-(3'-((isopropylamino)methyl)-[1,1'-biphenyl]-4-yl)-2-methyl-1H-benzo[d]imidazole-4-carboxylic acid.2,2,2-trifluoroacetic acid; |
| 35. | 2-methyl-6-(3'-(morpholinomethyl)-[1,1'-biphenyl]-4-yl)-1H-benzo[d]imidazole-4-carboxylic acid.2,2,2-trifluoroacetic acid; |
| 36. | 6-(3'-((1,1-dioxidothiomorpholino)methyl)-[1,1'-biphenyl]-4-yl)-2-methyl-1H-benzo[d]imidazole-4-carboxylic acid.2,2,2-trifluoroacetic acid; |
| 37. | 6-(3'-((3,3-difluoropiperidin-1-yl)methyl)-[1,1'-biphenyl]-4-yl)-2-methyl-1H-benzo[d]imidazole-4-carboxylic acid.2,2,2-trifluoroacetic acid; |
| 38. | 6-(3'-((dipropylamino)methyl)-[1,1'-biphenyl]-4-yl)-2-methyl-1H-benzo[d]imidazole-4-carboxylic acid.2,2,2-trifluoroacetic acid; |
| 39. | 6-(3'-((tert-butylamino)methyl)-[1,1'-biphenyl]-4-yl)-2-methyl-1H-benzo[d]imidazole-4-carboxylic acid.2,2,2-trifluoroacetic acid; |
| 40. | 6-(3'-((cycloheptylamino)methyl)-[1,1'-biphenyl]-4-yl)-2-methyl-1H-benzo[d]imidazole-4-carboxylic acid.2,2,2-trifluoroacetic acid; |
| 41. | 6-(3'-((3-hydroxyazetidin-1-yl)methyl)-[1,1'-biphenyl]-4-yl)-2-methyl-1H-benzo[d]imidazole-4-carboxylic acid.2,2,2-trifluoroacetic acid; |
| 42. | 2-methyl-6-(2'-(piperidin-1-ylmethyl)-[1,1'-biphenyl]-4-yl)-1H-benzo[d]imidazole-4-carboxylic acid.2,2,2-trifluoroacetic acid; |
| 43. | 6-(2'-((isopropylamino)methyl)-[1,1'-biphenyl]-4-yl)-2-methyl-1H-benzo[d]imidazole-4-carboxylic acid.2,2,2-trifluoroacetic acid; |
| 44. | 2-methyl-6-(2'-(thiomorpholinomethyl)-[1,1'-biphenyl]-4-yl)-1H-benzo[d]imidazole-4-carboxylic acid.2,2,2-trifluoroacetic acid; |
| 45. | 2-methyl-6-(2'-(morpholinomethyl)-[1,1'-biphenyl]-4-yl)-1H-benzo[d]imidazole-4-carboxylic acid.2,2,2-trifluoroacetic acid; |
| 46. | 2-methyl-6-(2'-(pyrrolidin-1-ylmethyl)-[1,1'-biphenyl]-4-yl)-1H-benzo[d]imidazole-4-carboxylic acid.2,2,2-trifluoroacetic acid; |
| 47. | 6-(2'-((1,1-dioxidothiomorpholino)methyl)-[1,1'-biphenyl]-4-yl)-2-methyl-1H-benzo[d]imidazole-4-carboxylic acid.2,2,2-trifluoroacetic acid; |
| 48. | 6-(2'-((cyclopropylamino)methyl)-[1,1'-biphenyl]-4-yl)-2-methyl-1H-benzo[d]imidazole-4-carboxylic acid.2,2,2-trifluoroacetic acid; |
| 49. | 6-(2'-((dimethylamino)methyl)-[1,1'-biphenyl]-4-yl)-2-methyl-1H-benzo[d]imidazole-4-carboxylic acid.2,2,2-trifluoroacetic acid; |
| 50. | 6-(2'-((3,3-difluoropiperidin-1-yl)methyl)-[1,1'-biphenyl]-4-yl)-2-methyl-1H-benzo[d]imidazole-4-carboxylic acid.2,2,2-trifluoroacetic acid; |
| 51. | 6-(2'-((cycloheptylamino)methyl)-[1,1'-biphenyl]-4-yl)-2-methyl-1H-benzo[d]imidazole-4-carboxylic acid.2,2,2-trifluoroacetic acid; |
| 52. | 2-methyl-6-(2,3,5,6-tetrafluoro-[1,1'-biphenyl]-4-yl)-1H-benzo[d]imidazole-4-carboxylic acid; |
| 53. | 2-methyl-6-(2,3,5,6-tetrafluoro-2'-(piperidin-1-ylmethyl)-[1,1'-biphenyl]-4-yl)-1H-benzo[d]imidazole-4-carboxylic acid.2,2,2-trifluoroacetic acid; |
| 54. | 2-methyl-6-(2,3,5,6-tetrafluoro-2'-(thiomorpholinomethyl)-[1,1'-biphenyl]-4-yl)-1H-benzo[d]imidazole-4-carboxylic acid.2,2,2-trifluoroacetic acid; |
| 55. | 2-methyl-6-(2,3,5,6-tetrafluoro-2'-((isopropylamino)methyl)-[1,1'-biphenyl]-4-yl)-1H-benzo[d]imidazole-4-carboxylic acid.2,2,2-trifluoroacetic acid; |
| 56. | 2-methyl-6-(2,3,5,6-tetrafluoro-3'-(piperidin-1-ylmethyl)-[1,1'-biphenyl]-4-yl)-1H-benzo[d]imidazole-4-carboxylic acid.2,2,2-trifluoroacetic acid; |
| 57. | 2-methyl-6-(2,3,5,6-tetrafluoro-3'-(hydroxymethyl)-[1,1'-biphenyl]-4-yl)-1H-benzo[d]imidazole-4-carboxylic acid.2,2,2-trifluoroacetic acid; |
| 58. | 2-methyl-6-(2,3,5,6-tetrafluoro-3'-(pyrrolidin-1-ylmethyl)-[1,1'-biphenyl]-4-yl)-1H-benzo[d]imidazole-4-carboxylic acid; |
| 59. | 2-methyl-6-(2,3,5,6-tetrafluoro-3'-((isopropylamino)methyl)-[1,1'-biphenyl]-4-yl)-1H-benzo[d]imidazole-4-carboxylic acid.2,2,2-trifluoroacetic acid; |
| 60. | 6-(3'-((cyclopropylamino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 61. | 2-methyl-6-(2,3,5,6-tetrafluoro-4'-(piperidin-1-ylmethyl)-[1,1'-biphenyl]-4-yl)-1H-benzo[d]imidazole-4-carboxylic acid.2,2,2-trifluoroacetic acid; |
| 62. | 2-methyl-6-(2,3,5,6-tetrafluoro-4'-(pyrrolidin-1-ylmethyl)-[1,1'-biphenyl]-4- |

| Example No | IUPAC names |
|---|---|
| | yl)-1H-benzo[d]imidazole-4-carboxylic acid.2,2,2-trifluoroacetic acid; |
| 63. | 2-methyl-6-(2,3,5,6-tetrafluoro-4'-(thiomorpholinomethyl)-[1,1'-biphenyl]-4-yl)-1H-benzo[d]imidazole-4-carboxylic acid.2,2,2-trifluoroacetic acid; |
| 64. | 6-(4'-((3,3-difluoropiperidin-1-yl)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 65. | 6-(4'-((1,1-dioxidothiomorpholino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 66. | 2-methyl-6-(2,3,5,6-tetrafluoro-4'-((isopropylamino)methyl)-[1,1'-biphenyl]-4-yl)-1H-benzo[d]imidazole-4-carboxylic acid.2,2,2-trifluoroacetic acid; |
| 67. | 6-(4-(2,5-dimethyl-1H-pyrrol-1-yl)-2,3,5,6-tetrafluorophenyl)-2-methyl-1H-benzo[d]imidazole-4-carboxylic acid; |
| 68. | 6-([1,1'-biphenyl]-4-yl)-1,2-dimethyl-1H-benzo[d]imidazole-4-carboxylic acid; |
| 69. | 6-(4-(benzyloxy)phenyl)-2-methyl-1H-benzo[d]imidazole-4-carboxylic acid; |
| 70. | 2-methyl-6-(4'-(piperidin-4-ylmethoxy)-[1,1'-biphenyl]-4-yl)-1H-benzo[d]imidazole-4-carboxylic acid.2,2,2-trifluoroacetic acid; |
| 71. | 2-methyl-6-(4'-(2-(piperidin-4-yl)ethoxy)-[1,1'-biphenyl]-4-yl)-1H-benzo[d]imidazole-4-carboxylic acid.2,2,2-trifluoroacetic acid; |
| 72. | 2-methyl-6-(3'-(piperidin-4-ylmethoxy)-[1,1'-biphenyl]-4-yl)-1H-benzo[d]imidazole-4-carboxylic acid.2,2,2-trifluoroacetic acid; |
| 73. | 2-methyl-6-(3'-(piperidin-4-yloxy)-[1,1'-biphenyl]-4-yl)-1H-benzo[d]imidazole-4-carboxylic acid.2,2,2-trifluoroacetic acid; |
| 74. | 2-methyl-6-(4'-(2-morpholinoethoxy)-[1,1'-biphenyl]-4-yl)-1H-benzo[d]imidazole-4-carboxylic acid.2,2,2-trifluoroacetic acid; |
| 75. | 2-methyl-6-(3'-(2-(piperidin-4-yl)ethoxy)-[1,1'-biphenyl]-4-yl)-1H-benzo[d]imidazole-4-carboxylic acid.2,2,2-trifluoroacetic acid; |
| 76. | 2-methyl-6-(3'-(2-(tetrahydro-2H-pyran-4-yl)ethoxy)-[1,1'-biphenyl]-4-yl)-1H-benzo[d]imidazole-4-carboxylic acid.2,2,2-trifluoroacetic acid; |
| 77. | (S)-2-methyl-6-(3'-(pyrrolidine-2-carboxamido)-[1,1'-biphenyl]-4-yl)-1H-benzo[d]imidazole-4-carboxylic acid.2,2,2-trifluoroacetic acid; |
| 78. | 2-methyl-6-(3'-(piperidine-4-carboxamido)-[1,1'-biphenyl]-4-yl)-1H-benzo[d]imidazole-4-carboxylic acid.2,2,2-trifluoroacetic acid; |
| 79. | 2-methyl-6-(2'-(methylsulfonyl)-[1,1'-biphenyl]-4-yl)-1H-benzo[d]imidazole-4-carboxylic acid.2,2,2-trifluoroacetic acid; |
| 80. | 2-methyl-6-(3'-(methylsulfonyl)-[1,1'-biphenyl]-4-yl)-1H-benzo[d]imidazole-4-carboxylic acid; |
| 81. | 2-methyl-6-(4'-(methylsulfonyl)-[1,1'-biphenyl]-4-yl)-1H-benzo[d]imidazole-4-carboxylic acid.2,2,2-trifluoroacetic acid; |
| 82. | 6-(2'-((benzylamino)methyl)-[1,1'-biphenyl]-4-yl)-2-methyl-1H-benzo[d]imidazole-4-carboxylic acid.2,2,2-trifluoroacetic acid; |
| 83. | 6-(4'-(methoxymethyl)-[1,1'-biphenyl]-4-yl)-2-methyl-1H-benzo[d]imidazole-4-carboxylic acid; |
| 84. | 2-methyl-6-(2,3,5,6-tetrafluoro-3'-(morpholinomethyl)-[1,1'-biphenyl]-4-yl)-1H-benzo[d]imidazole-4-carboxylic acid.2,2,2-trifluoroacetic acid; |
| 85. | 2-methyl-6-(4'-((methylsulfonyl)methyl)-[1,1'-biphenyl]-4-yl)-1H-benzo[d]imidazole-4-carboxylic acid; |
| 86. | 2-methyl-6-(4'-((methylthio)methyl)-[1,1'-biphenyl]-4-yl)-1H-benzo[d]imidazole-4-carboxylic acid; |
| 87. | 6-(3'-((benzylamino)methyl)-[1,1'-biphenyl]-4-yl)-2-methyl-1H-benzo[d]imidazole-4-carboxylic acid; |
| 88. | 6-(2'-(hydroxymethyl)-[1,1'-biphenyl]-4-yl)-2-methyl-1H-benzo[d]imidazole-4-carboxylic acid; |
| 89. | 2-methyl-6-(4'-methyl-[1,1'-biphenyl]-4-yl)-1H-benzo[d]imidazole-4-carboxylic acid; |
| 90. | 6-(3'-(hydroxymethyl)-[1,1'-biphenyl]-4-yl)-2-methyl-1H-benzo[d]imidazole-4-carboxylic acid; |
| 91. | 6-(4'-((benzylamino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 92. | 2-methyl-6-(2,3,5,6-tetrafluoro-4'-(methylthio)-[1,1'-biphenyl]-4-yl)-1H-benzo[d]imidazole-4-carboxylic acid; |
| 93. | 2-methyl-6-(2,3,5,6-tetrafluoro-4'-(methylsulfonyl)-[1,1'-biphenyl]-4-yl)-1H-benzo[d]imidazole-4-carboxylic acid; |
| 94. | 6-(2'-((4-hydroxypiperidin-1-yl)methyl)-[1,1'-biphenyl]-4-yl)-2-methyl-1H-benzo[d]imidazole-4-carboxylic acid.2,2,2-trifluoroacetic acid; |
| 95. | (R)-6-(3'-((3-hydroxypyrrolidin-1-yl)methyl)-[1,1'-biphenyl]-4-yl)-2-methyl-1H-benzo[d]imidazole-4-carboxylic acid.2,2,2-trifluoroacetic acid; |
| 96. | 2-methyl-6-(4'-(piperidin-1-yl)-[1,1'-biphenyl]-4-yl)-1H-benzo[d]imidazole-4-carboxylic acid.2,2,2-trifluoroacetic acid; |
| 97. | 2-methyl-6-(3'-((4-methylpiperidin-1-yl)methyl)-[1,1'-biphenyl]-4-yl)-1H-benzo[d]imidazole-4-carboxylic acid.2,2,2-trifluoroacetic acid; |
| 98. | 6-(3'-((cyclopentylamino)methyl)-[1,1'-biphenyl]-4-yl)-2-methyl-1H-benzo[d]imidazole-4-carboxylic acid.2,2,2-trifluoroacetic acid; |
| 99. | 6-(3'-(((cyclopropylmethyl)amino)methyl)-[1,1'-biphenyl]-4-yl)-2-methyl-1H-benzo[d]imidazole-4-carboxylic acid.2,2,2-trifluoroacetic acid; |
| 100. | 6-(3'-((4-hydroxypiperidin-1-yl)methyl)-[1,1'-biphenyl]-4-yl)-2-methyl-1H-benzo[d]imidazole-4-carboxylic acid.2,2,2-trifluoroacetic acid; |
| 101. | 6-(4'-(hydroxymethyl)-[1,1'-biphenyl]-4-yl)-2-methyl-1H-benzo[d]imidazole-4-carboxylic acid; |
| 102. | 6-(2'-((3-hydroxyazetidin-1-yl)methyl)-[1,1'-biphenyl]-4-yl)-2-methyl-1H-benzo[d]imidazole-4-carboxylic acid; |
| 103. | 6-(2'-((dipropylamino)methyl)-[1,1'-biphenyl]-4-yl)-2-methyl-1H-benzo[d]imidazole-4-carboxylic acid; |
| 104. | 6-(2'-(((2-methoxyethyl)amino)methyl)-[1,1'-biphenyl]-4-yl)-2-methyl-1H-benzo[d]imidazole-4-carboxylic acid; |
| 105. | 2-methyl-6-(2'-((2-oxoazepan-1-yl)methyl)-[1,1'-biphenyl]-4-yl)-1H-benzo[d]imidazole-4-carboxylic acid; |
| 106. | 6-(2'-((tert-butylamino)methyl)-[1,1'-biphenyl]-4-yl)-2-methyl-1H-benzo[d]imidazole-4-carboxylic acid.2,2,2-trifluoroacetic acid; |

| Example No | IUPAC names |
|---|---|
| 107. | (R)-6-(2'-((3-hydroxypyrrolidin-1-yl)methyl)-[1,1'-biphenyl]-4-yl)-2-methyl-1H-benzo[d]imidazole-4-carboxylic acid.2,2,2-trifluoroacetic acid; |
| 108. | 2-methyl-6-(2'-((4-methylpiperidin-1-yl)methyl)-[1,1'-biphenyl]-4-yl)-1H-benzo[d]imidazole-4-carboxylic acid.2,2,2-trifluoroacetic acid; |
| 109. | 2-methyl-6-(2'-((2-oxopyrrolidin-1-yl)methyl)-[1,1'-biphenyl]-4-yl)-1H-benzo[d]imidazole-4-carboxylic acid.2,2,2-trifluoroacetic acid; |
| 110. | 6-(2'-(((cyclopropylmethyl)amino)methyl)-[1,1'-biphenyl]-4-yl)-2-methyl-1H-benzo[d]imidazole-4-carboxylic acid.2,2,2-trifluoroacetic acid; |
| 111. | 6-(4-(2,5-dimethyl-1H-pyrrol-1-yl)phenyl)-2-methyl-1H-benzo[d]imidazole-4-carboxylic acid; |
| 112. | 6-(3'-(((2-methoxyethyl)amino)methyl)-[1,1'-biphenyl]-4-yl)-2-methyl-1H-benzo[d]imidazole-4-carboxylic acid.2,2,2-trifluoroacetic acid; |
| 113. | 2-methyl-6-(3'-((prop-2-yn-1-ylamino)methyl)-[1,1'-biphenyl]-4-yl)-1H-benzo[d]imidazole-4-carboxylic acid.2,2,2-trifluoroacetic acid; |
| 114. | 2-methyl-6-(3'-(((2-(methylsulfonyl)ethyl)amino)methyl)-[1,1'-biphenyl]-4-yl)-1H-benzo[d]imidazole-4-carboxylic acid.2,2,2-trifluoroacetic acid; |
| 115. | (R)-6-(3'-((3-fluoropyrrolidin-1-yl)methyl)-[1,1'-biphenyl]-4-yl)-2-methyl-1H-benzo[d]imidazole-4-carboxylic acid.2,2,2-trifluoroacetic acid; |
| 116. | 2-methyl-6-(2'-(((1-methylpiperidin-4-yl)amino)methyl)-[1,1'-biphenyl]-4-yl)-1H-benzo[d]imidazole-4-carboxylic acid.2,2,2-trifluoroacetic acid; |
| 117. | (R)-6-(2'-((3-fluoropyrrolidin-1-yl)methyl)-[1,1'-biphenyl]-4-yl)-2-methyl-1H-benzo[d]imidazole-4-carboxylic acid.2,2,2-trifluoroacetic acid; |
| 118. | 6-(2'-((cyclohexylamino)methyl)-[1,1'-biphenyl]-4-yl)-2-methyl-1H-benzo[d]imidazole-4-carboxylic acid.2,2,2-trifluoroacetic acid; |
| 119. | 6-(2'-((cyclohexyl(methyl)amino)methyl)-[1,1'-biphenyl]-4-yl)-2-methyl-1H-benzo[d]imidazole-4-carboxylic acid; |
| 120. | (R)-2-methyl-6-(2,3,5,6-tetrafluoro-4'-((2-hydroxypyrrolidin-1-yl)methyl)-[1,1'-biphenyl]-4-yl)-1H-benzo[d]imidazole-4-carboxylic acid; |
| 121. | 2-methyl-6-(2,3,5,6-tetrafluoro-4'-((4-methylpiperidin-1-yl)methyl)-[1,1'-biphenyl]-4-yl)-1H-benzo[d]imidazole-4-carboxylic acid.2,2,2-trifluoroacetic acid; |
| 122. | 6-(4'-(((cyclopropylmethyl)amino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 123. | (R)-2-methyl-6-(2,3,5,6-tetrafluoro-4'-((2-fluoropyrrolidin-1-yl)methyl)-[1,1'-biphenyl]-4-yl)-1H-benzo[d]imidazole-4-carboxylic acid.2,2,2-trifluoroacetic acid; |
| 124. | 6-(3'-(((cyclohexylmethyl)amino)methyl)-[1,1'-biphenyl]-4-yl)-2-methyl-1H-benzo[d]imidazole-4-carboxylic acid.2,2,2-trifluoroacetic acid; |
| 125. | 6-(3'-(((3-(dimethylamino)propyl)amino)methyl)-[1,1'-biphenyl]-4-yl)-2-methyl-1H-benzo[d]imidazole-4-carboxylic acid.2,2,2-trifluoroacetic acid; |
| 126. | 6-(3'-((diisobutylamino)methyl)-[1,1'-biphenyl]-4-yl)-2-methyl-1H-benzo[d]imidazole-4-carboxylic acid.2,2,2-trifluoroacetic acid; |
| 127. | 2-methyl-6-(2,3,5,6-tetrafluoro-4'-((prop-2-yn-1-ylamino)methyl)-[1,1'-biphenyl]-4-yl)-1H-benzo[d]imidazole-4-carboxylic acid.2,2,2-trifluoroacetic acid; |
| 128. | 6-(4'-((cyclohexylamino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 129. | 6-(2'-(((cyclohexylmethyl)amino)methyl)-[1,1'-biphenyl]-4-yl)-2-methyl-1H-benzo[d]imidazole-4-carboxylic acid.2,2,2-trifluoroacetic acid; |
| 130. | 6-(2'-(((4-hydroxycyclohexyl)amino)methyl)-[1,1'-biphenyl]-4-yl)-2-methyl-1H-benzo[d]imidazole-4-carboxylic acid.2,2,2-trifluoroacetic acid; |
| 131. | 2-methyl-6-(2'-((prop-2-yn-1-ylamino)methyl)-[1,1'-biphenyl]-4-yl)-1H-benzo[d]imidazole-4-carboxylic acid.2,2,2-trifluoroacetic acid; |
| 132. | (E)-6-(3'-((methoxyimino)methyl)-[1,1'-biphenyl]-4-yl)-2-methyl-1H-benzo[d]imidazole-4-carboxylic acid; |
| 133. | 6-(2'-(((3-(dimethylamino)propyl)amino)methyl)-[1,1'-biphenyl]-4-yl)-2-methyl-1H-benzo[d]imidazole-4-carboxylic acid.2,2,2-trifluoroacetic acid; |
| 134. | 6-(2-(2,5-dimethyl-1H-pyrrol-1-yl)phenyl)-2-methyl-1H-benzo[d]imidazole-4-carboxylic acid; |
| 135. | 2-methyl-6-(3'-(((2,2,2-trifluoroethyl)amino)methyl)-[1,1'-biphenyl]-4-yl)-1H-benzo[d]imidazole-4-carboxylic acid.2,2,2-trifluoroacetic acid; |
| 136. | 2-methyl-6-(3'-(((3,3,3-trifluoropropyl)amino)methyl)-[1,1'-biphenyl]-4-yl)-1H-benzo[d]imidazole-4-carboxylic acid.2,2,2-trifluoroacetic acid; |
| 137. | 6-(3'-((1,1-dioxidothiomorpholino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 138. | 6-(4-(3,5-dimethyl-1H-pyrazol-1-yl)phenyl)-2-methyl-1H-benzo[d]imidazole-4-carboxylic acid.2,2,2-trifluoroacetic acid; |
| 139. | 2-methyl-6-(4-(3-methyl-1H-pyrazol-1-yl)phenyl)-1H-benzo[d]imidazole-4-carboxylic acid.2,2,2-trifluoroacetic acid; |
| 140. | 6-(2'-((diisobutylamino)methyl)-[1,1'-biphenyl]-4-yl)-2-methyl-1H-benzo[d]imidazole-4-carboxylic acid; |
| 141. | 2-methyl-6-(2'-(((2-(piperidin-1-yl)ethyl)amino)methyl)-[1,1'-biphenyl]-4-yl)-1H-benzo[d]imidazole-4-carboxylic acid; |
| 142. | 2-methyl-6-(2'-(((3,3,3-trifluoropropyl)amino)methyl)-[1,1'-biphenyl]-4-yl)-1H-benzo[d]imidazole-4-carboxylic acid; |
| 143. | (E)-6-(3'-((ethoxyimino)methyl)-[1,1'-biphenyl]-4-yl)-2-methyl-1H-benzo[d]imidazole-4-carboxylic acid.2,2,2-trifluoroacetic acid; |
| 144. | 6-(4-(4,5-dimethyloxazol-2-yl)phenyl)-2-methyl-1H-benzo[d]imidazole-4-carboxylic acid.2,2,2-trifluoroacetic acid; |
| 145. | 6-(2',6'-dimethyl-[1,1'-biphenyl]-4-yl)-2-methyl-1H-benzo[d]imidazole-4-carboxylic acid; |

| Example No | IUPAC names |
|---|---|
| 146. | 6-(4'-(((3-(dimethylamino)propyl)amino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 147. | 2-methyl-6-(2,3,5,6-tetrafluoro-4-(morpholinomethyl)phenyl)-1H-benzo[d]imidazole-4-carboxylic acid.2,2,2-trifluoroacetic acid; |
| 148. | (R)-2-methyl-6-(2,3,5,6-tetrafluoro-3'-((3-fluoropyrrolidin-1-yl)methyl)-[1,1'-biphenyl]-4-yl)-1H-benzo[d]imidazole-4-carboxylic acid.2,2,2-trifluoroacetic acid; |
| 149. | (R)-2-methyl-6-(2,3,5,6-tetrafluoro-3'-((3-hydroxypyrrolidin-1-yl)methyl)-[1,1'-biphenyl]-4-yl)-1H-benzo[d]imidazole-4-carboxylic acid.2,2,2-trifluoroacetic acid; |
| 150. | 6-(2'-fluoro-6'-(pyrrolidin-1-ylmethyl)-[1,1'-biphenyl]-4-yl)-2-methyl-1H-benzo[d]imidazole-4-carboxylic acid.2,2,2-trifluoroacetic acid; |
| 151. | 6-(3-(2,5-dimethyl-1H-pyrrol-1-yl)phenyl)-2-methyl-1H-benzo[d]imidazole-4-carboxylic acid; |
| 152. | 2-methyl-6-(2'-(((3-morpholinopropyl)amino)methyl)-[1,1'-biphenyl]-4-yl)-1H-benzo[d]imidazole-4-carboxylic acid.2,2,2-trifluoroacetic acid; |
| 153. | 6-(2'-(((2-(dimethylamino)ethyl)(methyl)amino)methyl)-[1,1'-biphenyl]-4-yl)-2-methyl-1H-benzo[d]imidazole-4-carboxylic acid.2,2,2-trifluoroacetic acid; |
| 154. | 6-(2'-((3,3-difluoropiperidin-1-yl)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 155. | 6-(3'-((cyclohexylamino)methyl)-2,3,5,6-tetrafluoro-[1,1'-biphenyl]-4-yl)-2-methyl-1H-benzo[d]imidazole-4-carboxylic acid.2,2,2-trifluoroacetic acid; and |
| 156. | 2-methyl-6-(2'-(((2-(methylsulfonyl)ethyl)amino)methyl)-[1,1'-biphenyl]-4-yl)-1H-benzo[d]imidazole-4-carboxylic acid.2,2,2-trifluoroacetic acid; | or a pharmaceutically acceptable salt or a stereoisomer thereof.

In certain embodiments, the present invention provides processes for preparing 1, 4, 6-trisubstituted-2-alkyl-1H-benzo[d]imidazole derivatives of formula (I).

In certain embodiments, the present invention provides a pharmaceutical composition comprising the compound of formula (I) or (IA) or (IB) or a pharmaceutically acceptable salt or stereoisomer thereof and at least one pharmaceutically acceptable excipient (such as a pharmaceutically acceptable carrier or diluent). In certain preferred embodiments, the pharmaceutical composition comprises a therapeutically effective amount of at least one compounds of formula (I).

In certain embodiments, the present invention provides a pharmaceutical composition comprising a compound as disclosed herein, optionally admixed with a pharmaceutically acceptable carrier or diluent.

The present invention also provides methods for formulating the disclosed compounds for pharmaceutical administration.

The compositions and methods of the present invention may be utilized to treat an individual in need thereof. In certain embodiments, the individual is a mammal such as a human or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers or finely divided solid carriers or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylatedisostearyl alcohols, polyoxyethylene sorbitol and sorbitan esters, microcrystalline cellulose, aluminummetahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash or an oral spray or an oral ointment.

Alternatively or additionally, compositions can be formulated for delivery via a catheter, stent, wire or other intraluminal device. Delivery via such devices may be especially useful for delivery to the bladder, urethra, ureter, rectum or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to an active compound, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminummonostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbylpalmitate, butylated hydroxyanisole (BHA), butylated hydroxytoluene (BHT), lecithin, propyl gallate, alpha-tocopherol, and the like; and (3) metal-chelating agents, such as citric acid, ethylenediaminetetraacetic acid (EDTA), sorbitol, tartaric acid, phosphoric acid, and the like.

In certain embodiments, the present disclosure provides uses of compound of formula (I) as a medicament for the treatment of autoimmune and inflammatory disorders.

In certain embodiments, the present disclosure provides uses of compound of formula (I) as a medicament for the treatment inflammatory disorders such as multiple sclerosis, rheumatoid arthritis; and also diseases like cancer.

In certain embodiments, the invention embodiments provides the use of compounds of formula (I) and pharmaceutically acceptable salts solvate, tautomers, and stereoisomers thereof, including mixtures thereof in all ratios as a medicament, by inhibiting dihydroorotate oxygenase enzyme activity in treating disorder like multiple sclerosis and other diseases such as inflammatory disorders, rheumatoid arthritis and cancer.

In certain embodiments, the present invention provides the methods for treating diseases or disorders mediated by dihydroorotate dehydrogenase (DHODH or DHOD) enzyme comprising administering the compound of formula (I).

In certain embodiments, the diseases or disorders mediated by dihydroorotate dehydrogenase (DHODH or DHOD) comprises, but not restricted to, autoimmune and chronic inflammatory diseases, including systemic lupus erythematosus, chronic rheumatoid arthritis, multiple sclerosis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma.

The compounds of formula (I) and related formulae can be also useful as part of chemotherapeutic regimens for the treatment of cancers, Lymphomas and leukemias alone or in combination with classic antitumoral compounds well known by the one skilled in the art.

In one embodiment, the condition treated by a compound of formula (I) of the present invention or a pharmaceutically acceptable salt thereof or a pharmaceutical composition comprising the same is a lymphoma selected from Hodgkin's disease, non-Hodgkin's lymphoma, follicular lymphoma, diffuse large B cell lymphoma or DLBCL (including forms of DLBCL that are characterized by gene alterations at c-MYC and BCL2; gene alterations at c-MYC and BCL6; and gene alterations at c-MYC, BCL2, and BCL6), anaplastic large cell lymphoma, mantle cell lymphoma, primary CNS lymphoma, lymphocytic lymphoma, and T-cell lymphoma. In another embodiment, the lymphoma treated by a compound of formula (I) of the present invention or a pharmaceutically acceptable salt thereof or a pharmaceutical composition comprising the same is selected from diffuse mixed cell lymphoma, and primary effusion lymphoma.

In one embodiment, the condition treated by a compound of formula (I) of the present invention or a pharmaceutically acceptable salt thereof or a pharmaceutical composition comprising the same is a leukemia selected from acute myeloid leukemia, B-prolymphocytic leukemia, acute lymphoblastic leukemia, and chronic lymphocytic leukemia. In another embodiment, the leukemia treated by a compound of formula (I) of the present invention or a pharmaceutically acceptable salt thereof or a pharmaceutical composition comprising the same is selected from acute monocytic leukemia, acute lymphoblastic leukemia, erythroleukemia, chronic myeloid leukemia, and chronic monocytic leukemia.

In one embodiment, the condition treated by a compound of formula (I) of the present invention or a pharmaceutically acceptable salt thereof or a pharmaceutical composition comprising the same is multiple myeloma.

In another embodiment, the condition treated by a compound of formula (I) of the present invention or a pharmaceutically acceptable salt thereof or a pharmaceutical composition comprising the same is myelodysplastic syndrome.

In one embodiment, the condition treated by a compound of formula (I) of the present invention or a pharmaceutically acceptable salt thereof or a pharmaceutical composition comprising the same is a solid tumor selected from lung cancer, breast cancer, triple negative breast cancer, melanoma, glioblastoma, prostate cancer, colon cancer, pancreatic cancer, bone cancer, cancer of the head or neck, skin cancer, cutaneous or intraocular malignant endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, Kaposi's sarcoma, epidermoid cancer, squamous cell cancer, an environmentally induced cancer, and a PTEN mutant cancer. In another embodiment, the solid tumor treated by a compound of formula (I) of the present invention or a pharmaceutically acceptable salt thereof or a pharmaceutical composition comprising the same is selected from sarcomatoid carcinoma, biliary tract cancer or cancer of the ampulla of Vater, non-small cell lung cancer, bronchoalveolar carcinoma, liver cancer, cancer of the ovary, and cancer of the upper aerodigestive tract.

In yet another embodiment, the present invention relates to compounds of formula (I) for use in the treatment of inflammatory disorders and autoimmune diseases or overactive immune response. More preferably, the present invention relates to the use of compounds of formula (I) for the treatment of multiple sclerosis, rheumatoid arthritis and transplant rejection.

Use of compounds as above and pharmaceutically usable derivatives, salts, tautomers, solvates and stereoisomers thereof, including mixtures thereof in all ratios, for the preparation of a medicament for the treatment and/or prophylaxis of a dihydroorotate dehydrogenase associated disorder.

Use of compounds as above wherein the dihydroorotate dehydrogenase associated disorder is an autoimmune disorder or condition associated with an overactive immune response.

Use of compounds as above and pharmaceutically usable derivatives, salts, tautomers, solvates and stereoisomers thereof, including mixtures thereof in all ratios, for the preparation of a medicament for the treatment and/or prophylaxis of an immunerogulatory abnormality.

Use of compounds as above wherein the immunoregulatory abnormality is multiple sclerosis or rheumatoid arthritis.

Use of the compounds as above for the preparation of a medicament for the treatment and prophylaxis of cancer diseases, inflammatory bowel disease or rheumatoid arthritis.

In certain embodiment, the present disclosure provides the compound of formula (I) for use as a medicament.

In certain embodiments, the present invention provides the compounds of formula (I) for use in the treatment of autoimmune and chronic inflammatory diseases, including systemic lupus erythematosus, chronic rheumatoid arthritis, multiple sclerosis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma.

The term "diseases or conditions for which a dihydroorotateoxygenase inhibitor is indicated", is intended to include each of or all of the above disease states.

While it is possible that for use in therapy, a compound of formula (I) as well as pharmaceutically acceptable salts thereof may be administered as the raw chemical, it is common to present the active ingredient as a pharmaceutical composition.

The compounds and pharmaceutically compositions of the present invention may be used in combination with other drugs that are used in the treatment/prevention/suppression or amelioration of the diseases or conditions for which compounds of the present invention may be useful. Such other drugs may be administered, by a route and in an amount commonly used there for, contemporaneously or sequentially with a compound of the present invention. When a compound of the present invention is used contemporaneously with one or more other drugs, a pharmaceutical composition containing such other drugs in addition to the compound of the present invention may also be preferred. Accordingly, the pharmaceutical compositions of the present invention include those that also contain one or more other active ingredients, in addition to a compound of the present invention.

A pharmaceutical composition of the invention may be formulated as being compatible with its intended route of administration, which may preferably be an oral administration. For example the pharmaceutical compositions of the invention may be formulated for administration by inhalation, such as aerosols or dry powders; for oral administration, such in the form of tablets, capsules, gels, syrups, suspensions, emulsions, elixirs, solutions, powders or granules; for rectal or vaginal administration, such as suppositories; or for parenteral injection (including intravenous, subcutaneous, intramuscular, intravascular, or infusion) such as a sterile solution, suspension or emulsion.

The compounds of the present invention may also be entrapped in microcapsules prepared, for example, by coacervation techniques or by interfacial polymerization, for example, hydroxymethyl cellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

In a further aspect, the present invention relates to a process for preparing 1, 4, 6-trisubstituted-2-alkyl-1H-benzo[d]imidazole derivatives of formula (I).

The dihydroorotate dehydrogenase inhibitors according to formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. Moreover, by utilizing the procedures described in detail, one of ordinary skill in the art can prepare additional compounds of the present invention claimed herein. All temperatures are in degrees Celsius (° C.) unless otherwise noted.

In a further aspect, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}$H ("D"), $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Isotopically labeled compounds of the present inventions can generally be prepared by following procedures analogous to those disclosed in the Schemes and/or in the Examples herein below, by substituting an isotopically labeled reagent for a non-isotopically labeled reagent.

The abbreviations used in the entire specification may be summarized herein below with their particular meaning.

AcNH$_2$ (Acetamide), AcOH (Acetic acid), ATP (Adenoside Triphosphate), BSA (Bovine Serum Albumin), Bu$_4$NOH (Tetrabutylammonium hydroxide), CDI (1,1'-Carbonyldiimidazole), CHCl$_3$ (Chloroform), Cs$_2$CO$_3$ (Cesium carbonate), cHex (Cyclohexanes), CH$_3$NO$_2$ (Nitromethane), DBU (1,8-Dizabicyclo[5.4.0]undec-7-ene), DCM (Dichloromethane), DIPEA (di-isopropyl ethylamine), DMAP (4-Dimethylaminopyridine), DMSO (Dimethyl Sulfoxide), DMF (N,N-Dimethylformamide), Et$_3$N (Triethylamine), EtOAc (Ethyl acetate), EtOH (Ethanol), FC (Flash Chromatography on silica gel), g (gram), HCl (hydrogen chloride), HATU (2-(1H-7-Azabenzotriazol-1-yl)-1,1,3,3-tetramethyl uroniumhexafluorophosphateMethanaminium), h (hour), HPLC (High Performance Liquid Chromatography), K$_2$CO$_3$ (Potassium Carbonate), min (minute), MHz (Megahertz), mL (milliliter), mmol (millimole), mM (millimolar), MeOH (Methanol), MgSO$_4$ (Magnesium sulfate), MS (Mass Spectrometry), NH$_4$Cl (Ammonium chloride), NH$_4$(CO$_3$)$_2$ (ammonium carbonate), NaI (Sodium Iodine), NaH (Sodium hydride), NaHCO$_3$ (Sodium bicarbonate), NMR (Nuclear Magnetic Resonance), PdCl$_2$ (Palladium dichloride), PetEther (Petroleum ether), PtO$_2$ (Platinium oxide), PBS (Phosphate Buffered Saline), RT (room temperature), TEA (Triethyl amine), TFA (Trifluoroacetic acid), THF (Tetrahydrofuran), tBuOK (Potassium tert-butoxide), TBME (tert-Butyl Methyl Ether), TMSI (Trimethylsilyl iodide), TLC (Thin Layer Chromatography), UV (Ultraviolet). Zn (Zinc powder).

Another embodiment of the present invention provides methods useful for making the compounds of Formula (I) are set forth in the Examples below and generalized in Schemes I and II. One of skill in the art will recognize that Schemes I and II can be adapted to produce the compounds of Formula (I) and pharmaceutically accepted salts of compounds of Formula (I) according to the present invention. Wherein all symbols/variables are as defined earlier unless otherwise stated. The process is represented by Schemes I and II.

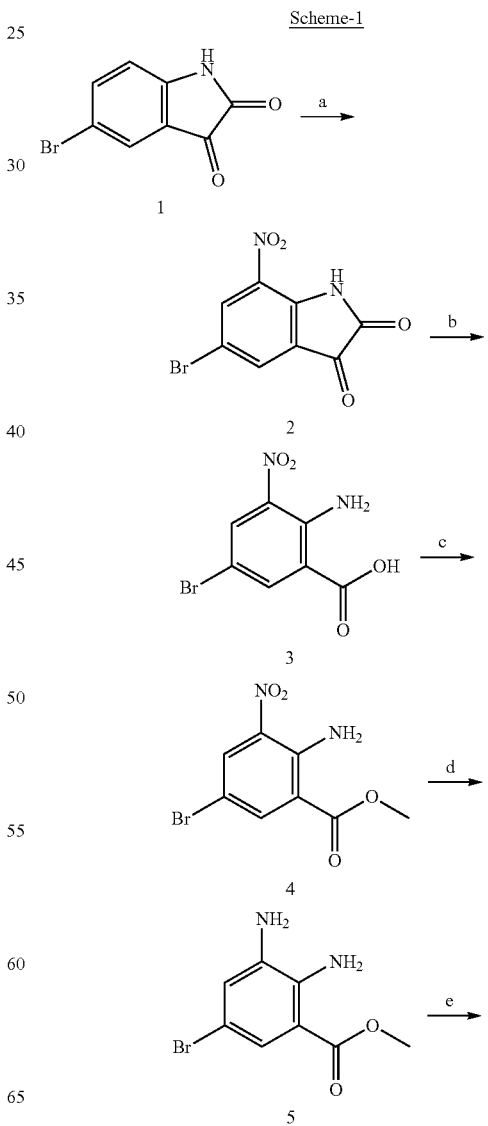

Scheme-1

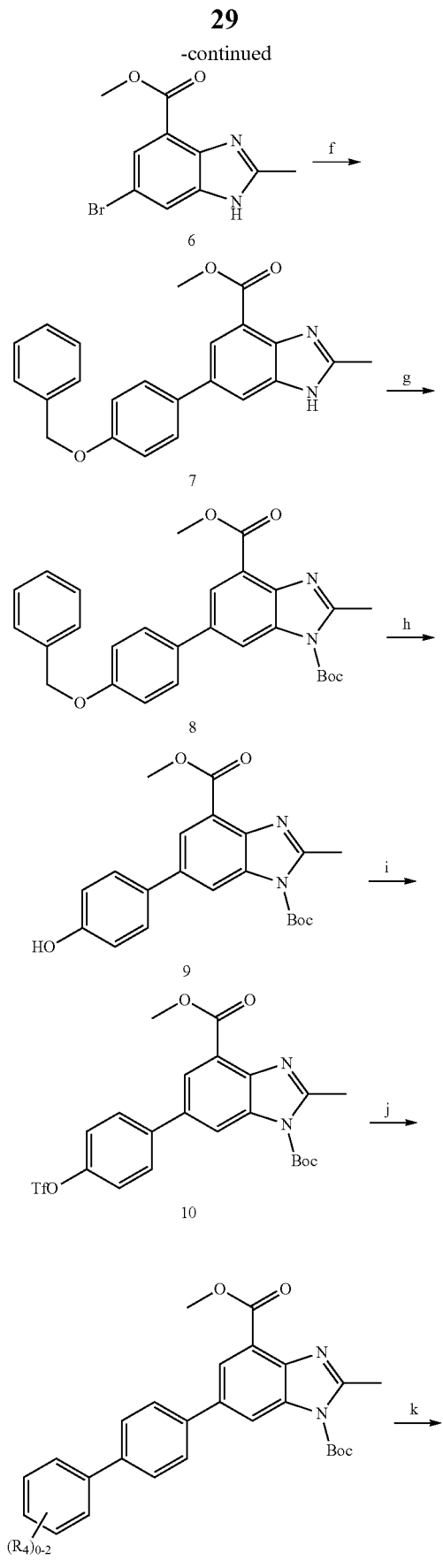

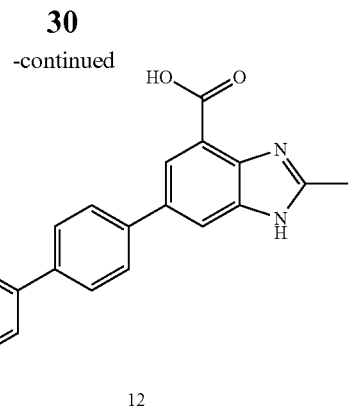

In step a, commercially available 5-bromo-1H-indole-2,3-dione is reacted with nitrating mixture to obtain 5-bromo-7-nitro-1H-indole-2,3-dione by following the procedure described in Preparation #1. In step b, 5-bromo-7-nitro-1H-indole-2,3-dione is reacted with hydrogen peroxide to afford 2-amino-5-bromo-3-nitro-benzoic acid by following the procedure described in Preparation #2, which is further reacted with methanol and Conc. $H_2SO_4$ to obtain 2-amino-5-bromo-3-nitrobenzoate by following the procedure described in Preparation #3. In step d, 2-amino-5-bromo-3-nitrobenzoate is reduced with Zinc dust/ammonium chloride to afford methyl 2,3-diamino-5-bromobenzoate by following the procedure described in Preparation #4. In step e, methyl 2,3-diamino-5-bromobenzoate is cyclized with acetic acid to afford methyl 6-bromo-2-methyl-1H-benzo[d]imidazole-4-carboxylate by following the procedure described in Preparation #5. In step f, 6-bromo-2-methyl-1H-benzo[d]imidazole-4-carboxylate is coupled with (4-(benzyloxy)phenyl)boronic acid using appropriate Palladium catalyst and following the procedure described in Preparation #6 to afford methyl 6-(4-(benzyloxy)phenyl)-2-methyl-1H-benzo[d]imidazole-4-carboxylate. In step g methyl 6-(4-(benzyloxy)phenyl)-2-methyl-1H-benzo[d]imidazole-4-carboxylate is protected with Boc anhydride by following the procedure described in Preparation #7 to afford 1-tert-butyl 4-methyl 6-(4-(benzyloxy)phenyl)-2-methyl-1H-benzo[d]imidazole-1,4-dicarboxylate and further in step h, it is de-benzylated using Hydrogenation by following the procedure described in Preparation #8 to afford 1-tert-butyl 4-methyl 6-(4-hydroxyphenyl)-2-methyl-1H-benzo[d]imidazole-1,4-dicarboxylate. In step i, 1-tert-butyl 4-methyl 6-(4-hydroxyphenyl)-2-methyl-1H-benzo[d]imidazole-1,4-dicarboxylate is reacted with trifluoro methane sulfonic anhydride to afford 1-tert-butyl 4-methyl 2-methyl-6-(4-(((trifluoromethyl)sulfonyl)oxy)phenyl)-1H-benzo[d]imidazole-1,4-dicarboxylate by following the procedure described in Preparation #9. In step j, 1-tert-butyl 4-methyl 2-methyl-6-(4-(((trifluoromethyl)sulfonyl)oxy)phenyl)-1H-benzo[d]imidazole-1,4-dicarboxylate is coupled with suitable phenyl boronic acids in presence of Palladium catalyst using General Procedure #A to afford compound #11, which is further subjected to base hydrolysis by following the procedure described in General procedure #E to afford the compounds of present invention.

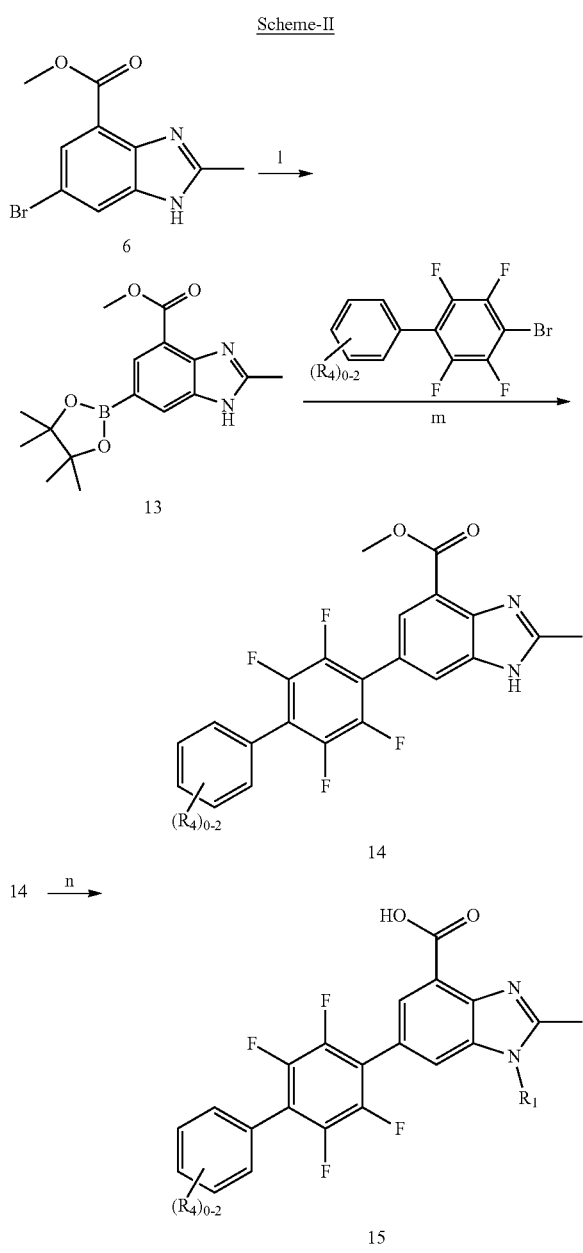

Scheme-II

In step 1, methyl 6-bromo-2-methyl-1H-benzo[d]imidazole-4-carboxylate is treated with bis (pinacolato)diboron in presence of suitable palladium catalyst by following the procedure described in Preparation #10 to afford methyl 2-methyl-6-(4,4,5,5-tetramethyl-1,3,2-dioxaborolan-2-yl)-1H-benzo[d]imidazole-4-carboxylate which further treated with suitable halo bi-phenyl derivatives in presence of suitable palladium catalyst by following the procedure described in General procedure A to afford compound #14. In step n, compound #14 is subjected to base hydrolysis by following the procedure described in General procedure #E afforded the compounds of present invention.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

EXAMPLES

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

General:

The HPLC data provided in the examples described below were obtained as followed.

Condition A: Column Waters Xbridge™ C8 50 mm×4.6 mm at a flow of 2 mL/min; 8 min gradient from 0.1% TFA in H2O to 0.07% TFA in CH3CN.

Condition B: C18 BDS (4.6×250) mm, SC\244 at a flow of 0.7 mL/min; 10 min gradient from 0.1% TFA in $H_2O$ to $CH_3CN$.

Preparative HPLC Conditions:

Column: Zorbax Eclipse XDB C18 PrepHT (150×21.2 mm, 5µ)

Mobile Phase: (A) 0.01% TFA or 0.1% TFA (B) ACN or ACN:MeOH (1:1)

Flow: 20 ml/min

The MS data provided in the examples described below were obtained as followed: Mass spectrum: LC/MS Waters ZMD (ESI) or a Waters Acquity SQD (ESI).

The NMR data provided in the examples described below were obtained as followed: $^1$H-NMR: Bruker DPX-300 MHz or a Bruker DPX 400 MHz.

The microwave chemistry was performed on a single mode microwave reactor Emrys™ Optimiser from Personal Chemistry.

Preparative HPLC purifications were performed with a mass directed autopurification Fractionlynx from Waters equipped with a Sunfire Prep C18 OBD column 19×100 mm 5 µm, unless otherwise reported. All HPLC purifications were performed with a gradient of ACN/$H_2O$ or ACN/$H_2O$/HCOOH (0.1%).

The compounds of invention have been named according to the standards used in the programACD/Name Batch from "Advanced Chemistry Development Inc., ACD/Labs (7.00 Release)". Product version: 7.10 build: 15 Sep. 2003.

The procedure for the compounds of Formula (I) are detailed herein below list of general procedures including the general synthesis of various intermediates involved in process of manufacture of the compounds according to the present invention.

LIST OF GENERAL PROCEDURES

General Procedure A: Suzuki Reaction
General Procedure B: Reductive Amination
General Procedure C: Oxidation of Sulphide Group
General Procedure D: O-Alkylation
General Procedure E: Formation of an Acid from Methyl Ester
General Procedure F: Amide Formation
General Procedure G: Preparation of 2,2,2-Trifluoroacetic Acid Salt Preparation #1:
5-bromo-7-nitro-1H-indole-2,3-dione

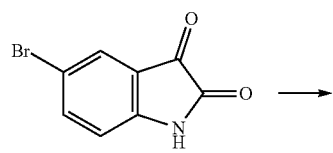

A stirred solution of 5-bromo-1H-indole-2, 3-dione (5 g, 22.1 mmol) in conc. $H_2SO_4$ (22.5 mL) was cooled to −5° C. and conc. nitric acid (1.45 mL) was added drop wise over 30 min and continued the stirring at the same temperature for 30 min. The progress of the reaction was monitored by TLC. The reaction mixture was poured slowly into the crushed ice. The yellow solid formed was filtered and dried under vacuum to obtain title compound as a yellow solid (5.5 g, 91.8%). $^1$H NMR (300 MHz, DMSO-$d_6$): δ 11.8 (s, 1H), 8.4 (s, 1H), 8.1 (s, 1H).

Preparation #2: 2-amino-5-bromo-3-nitro-benzoic Acid

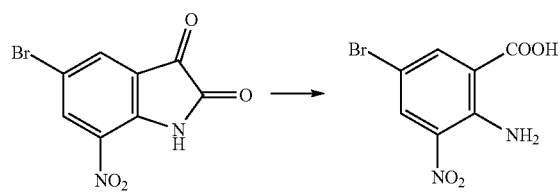 [SMILES: O=C1Nc2c(cc(Br)cc2[N+](=O)[O-])C1=O ; Nc1c(C(=O)O)cc(Br)cc1[N+](=O)[O-]]

To a stirred solution of 5-bromo-7-nitro-1H-indole-2,3-dione (5.5 g, 20.3 mmol) in an aq. solution of 2N NaOH (23.2 mL) was added a 50% solution of $H_2O_2$ in water (4.96 mL) slowly at 0° C. Then allowed to warm to room temperature and stirred for 4 h. The progress of the reaction was monitored by TLC and the reaction mixture was diluted with water and acidified with citric acid to pH-4. The yellow solid formed was filtered and dried under vacuum to get the title compound (5.0 g, 96.0%). $^1$H NMR (400 MHz, DMSO-$d_6$): δ 8.84 (bs, 2H), 8.59 (s, 1H), 8.37 (s, 1H).

Preparation #3: 2-amino-5-bromo-3-nitro-benzoic Acid methyl ester

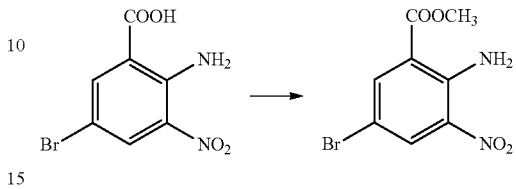

To a stirred solution of 2-amino-5-bromo-3-nitro-benzoic acid (5.0 g, 19.2 mmol) in methanol (250 mL) at 0° C. was added Conc. $H_2SO_4$ (50 mL) over 45 min. The reaction mixture was stirred at 90° C. for 8 h. The progress of the reaction was monitored by TLC. Methanol was distilled under vacuum and the resulting product was filtered and dried under vacuum. The title compound obtained as a yellow solid (5.0 g, 96.1%). $^1$H NMR (400 MHz, DMSO-$d_6$): δ 8.43 (s, 1H), 8.35 (bs, 2H), 8.25 (s, 1H), 3.9 (s, 3H).

Preparation #4: 2, 3-diamino-5-bromo benzoic Acid methyl ester

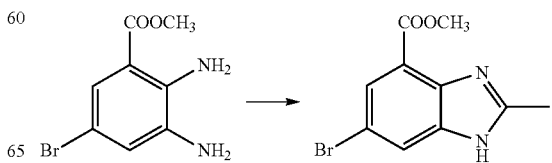

To a stirred solution of 2-amino-5-bromo-3-nitro-benzoic acid methyl ester (5.0 g, 18.2 mmol) in THF/Water (300/100 mL) was added zinc dust (8.12 g, 12.5 mmol) followed by ammonium chloride (13.25 g, 25.0 mmol) at room temperature. Then the reaction mixture allowed to stir at room temperature for 1 h. The progress of the reaction was monitored by TLC. The reaction mixture was filtered through celite and separated both the layers. The aqueous layer was extracted with ethyl acetate. The combined organic layer was dried over sodium sulphate and concentrated under reduced pressure to get the title compound as an ash colored solid (3.8 g, 85.4%). $^1$H NMR (300 MHz, DMSO-$d_6$): δ 7.2 (s, 1H), 6.9 (s, 1H), 6.4 (bs, 2H), 5.2 (bs, 2H), 3.9 (s, 3H).

Preparation #5:
6-bromo-2-methyl-1H-benzoimidazole-4-carboxylic Acid methyl ester To a stirred solution of 2,3-diamino-5-bromo-benzoic acid methyl ester (3.8 g, 15.5 mmol) in acetic acid (20 mL) was added triethyl amine (1 mL) and the reaction mixture was stirred at 110° C. for 8 h. The completion of the reaction was monitored by TLC. The acetic acid was distilled completely under reduced pressure. The resulting residue was dissolved in ethyl acetate and washed with water, dried over sodium sulphate and concentrated under reduced pressure to get the title compound as a white solid (3.25 g, 79.2%). $^1$H NMR (300 MHz, DMSO-$d_6$): δ 12.4 (bs, 1H), 8.0 (s, 1H), 7.8 (s, 1H), 4.0 (s, 3H), 2.6 (s, 3H).

Preparation #6: 6-(4-benzyloxy-phenyl)-2-methyl-1H-benzoimidazole-4-carboxylic Acid methyl ester

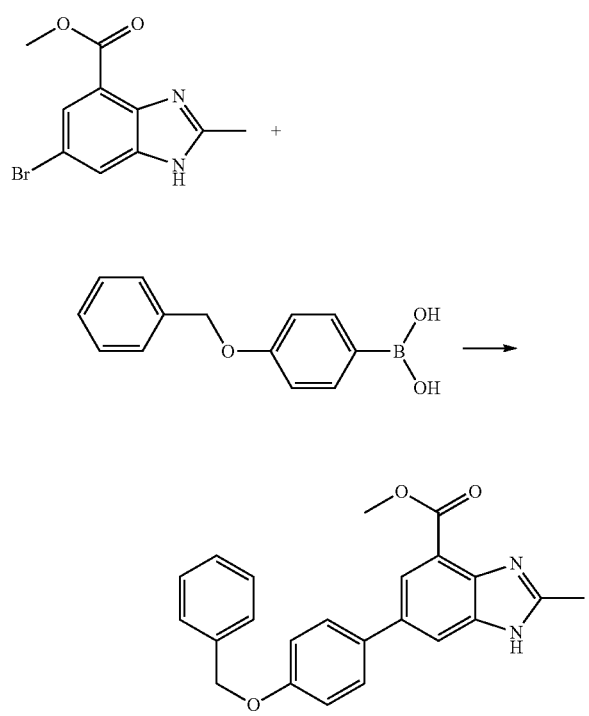

A mixture of toluene (120 mL) and water (30 mL) was degassed with nitrogen for 10 min. Sodium carbonate (5.9 g, 55.76 mmol) was added followed by 6-bromo-2-methyl-1H-benzoimidazole-4-carboxylic acid methyl ester (5.0 g, 18.58 mmol) and 4-benzyloxy phenyl boronic acid (4.23 g, 18.58 mmol) again degassed for 15 min. Finally the Tetrakis (triphenylphosphine)palladium(0) (2.15 g, 1.85 mmol) was added. The reaction mixture was stirred at reflux temperature for 3 h under nitrogen atmosphere. The progress of the reaction was monitored by TLC. The reaction mixture was extracted with ethyl acetate. The ethyl acetate layer was washed with water, dried over sodium sulphate and concentrated under reduced pressure to obtain the crude compound. The crude compound was purified by column chromatography using ethyl acetate to get the desired compound as an off white solid. (3.6 g, 52%). $^1$H NMR (400 MHz, DMSO-$d_6$): δ 12.2 (bs, 1H), 8.0 (s, 1H), 7.9 (s, 1H), 7.64-7.62 (d, J=8.0 Hz, 2H), 7.60-7.68 (m, 2H), 7.30-7.44 (m, 3H), 7.12-7.10 (d, J=8.8 Hz, 2H), 5.2 (s, 2H), 4.0 (s, 3H), 2.6 (s, 3H).

Preparation #7: 6-(4-benzyloxy-phenyl)-2-methyl-benzoimidazole-1, 4-dicarboxylic Acid 1-tert-butyl ester 4-methyl ester

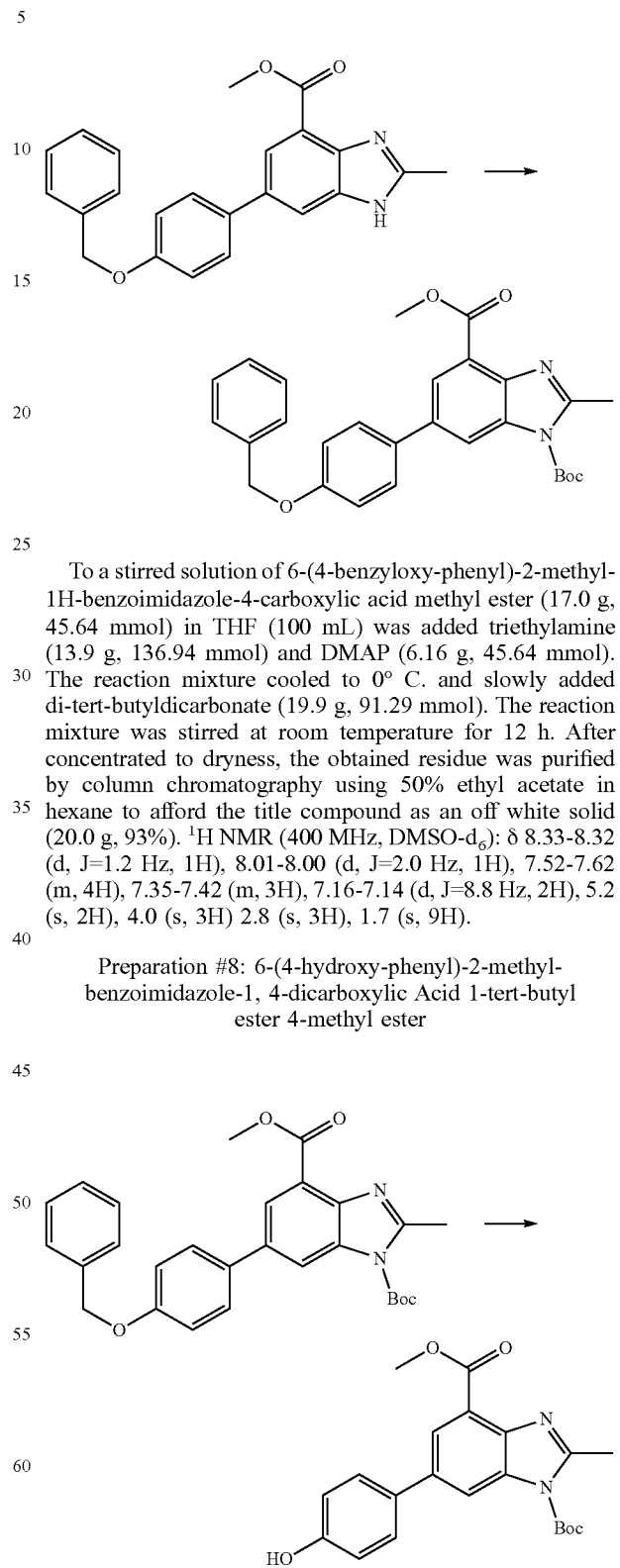

To a stirred solution of 6-(4-benzyloxy-phenyl)-2-methyl-1H-benzoimidazole-4-carboxylic acid methyl ester (17.0 g, 45.64 mmol) in THF (100 mL) was added triethylamine (13.9 g, 136.94 mmol) and DMAP (6.16 g, 45.64 mmol). The reaction mixture cooled to 0° C. and slowly added di-tert-butyldicarbonate (19.9 g, 91.29 mmol). The reaction mixture was stirred at room temperature for 12 h. After concentrated to dryness, the obtained residue was purified by column chromatography using 50% ethyl acetate in hexane to afford the title compound as an off white solid (20.0 g, 93%). $^1$H NMR (400 MHz, DMSO-$d_6$): δ 8.33-8.32 (d, J=1.2 Hz, 1H), 8.01-8.00 (d, J=2.0 Hz, 1H), 7.52-7.62 (m, 4H), 7.35-7.42 (m, 3H), 7.16-7.14 (d, J=8.8 Hz, 2H), 5.2 (s, 2H), 4.0 (s, 3H) 2.8 (s, 3H), 1.7 (s, 9H).

Preparation #8: 6-(4-hydroxy-phenyl)-2-methyl-benzoimidazole-1, 4-dicarboxylic Acid 1-tert-butyl ester 4-methyl ester To a stirred solution of 6-(4-benzyloxy-phenyl)-2-methyl-benzoimidazole-1,4-dicarboxylic acid 1-tert-butyl ester 4-methyl ester (9.0 g, 19.05 mmol) in methanol (80 mL) was added a slurry of Pd/C (0.9 g, 10%) in methanol (10 mL). The reaction mixture was hydrogenated for 12 h with a hydrogen balloon. After completion of the reaction the reaction mixture then filtered on celite and the cake was washed with methanol (50 mL). The filtrate was concentrated to dryness to get title compound as an off white solid (6.5 g, 89%). $^1$H NMR (400 MHz, DMSO-d$_6$): δ 9.7 (bs, 1H), 8.3 (s, 1H), 8.0 (s, 1H), 7.5 (m, 2H), 6.9 (d, 2H), 4.0 (s, 3H), 2.8 (s, 3H), 1.8 (s, 9H).

Preparation #9: 2-methyl-6-(4-trifluoromethane-sulfonyloxy-phenyl)-benzo imidazole-1,4-dicarboxylic Acid 1-tert-butyl ester 4-methyl ester

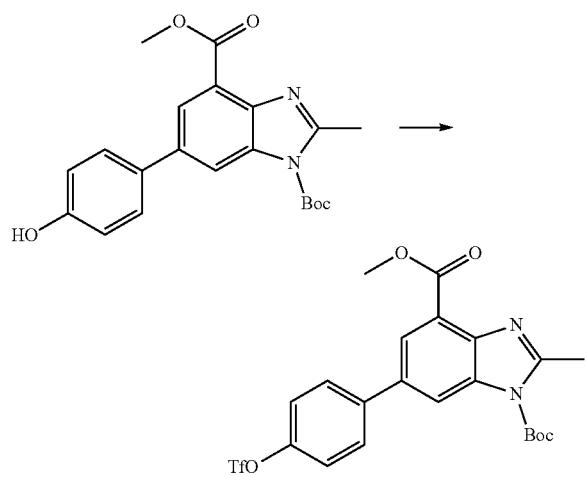

To a stirred solution of 6-(4-hydroxy-phenyl)-2-methyl-benzoimidazole-1, 4-dicarboxylic acid 1-tert-butyl ester 4-methyl ester (13.0 g, 33.81 mmol) in DCM (100 mL) was added DIPEA (21.8 g, 169.05 mmol) and cooled to −70° C. Trifluoroacetic anhydride (10.49 g, 37.2 mmol) was added drop wise over 10 min. The reaction mixture was stirred at room temperature for 12 h. The completion of the reaction was monitored by TLC. Reaction mixture was diluted with DCM and washed with water. The organic layer was dried over anhydrous sodium sulphate and concentrated under reduced pressure to get the title compound as an off white solid (16.0 g, 92%). $^1$H NMR (400 MHz, CDCl$_3$): δ 8.42 (d, J=1.6 Hz, 1H), 8.19-8.18 (d, J=2.0 Hz, 1H), 7.74-7.73 (d, J=2.0 Hz, 2H), 7.39-7.37 (d, J=8.8 Hz, 2H), 4.0 (s, 3H), 2.9 (s, 3H), 1.8 (s, 9H).

Preparation #10: 2-methyl-6-(4, 4, 5, 5-tetramethyl-[1, 3, 2] dioxaborolan-2-yl)-1H-benzoimidazole-4-carboxylic Acid methyl ester

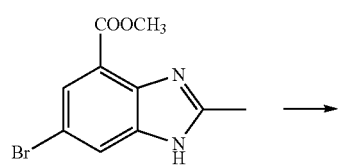

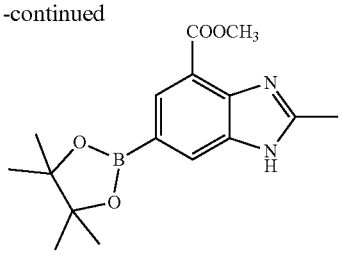

The slurry of potassium acetate (3.26 g, 33.3 mmol) in 1, 4-dioxane was degassed with nitrogen for 15 min. 6-bromo-2-methyl-1H-benzoimidazole-4-carboxylic acid methyl ester (3 g, 11.1 mmol) was added followed by bis(pinacolato)diboron (3.12 g, 12.3 mmol) and degassed again for 15 min. Finally [1,1'-Bis(diphenylphosphino)ferrocene]palladium(II) dichloride (0.452 g, 0.55 mmol) was added. The reaction mixture was stirred at 80° C. for 8 h under nitrogen atmosphere. The progress of the reaction was monitored by TLC. 1,4-dioxane was removed under vacuum and the obtained residue was dissolved in ethyl acetate, washed with water. The organic layer was dried over sodium sulphate and concentrated under vacuum to get the title compound as a black oily liquid (3 g, crude). Crude compound was directly used for the next step without any purification. $^1$H NMR (300 MHz, CDCl$_3$): δ 10.1 (bs, 1H), 8.4 (s, 1H), 8.3 (s, 1H), 4.0 (s, 3H), 2.6 (s, 3H), 1.4 (s, 12H).

Preparation #11: (4'-bromo-2',3',5',6'-tetrafluoro-[1, 1'-biphenyl]-4-yl)(methyl)sulfane

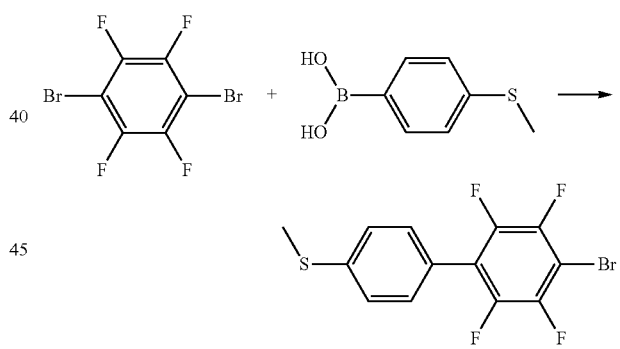

A mixture of toluene (150 mL) and water (50 mL) was degassed with nitrogen for 15 min. Cesium carbonate (4.23 g, 12.98 mmol) was added followed by 1,4-dibromo-2,3,5, 6-tetrafluorobenzene (2.0 g, 6.49 mmol) and (4-(methylthio)phenyl)boronic acid (0.545 g, 3.24 mmol), again degassed for 15 min. [1,1'-Bis(diphenylphosphino)ferrocene]palladium(II) dichloride (0.529 g, 0.64 mmol) was added. The reaction mixture was stirred at reflux temperature for 2 h under nitrogen atmosphere. The progress of the reaction was monitored by TLC. After completion the reaction, the reaction mixture was extracted with ethyl acetate. The ethyl acetate layer was washed with water, dried over sodium sulphate and concentrated to obtain the crude compound. The crude compound was purified by column chromatography using 10% ethyl acetate in hexane to get the title compound as a white solid (0.4 g, 17%). $^1$H NMR (300 MHz, CDCl$_3$): δ=7.22-7.40 (m, 4H), 2.6 (s, 3H).

General Procedure A: Suzuki Reaction
Method 1:

A mixture of toluene and water (8:2 mixture) is degased with nitrogen for about 10 to 15 min then added suitable base (such as Na$_2$CO$_3$ or K$_2$CO$_3$ or Cs$_2$CO$_3$ preferably Na$_2$CO$_3$) followed by 2-methyl-6-(4-trifluoromethanesulfonyloxy-phenyl)-benzoimidazole-1,4-dicarboxylic acid 1-tert butylester 4-methylester (1.0 to 3.0 equiv, preferably 1.0 equiv) and appropriate boronic acid (1.0 to 3.0 equiv, preferably 1.5 equivalent). The reaction mixture is again degassed for 15 min and finally added [1,1'-Bis(diphenylphosphino)ferrocene]palladium(II) dichloride (0.001 to 0.010 equivalent, preferably 0.05 equivalent) is added. The reaction mixture is stirred at reflux temperature under nitrogen for about 3 h to 12 h (preferably about 4 h). The reaction mixture is cooled to room temperature and evaporated to dryness under reduced pressure. The residue obtained was redissolved in EtOAc, washed successively with water and brine solution. The organic solution is dried over Na$_2$SO$_4$ or MgSO$_4$, filtered, and concentrated under reduced pressure. The product was purified by crystallization or trituration from an appropriate solvent or solvents or by preparative HPLC or flash chromatography.

Method 2:

A mixture of toluene and water (8:2 mixture) is degased with nitrogen for about 10 to 15 min then added suitable base (such as Na$_2$CO$_3$ or K$_2$CO$_3$ or Cs$_2$CO$_3$ preferably Cs$_2$CO$_3$) followed by appropriate aryl halo compound (1.0 to 3.0 equivalents, preferably 1.0 equivalents) and 2-methyl-6-(4-trifluoromethanesulfonyloxy-phenyl)-benzoimidazole-1, 4-dicarboxylic acid 1-tert-butyl ester 4-methyl ester (1.0 to 3.0 equivalents, preferably 1.5 equiv). The reaction mixture is again degassed for 15 min and finally added [1,1'-Bis(diphenylphosphino)ferrocene]palladium(II) dichloride (0.001 to 0.010 equivalents, preferably 0.05 equivalents) is added. The reaction mixture is stirred at reflux temperature under nitrogen for about 3 h to 12 h (preferably about 4 h). The reaction mixture is cooled to RT and evaporated to dryness under reduced pressure. The residue obtained was re-dissolved in EtOAc, washed successively with water and brine solution. The organic solution is dried over Na$_2$SO$_4$ or MgSO$_4$, filtered, and concentrated under reduced pressure. The product was purified by crystallization or trituration from an appropriate solvent or solvents or by preparative HPLC or flash chromatography.

Illustration of General Procedure #A

Preparation #12: Method 1: 1-(tert-butyl) 4-methyl 6-(3'-formyl-[1,1'-biphenyl]-4-yl)-2-methyl-1H-benzo[d]imidazole-1,4-dicarboxylate

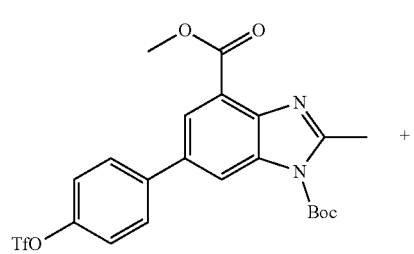

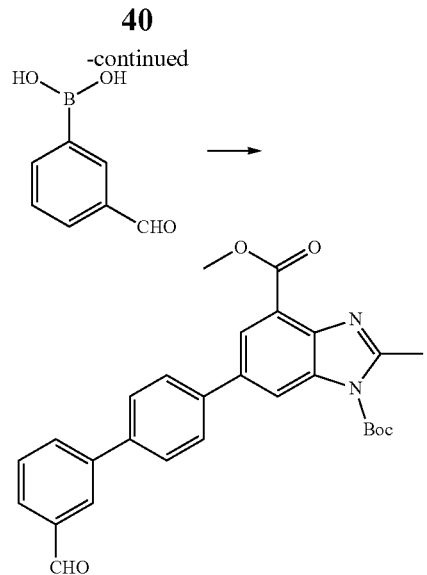

A mixture of toluene (80 mL) and water (20 mL) was degassed with nitrogen for 10 min. Sodium carbonate (0.927 g, 8.748 mmol) was added followed by 2-methyl-6-(4-trifluoromethanesulfonyloxy-phenyl)benzoimidazole-1,4-dicarboxylic acid 1-tert-butyl ester 4-methyl ester (1.5 g, 2.916 mmol) and (3-formylphenyl)boronic acid (0.656 g, 4.374 mmol, Aldrich). The reaction mixture was again degassed for 15 min. Finally the [1,1'-Bis(diphenylphosphino)ferrocene]palladium(II) dichloride (0.119 g, 0.145 mmol) was added. The reaction mixture was stirred at reflux temperature for 3 h under nitrogen. The progress of the reaction was monitored by TLC. The reaction mixture was cooled to room temperature and evaporated to dryness under reduced pressure. The residue obtained is re-dissolved in EtOAc, washed successively with water and brine solution. Ethyl acetate layer was dried over sodium sulphate and concentrated. The crude compound was purified by column chromatography using 50% ethyl acetate in hexane to get the desired compound. (0.8 g, 61.0%). $^1$H NMR (300 MHz, CDCl$_3$): δ 10.10 (s, 1H), 8.5 (s, 1H), 8.3 (s, 1H), 8.0 (m, 2H), 7.76-7.88 (m, 6H), 4.0 (s, 3H), 3.0 (s, 3H), 1.8 (s, 9H), Illustration of General Procedure #A: Method-2

Preparation #13: methyl 2-methyl-6-(2, 3, 5, 6-tetrafluoro-4'-(methylthio)-[1,1'-biphenyl]-4-yl)-1H-benzo[d]imidazole-4-carboxylate

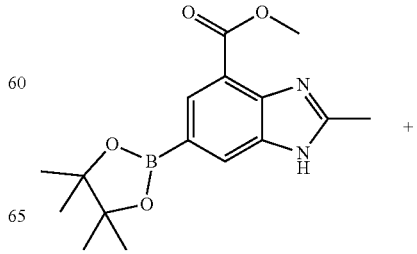

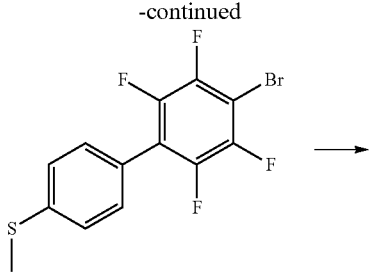

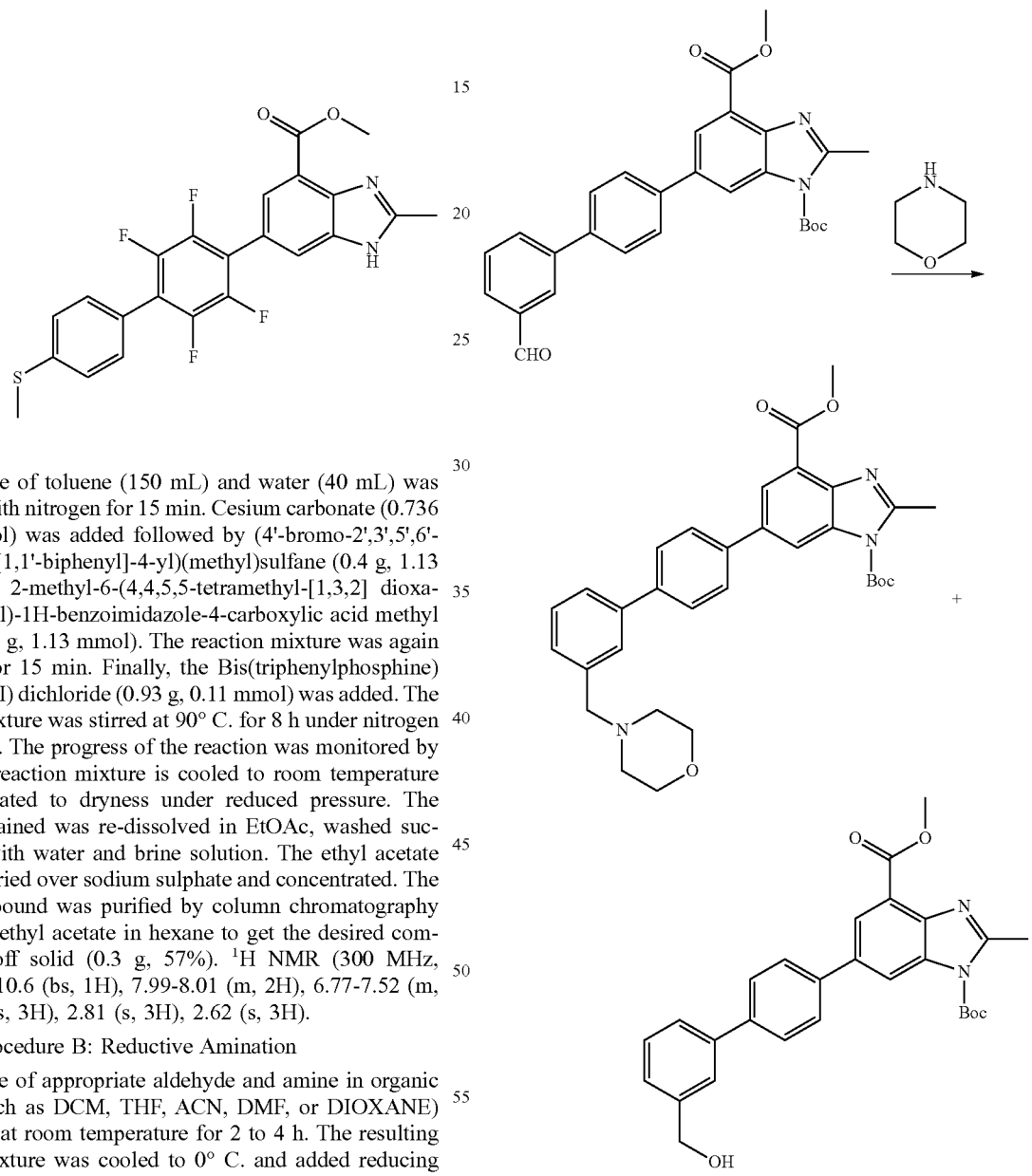

Illustration of General Procedure #B

Preparation #14 2-methyl-6-(3'-piperidin-1-ylm-ethyl-biphenyl-4-yl)-benzoimidazole-1, 4-dicarboxylic acid 1-tert-butyl ester 4-methyl ester & 1-tert-butyl 4-methyl 6-(3'-(hydroxymethyl)-[1,1'-biphenyl]-4-yl)-2-methyl-1H-benzo[d]imidazole-1, 4-dicarboxylate A mixture of toluene (150 mL) and water (40 mL) was degassed with nitrogen for 15 min. Cesium carbonate (0.736 g, 4.8 mmol) was added followed by (4'-bromo-2',3',5',6'-tetrafluoro-[1,1'-biphenyl]-4-yl)(methyl)sulfane (0.4 g, 1.13 mmol) and 2-methyl-6-(4,4,5,5-tetramethyl-[1,3,2] dioxaborolan-2-yl)-1H-benzoimidazole-4-carboxylic acid methyl ester (0.357 g, 1.13 mmol). The reaction mixture was again degassed for 15 min. Finally, the Bis(triphenylphosphine)palladium(II) dichloride (0.93 g, 0.11 mmol) was added. The reaction mixture was stirred at 90° C. for 8 h under nitrogen atmosphere. The progress of the reaction was monitored by TLC. The reaction mixture is cooled to room temperature and evaporated to dryness under reduced pressure. The residue obtained was re-dissolved in EtOAc, washed successively with water and brine solution. The ethyl acetate layer was dried over sodium sulphate and concentrated. The crude compound was purified by column chromatography using 80% ethyl acetate in hexane to get the desired compound as off solid (0.3 g, 57%). $^1$H NMR (300 MHz, CDCl$_3$): δ 10.6 (bs, 1H), 7.99-8.01 (m, 2H), 6.77-7.52 (m, 4H), 4.01 (s, 3H), 2.81 (s, 3H), 2.62 (s, 3H).

General Procedure B: Reductive Amination

A mixture of appropriate aldehyde and amine in organic solvent (such as DCM, THF, ACN, DMF, or DIOXANE) was stirred at room temperature for 2 to 4 h. The resulting reaction mixture was cooled to 0° C. and added reducing agent sodium triacetoxyborohydride in small portions. The resulting reaction mixture was stirred at room temperature for 2-4 h. The progress of the reaction was monitored by TLC, and the reaction mixture was quenched with an aq. solution of sodium bicarbonate. Further it was extracted with ethyl acetate and the combined organic layer was dried over sodium sulphate and concentrated under vacuum. The residue obtained was taken to the next step without any purification.

A solution of 6-(3'-formyl-biphenyl-4-yl)-2-methyl-benzoimidazole-1,4 dicarboxylic acid 1-tert-butyl ester 4-methyl ester (0.35 g, 0.744 mmol) and piperidine (0.063 g, 0.744 mmol) in THF (15 mL) was stirred for 30 min at room temperature. The reaction mixture was cooled to 0° C., added sodium triacetoxy borohydride (0.946 g, 4.464 mmol) and was stirred for 2 h at room temperature. The progress of the reaction was monitored by TLC, and the reaction mixture was quenched with an aq. solution of sodium bicarbonate (50 mL). It was extracted with ethyl acetate (3×50 mL) and the combined organic layer was dried over sodium sulphate and concentrated under reduced pressure. The obtained residue (0.15 g, 37.4%) was taken to next step without any purification.

General Procedure C: Oxidation of Sulphide Group

To a flask containing methyl thio compound in acetic acid is added sodium tungstate, (0.1-0.05 equiv, preferably 0.05 equiv) followed by peroxide (such as hydrogen peroxide, meta-Chloroperoxybenzoic acid, preferably hydrogen peroxide). The resulting reaction mixture is stirred at room temperature for 2-4 h. Reaction mixture was quenched with aq. sodium sulphite solution and stirred for 30 min. Aqueous layer was extracted with EtOAc. The organic layer was washed with water, brine, dried over $Na_2SO_4$ or $MgSO_4$, filtered and concentrated under reduced pressure. The residue obtained was taken to next step without any purification.

Illustration of General Procedure #C

Preparation #15: methyl 2-methyl-6-(2,3,5,6-tetrafluoro-4'-(methylsulfonyl)-[1,1'-biphenyl]-4-yl)-1H-benzo[d]imidazole-4-carboxylate trated under reduced pressure. The residue obtained (0.180 g) was taken to next step without any purification.

General Procedure D: O-Alkylation

To a flask containing phenolic derivative in organic solvent (such as DMF, DCM, THF, $CHCl_3$, preferably DMF) was added inorganic base such as (potassium carbonate, sodium carbonate, cesium carbonate, preferably potassium carbonate, 1-3 equivalents). After stirring for about 10 min at room temperature, the appropriate mesyl derivative (1.2 equivalents) was added and the reaction was stirred at 110° C. for 8-12 h, preferably 12 h. The reaction mixture is cooled to room temperature and poured into ice cold water the product was extracted with EtOAc. The organic layer was dried over sodium sulphate and concentrated under reduced pressure. The residue obtained was taken to next step without any purification.

Illustration of General Procedure #D

Preparation #16: 2-methyl-6-(3'-(2-morpholinoethoxy)-[1,1'-biphenyl]-4-yl)-1H-benzo[d]imidazole-4-carboxylic Acid

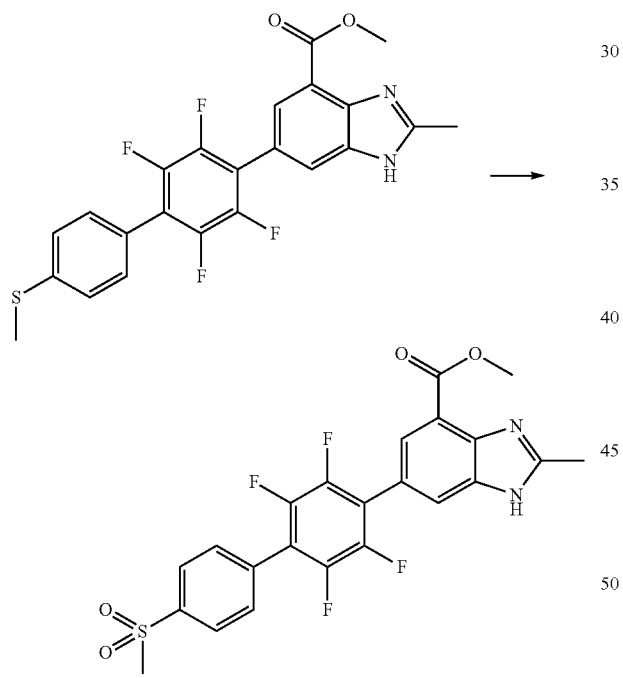

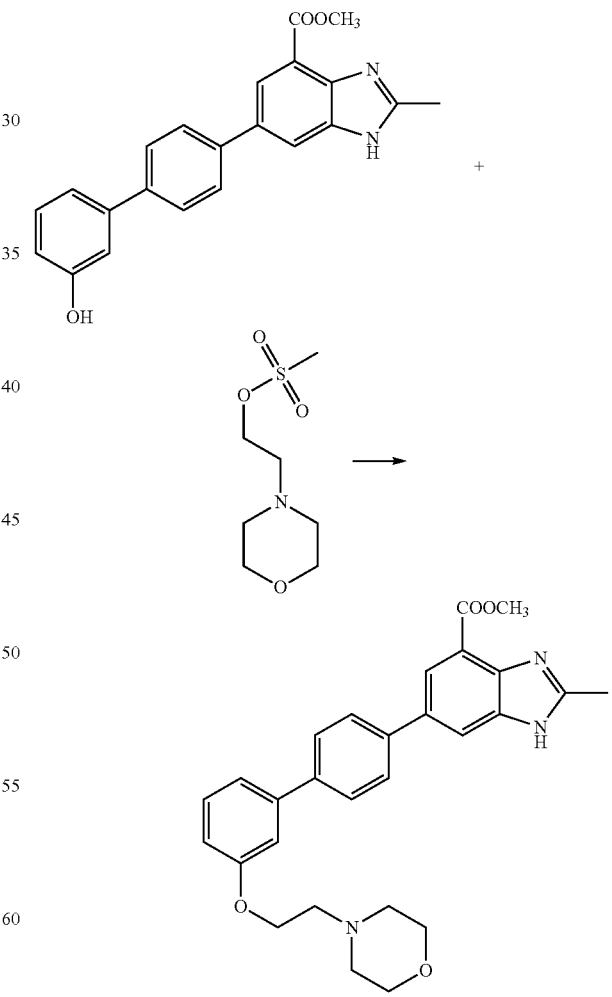

To a stirred solution of methyl 2-methyl-6-(2,3,5,6-tetrafluoro-4'-(methylthio)-[1,1'-biphenyl]-4-yl)-1H-benzo[d]imidazole-4-carboxylate (0.150 g, 0.32 mmol) in acetic acid (10 mL) was added sodium tungstate (0.021 g 0.065 mmol), and 50% solution of $H_2O_2$ in water (0.2 mL) slowly at room temperature. The reaction mixture was stirred at room temperature for 2 h. The progress of the reaction was monitored by TLC. Reaction mixture was quenched with aqueous sodium sulphite solution (50 mL) and stirred for 30 min. The aqueous layer was extracted with EtOAc (3×30 mL), The combined organic layer was washed with water, brine, dried over $Na_2SO_4$ or $MgSO_4$, filtered, and concen- To a solution of methyl 6-(3'-hydroxy-[1,1'-biphenyl]-4-yl)-2-methyl-1H-benzo[d]imidazole-4-carboxylate (0.5 g, 1.09 mmol) in DMF (10 mL) was added potassium carbonate (0.45 g, 3.27 mmol) followed by 2-morpholinoethyl methanesulfonate (0.274 g, 1.31 mmol). The reaction mixture was stirred at 100° C. for about 12 h and was poured into ice cold water (30 mL). The product was extracted with EtOAc (3×50 mL). The combined organic layer was dried over sodium sulphate and evaporated under reduced pressure. The residue obtained (0.4 g) was taken to next step without any purification.

General Procedure E: Formation of an Acid from Methyl Ester

To a flask containing an appropriate alkyl ester in an aqueous organic solvent (such as THF or methanol) was added 1.5-equivalents of aqueous sodium hydroxide solution and the reaction mixture was refluxed for 8 h. The reaction was monitored by TLC. Excess solvent is removed under vacuum and the solution is acidified with 10% HCl solution. The precipitated solid was collected by filtration and dried under vacuum to obtain the target carboxylic acid derivative. The crude material is optionally purified by precipitation, crystallization or trituration from an appropriate solvent or solvents or column chromatography or by preparative HPLC to give the target compound.

Illustration of General Procedure #E: 6-biphenyl-4-yl-2-methyl-1H-benzoimidazole-4-carboxylic Acid N-ethyl-N-isopropylpropan-2-amine (1.2 equivalents). After stirring for about 10 min at approximately 25° C., the appropriate amine (1.2 equivalents) is added and the reaction was stirred for an additional 8-12 h, preferably 12 h. Water was added to the reaction mixture, the precipitated solid was collected by filtration and dried under vacuum to obtain the Amide derivative.

Illustration of General Procedure F

Preparation #17: 1-tert-butyl 4-methyl 6-(3'-(1-(tert-butoxycarbonyl)pyrrolidine-2-carboxamido)-[1,1'-biphenyl]-4-yl)-2-methyl-1H-benzo[d]imidazole-1,4-dicarboxylate

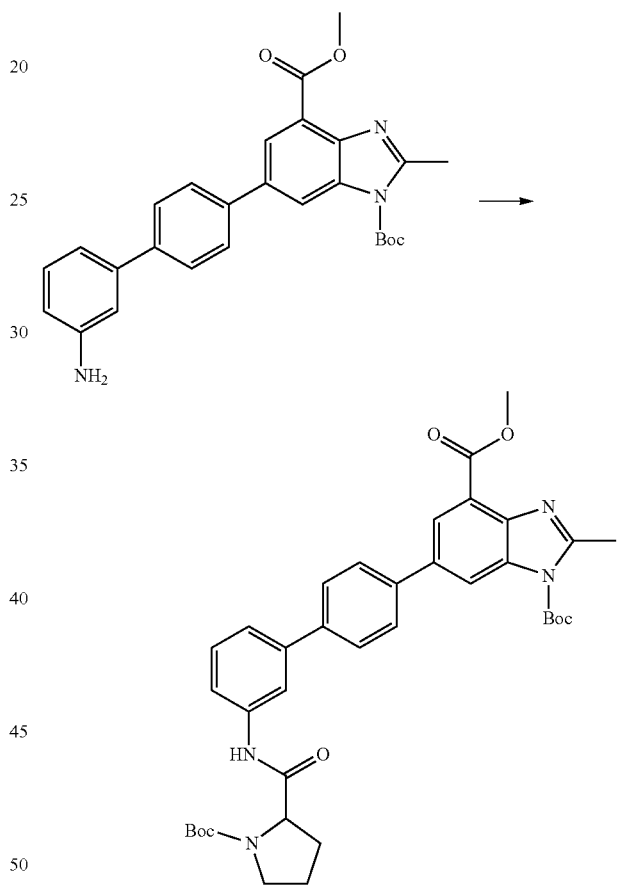

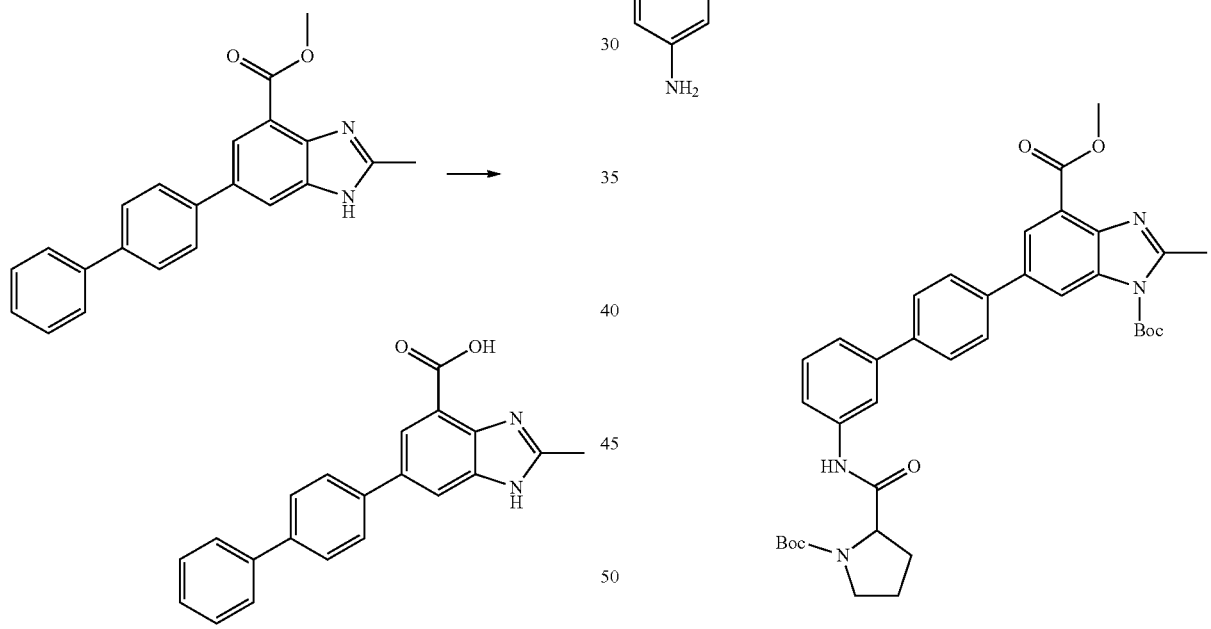

To a solution of 6-biphenyl-4-yl-2-methyl-1H-benzoimidazole-4-carboxylic acid methyl ester (0.650 g, 1.89 mmol) in a mixture of THF/Water (24/8 mL) was added an aqueous 5N NaOH (10 mL). The reaction mixture was refluxed for 8 h. Completion of the reaction was monitored by TLC. The reaction mixture was concentrated, and the aqueous layer was cooled and acidified with 2N HCl to pH-2. The solid precipitated was filtered and dried under vacuum to get the title compound as a brick red solid (0.550 g, 88.7%). HPLC purity: 95.80%, LCMS m/e (M+1): 99.78%.

General Procedure F: Amide Formation

To a flask containing appropriate carboxylic acid derivative (1.0 equivalents) in an organic solvent (such as DMF, DMA or $CH_2Cl_2$) is added HATU (1.2 equivalents) and To a flask containing a 1-(tert-butoxycarbonyl)pyrrolidine-2-carboxylic acid (0.117 g, 5.4 mmol) in DMF (10 mL) was added HATU (0.311 g, 8.1 mmol) and N-ethyl-N-isopropylpropan-2-amine (1.0 mL). The mixture was stirred at about 25° C. for 10 min and was added 1-tert-butyl 4-methyl 6-(3'-amino-[1,1'-biphenyl]-4-yl)-2-methyl-1H-benzo[d]imidazole-1,4-dicarboxylate (0.250 g, 5.4 mmol). The reaction was then stirred at about 25° C. for 12 h. Water (50 mL) was added to the reaction mixture, The precipitated product was collected by filtration and dried under vacuum to obtained the desired compound as an off white solid (0.230 g, 64%). $^1$H NMR (300 MHz, $CDCl_3$): δ 9.81 (bs, 1H), 8.48 (s, 1H), 8.37 (s, 1H), 7.75-7.67 (m, 4H), 7.49-7.37 (m, 3H), 4.51-4.49 (m, 1H), 4.05 (s, 3H), 3.49-3.41 (m, 3H), 2.82 (s, 3H), 1.95 (m, 3H), 1.75 (s, 9H), 1.51 (s, 9H).

General Procedure G: Benzo Imidazole Carbolic Acid 2, 2, 2-Trifluoroacetic Acid Salt Crude compound of (obtained from General procedure E) can be purified by preparative HPLC using the condition.

Column: Zorbax Eclipse XDB C18 PrepHT (150×21.2 mm, 5µ).

Mobile Phase: (A) 0.1% TFA. (B) ACN:MeOH (1:1),

Flow: 20 ml/min.

Compound fractions are concentrated to get the desired Benzo imidazole carbolic acid 2, 2, 2-trifluoroacetic acid salt compounds.

TABLE II

| Example No | Structure | General Procedure | Analytical data |
|---|---|---|---|
| 1 | 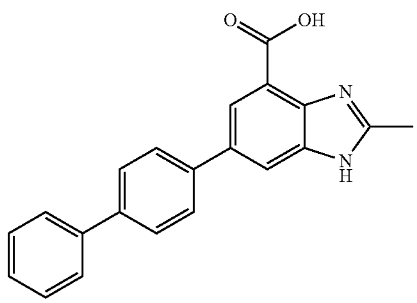 [SMILES: Cc1nc2c(C(=O)O)cc(-c3ccc(-c4ccccc4)cc3)cc2[nH]1] | A-1 & E | $^1$H NMR (300 MHz, DMSO-d$_6$): δ 14.20 (bs, 1H), 8.28-8.30 (m, 2H), 7.82-7.90 (m, 4H), 7.73-7.76 (m, 2H), 7.48-7.53 (m, 2H), 7.40-7.43 (m, 1H), 2.86 (s, 3H). (1H-Not revealed by $^1$H NMR). MS m/z = 328.9 (M + H)$^+$. |
| 2 | 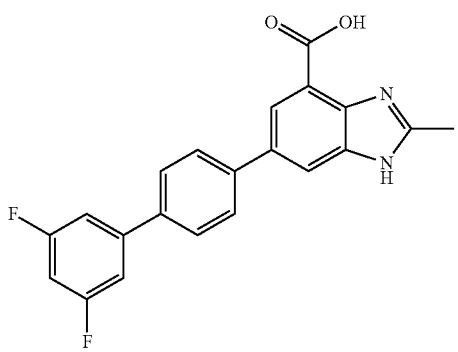 [SMILES: Cc1nc2c(C(=O)O)cc(-c3ccc(-c4cc(F)cc(F)c4)cc3)cc2[nH]1] | A-1 & E | $^1$H NMR (300 MHz, DMSO-d$_6$): δ 14.20 (bs, 1H), 8.28 (s, 2H), 7.84-7.98 (m, 4H), 7.52-7.55 (m, 2H), 7.24-7.30 (m, 1H), 2.85 (s, 3H). MS m/z = 363 (M − H)$^-$ |
| 3 | 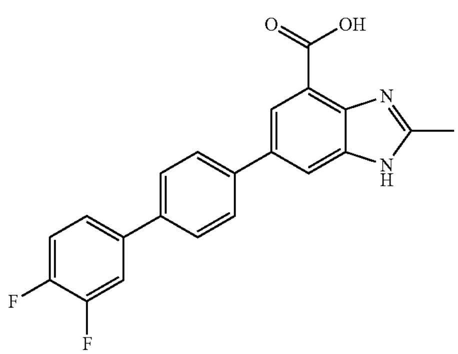 [SMILES: Cc1nc2c(C(=O)O)cc(-c3ccc(-c4ccc(F)c(F)c4)cc3)cc2[nH]1] | A-1 & E | $^1$H NMR (300 MHz, DMSO-d$_6$): δ 14.20 (bs, 1H), 8.20-8.36 (m, 2H), 7.80-7.98 (m, 5H), 7.57-7.61 (m, 3H), 2.83 (s, 3H). MS m/z = 362.9 (M − H)$^-$ |
| 4 | 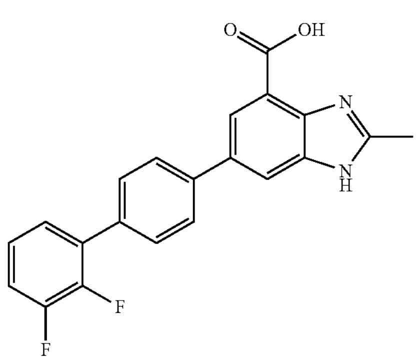 [SMILES: Cc1nc2c(C(=O)O)cc(-c3ccc(-c4cccc(F)c4F)cc3)cc2[nH]1] | A-1 & E | $^1$H NMR (300 MHz, DMSO-d$_6$): δ 13.80 (bs, 1H), 8.22 (d, J = 0.9 Hz, 2H), 8.0-7.85 (m, 2H), 7.80-7.68 (m, 2H), 7.58-7.26 (m, 3H), 2.80 (s, 3H). MS m/z = 365 (M + H)$^+$ |

TABLE II-continued

| Example No | Structure | General Procedure | Analytical data |
|---|---|---|---|
| 5 | 6-(2'-fluorobiphenyl-4-yl)-2-methyl-1H-benzimidazole-4-carboxylic acid | A-1 & E | $^1$H NMR (300 MHz, DMSO-d$_6$): δ 14.00 (bs, 1H), 8.26 (s, 2H), 7.90 (d, J = 7.8 Hz, 2H), 7.66-7.58 (m, 1H), 7.71 (d, J = 7.8 Hz, 2H), 7.52-7.42 (m, 1H), 7.40-7.30 (m, 2H), 2.80 (s, 3H). MS m/z = 347 (M + H)$^+$ |
| 6 | 6-(4'-fluorobiphenyl-4-yl)-2-methyl-1H-benzimidazole-4-carboxylic acid | A-1 & E | $^1$H NMR (300 MHz, DMSO-d$_6$): δ 14.20 (bs, 1H), 8.28 (s, 2H), 8.20-7.76 (m, 6H), 7.33 (m, 2H), 2.80 (s, 3H). MS m/z = 347 (M + H)$^+$ |
| 7 | 2-methyl-6-(4-(pyridin-3-yl)phenyl)-1H-benzimidazole-4-carboxylic acid | A-1 & E | $^1$H NMR (300 MHz, DMSO-d$_6$): δ 14.20 (s, 1H), 9.20 (bs, 1H), 8.8 (d, J = 6 Hz, 1H), 8.6 (d, J = 6 Hz, 1H), 8.32 (s, 2H), 8.0 (m, 4H), 7.85 (m, 2H), 2.87 (s, 3H). MS m/z = 327.8 (M − H)$^-$ |
| 8 | 6-(3'-fluorobiphenyl-4-yl)-2-methyl-1H-benzimidazole-4-carboxylic acid | A-1 & E | $^1$H NMR (300 MHz, DMSO-d$_6$): δ 13.80 (bs, 1H), 8.16-8.24 (m, 2H), 7.82-7.90 (m, 4H), 7.50-7.64 (m, 3H), 7.15-7.30 (m, 1H), 2.65 (s, 3H). MS m/z = 346.9 (M + H)$^+$ |
| 9 | 2-methyl-6-(4-(pyridin-4-yl)phenyl)-1H-benzimidazole-4-carboxylic acid | A-1 & E | $^1$H NMR (300 MHz, DMSO-d$_6$): δ 8.86 (s, 2H), 8.30-8.35 (m, 2H), 8.00-8.19 (m, 6H), 2.82 (s, 3H). (2H-Not revealed by $^1$H NMR). MS m/z = 329.9 (M + H)$^+$ |

TABLE II-continued

| Example No | Structure | General Procedure | Analytical data |
|---|---|---|---|
| 10 | 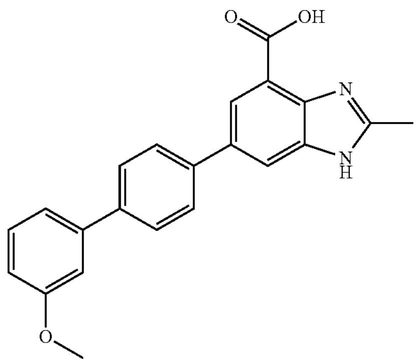 [SMILES: COc1cccc(-c2ccc(-c3cc(C(=O)O)c4nc(C)[nH]c4c3)cc2)c1] | A-1 & E | $^1$H NMR (300 MHz, DMSO-d$_6$): δ 14.00 (s, 1H), 8.21 (s, 2H), 7.78-7.90 (m, 4H), 7.22-7.46 (m, 3H), 6.92-7.20 (m, 1H), 3.85 (s, 3H), 2.74 (s, 3H). MS m/z = 358.9 (M + H)$^+$ |
| 11 | 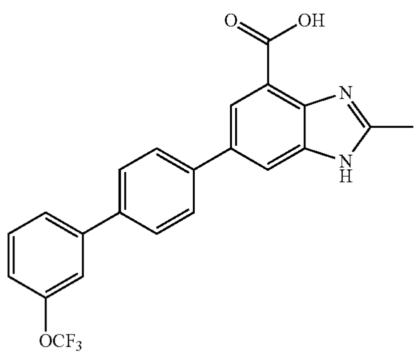 [SMILES: Cc1nc2c(C(=O)O)cc(-c3ccc(-c4cccc(OC(F)(F)F)c4)cc3)cc2[nH]1] | A-1 & E | $^1$H NMR (300 MHz, DMSO-d$_6$): δ 14.00 (bs, 1H), 8.25 (s, 2H), 7.84-7.92 (m, 4H), 7.80 (m, 1H), 7.7 (s, 1H), 7.60-7.68 (m, 1H), 7.40 (d, J = 7.8 Hz, 1H), 2.78 (s, 3H). MS m/z = 412.9 (M + H)$^+$ |
| 12 | 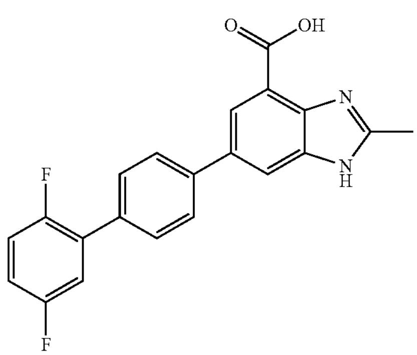 [SMILES: Cc1nc2c(C(=O)O)cc(-c3ccc(-c4cc(F)ccc4F)cc3)cc2[nH]1] | A-1 & E | $^1$H NMR (300 MHz, DMSO-d$_6$): δ 13.80 (bs, 1H), 8.18 (m, 2H), 7.88 (m, 2H), 7.72 (m, 2H), 7.29-7.49 (m, 3H), 2.71 (s, 3H). MS m/z = 365 (M + H)$^+$ |
| 13 | 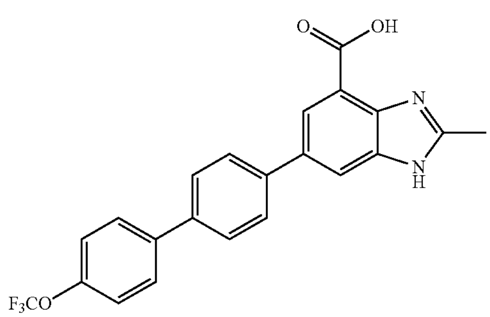 [SMILES: Cc1nc2c(C(=O)O)cc(-c3ccc(-c4ccc(OC(F)(F)F)cc4)cc3)cc2[nH]1] | A-1 & E | $^1$H NMR (300 MHz, DMSO-d$_6$): δ 13.80 (bs, 1H), 8.18-8.26 (m, 2H), 7.80-7.92 (m, 6H), 7.47-7.50 (m, 2H), 2.73 (s, 3H). MS m/z = 411.3 (M − H)$^-$ |

TABLE II-continued
| Example No | Structure | General Procedure | Analytical data |
|---|---|---|---|
| 14 | 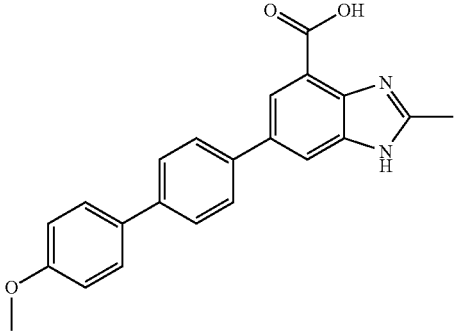 [SMILES: COc1ccc(-c2ccc(-c3cc(C(=O)O)c4nc(C)[nH]c4c3)cc2)cc1] | A-1 & E | $^1$H NMR (300 MHz, DMSO-d$_6$): δ 14.20 (bs, 1H), 8.23-8.25 (m, 2H), 7.76-7.85 (m, 4H), 7.67-7.70 (m, 2H), 7.04-7.07 (m, 2H), 3.81 (s, 3H), 2.82 (s, 3H). |
| 15 | 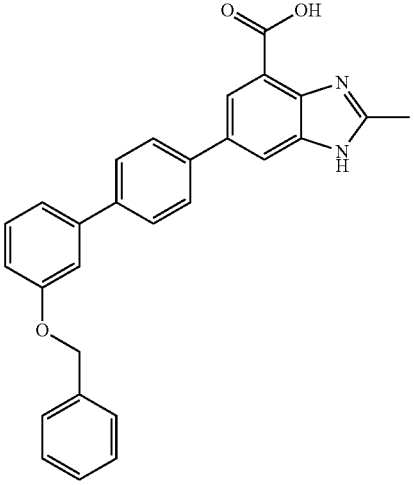 [SMILES: Cc1nc2c(C(=O)O)cc(-c3ccc(-c4cccc(OCc5ccccc5)c4)cc3)cc2[nH]1] | A-1 & E | $^1$H NMR (300 MHz, DMSO-d$_6$): δ 14.0 (bs, 1H), 8.28 (s, 2H), 7.80-7.90 (m, 4H), 7.46-7.54 (m, 2H), 7.30-7.43 (m, 6H), 7.05 (d, 1H), 4.2 (s, 2H), 2.8 (s, 3H).<br>MS m/z = 434.9 (M + H)$^+$ |
| 16 | 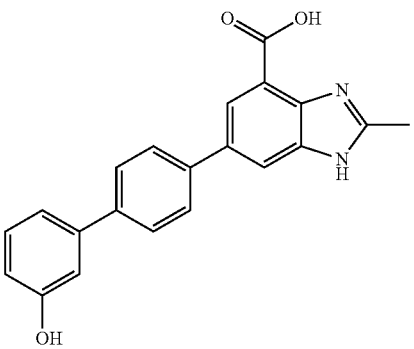 [SMILES: Cc1nc2c(C(=O)O)cc(-c3ccc(-c4cccc(O)c4)cc3)cc2[nH]1] | A-1 & E | $^1$H NMR (300 MHz, DMSO-d$_6$): δ 14.20 (bs, 1H), 9.80 (bs, 1H), 8.21 (bs, 2H), 7.73-7.86 (m, 4H), 7.26-7.31 (m, 1H), 7.11-7.20 (m, 2H), 6.81 (d, J = 7.8 Hz, 1H), 2.76 (s, 3H).<br>MS m/z = 343.2 (M − H)$^-$ |

TABLE II-continued

| Example No | Structure | General Procedure | Analytical data |
|---|---|---|---|
| 17 | 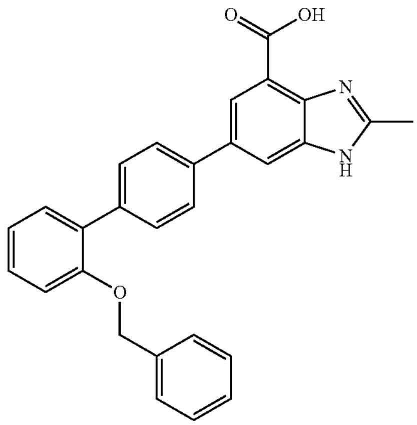 [SMILES: Cc1nc2c(C(=O)O)cc(-c3ccc(-c4ccccc4OCc4ccccc4)cc3)cc2[nH]1] | A-1 & E | $^1$H NMR (300 MHz, DMSO-d$_6$): δ 7.99 (br.s, 1H), 7.83 (br.s 1H), 7.60-7.79 (m, 5H), 7.19-7.49 (m, 8H), 7.06 (s, 1H), 5.2 (s, 2H), 2.6 (s, 3H). MS m/z = 435.1 (M + H)$^+$ |
| 18 | 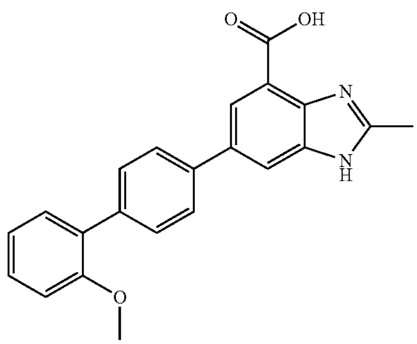 [SMILES: COc1ccccc1-c1ccc(-c2cc(C(=O)O)c3nc(C)[nH]c3c2)cc1] | A-1 & E | $^1$H NMR (300 MHz, DMSO-d$_6$): δ 7.97 (d, J = 12.9, 2H), 7.72 (m, 2H), 7.56 (m, 3H), 7.34 (d, J = 6.6 Hz, 2H), 7.12 (d, J = 7.2 Hz, 1H), 7.0 (s, 1H), 3.99 (s, 3H), 2.6 (s, 3H). MS m/z = 359.1 (M + H)$^+$ |
| 19 | 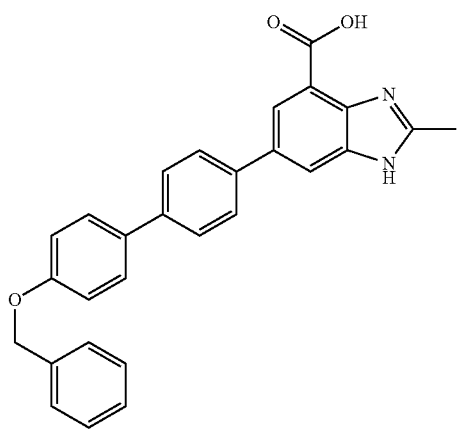 [SMILES: Cc1nc2c(C(=O)O)cc(-c3ccc(-c4ccc(OCc5ccccc5)cc4)cc3)cc2[nH]1] | A-1 & E | $^1$H NMR (300 MHz, DMSO-d$_6$): δ 8.2 (s, 1H), 7.89 (m, 7H), 7.2 (m, 7H), 5.2 (s, 2H), 2.8 (s, 3H). (2H-Not revealed by $^1$H NMR). MS m/z = 435.1 (M + H)$^+$ |
| 20 | 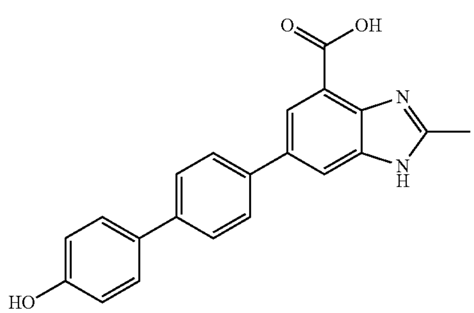 [SMILES: Cc1nc2c(C(=O)O)cc(-c3ccc(-c4ccc(O)cc4)cc3)cc2[nH]1] | A-1 & E | $^1$H NMR (300 MHz, DMSO-d$_6$): δ (ppm) 9.6 (s, 1H), 8.0 (m, 2H), 7.7 (m, 4H), 7.5 (d, J = 8.4 Hz, 2H), 6.8 (d, J = 8.1 Hz, 2H), 2.6 (s, 3H). (2H-Not revealed by $^1$H NMR). MS m/z = 345.2 (M + H)$^+$ |

TABLE II-continued

| Example No | Structure | General Procedure | Analytical data |
|---|---|---|---|
| 21 | 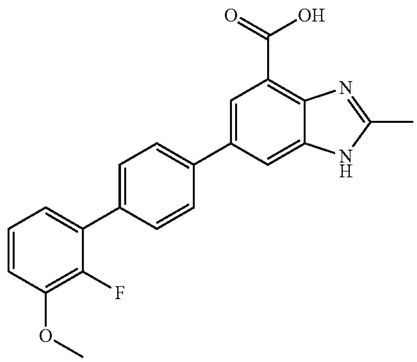 [SMILES: COc1cccc(-c2ccc(-c3cc(C(=O)O)c4nc(C)[nH]c4c3)cc2)c1F] | A-1 & E | $^1$H NMR (300 MHz, DMSO-d$_6$): δ 8.2 (d, J = 11.1 Hz, 2H), 7.8 (d, J = 8.4 Hz, 2H), 7.6 (d, J = 7.5 Hz, 2H), 7.29 (m, 3H), 3.9 (s, 3H), 2.6 (s, 3H). (2H-Not revealed by $^1$HNMR). MS m/z = 377.1 (M + H)$^+$ |
| 22 | 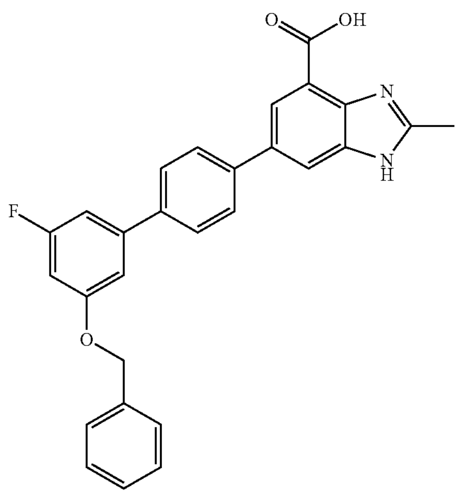 [SMILES: Cc1nc2c(C(=O)O)cc(-c3ccc(-c4cc(F)cc(OCc5ccccc5)c4)cc3)cc2[nH]1] | A-1 & E | $^1$H NMR (300 MHz, DMSO-d$_6$): δ 8.19 (d, J = 4.2 Hz, 2H), 7.85 (s, 4H), 7.45 (m, 5H), 7.2 (m, 2H), 7.0 (d, J = 10.5 Hz, 1H), 5.2 (s, 2H), 2.8 (s, 3H). (2H-Not revealed by $^1$H NMR). MS m/z = 453.1 (M + H)$^+$ |
| 23 | 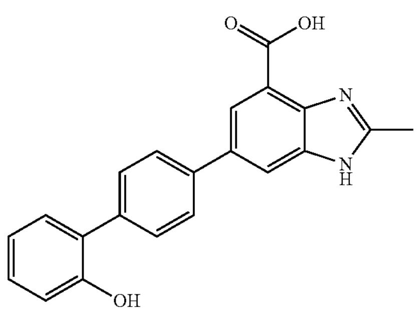 [SMILES: Cc1nc2c(C(=O)O)cc(-c3ccc(-c4ccccc4O)cc3)cc2[nH]1] | A-1 & E | $^1$H NMR (300 MHz, DMSO-d$_6$): δ 14.0 (bs, 1H), 9.69 (bs, 1H), 8.25 (m, 2H), 7.80 (d, J = 8.1 Hz, 2H), 7.69-7.71 (d, J = 8.1 Hz, 2H), 7.34 (d, J = 7.2 Hz, 1H), 7.19 (m, 2 Hz, 1H), 7.01 (d, J = 8.1 Hz, 1H), 6.90 (m, 1H), 2.8 (s, 3H). MS m/z = 345.2 (M + H)$^+$ |
| 24 | 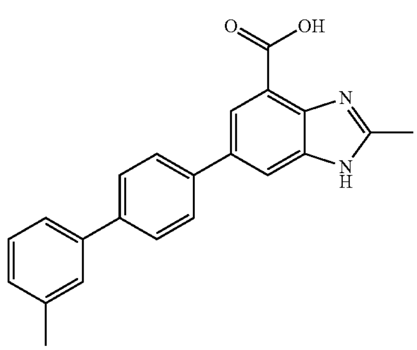 [SMILES: Cc1cccc(-c2ccc(-c3cc(C(=O)O)c4nc(C)[nH]c4c3)cc2)c1] | A-1 & E | $^1$H NMR (300 MHz, DMSO-d$_6$): δ (ppm) 8.27 (s, 2H), 7.83 (m, 4H), 7.52 (m, 2H), 7.39 (m, 1H), 7.2 (d, J = 7.2 Hz, 1H), 2.8 (s, 3H), 2.4 (s, 3H). (2H-Not revealed by $^1$H NMR). MS m/z = 343.1 (M + H)$^+$ |

TABLE II-continued

| Example No | Structure | General Procedure | Analytical data |
|---|---|---|---|
| 25 | (6-(3'-methyl-[1,1'-biphenyl]-4-yl)-2-methyl-1H-benzimidazole-4-carboxylic acid) | A-1 & E | $^1$H NMR (300 MHz, DMSO-d$_6$): δ 8.18 (d, J = 7.5 Hz, 2H), 7.81 (d, J = 8.1 Hz, 2H), 7.47 (d, J = 7.5 Hz, 2H), 7.28 (m, 4H), 2.8 (s, 3H), 2.4 (s, 3H). (2H-Not revealed by $^1$H NMR). MS m/z = 343.1 (M + H)$^+$ |
| 26 | (2-methyl-6-(4'-(piperidin-1-ylmethyl)-[1,1'-biphenyl]-4-yl)-1H-benzimidazole-4-carboxylic acid, TFA salt) | A-1, B & E, G | $^1$H NMR (300 MHz, DMSO-d$_6$): δ 14.00 (bs, 1H), 9.60 (s, 1H), 8.25 (m, 2H), 7.85 (m, 6H), 7.60 (m, 2H), 4.40 (s, 2H), 3.40 (m, 2H), 3.0 (m, 2H), 2.80 (s, 3H), 1.80 (m, 2H), 1.60 (m, 3H), 1.2 (m, 1H). MS m/z = 426 (M + H)$^+$ |
| 27 | (6-(4'-((isopropylamino)methyl)-[1,1'-biphenyl]-4-yl)-2-methyl-1H-benzimidazole-4-carboxylic acid, TFA salt) | A-1, B & E, G | $^1$H NMR (300 MHz, DMSO-d$_6$): δ (ppm) 8.80 (s, 1H), 8.26 (m, 2H), 7.88 (m, 6H), 7.64 (m, 2H), 4.22 (s, 2H), 3.40 (m, 1H), 2.77 (s, 3H), 1.60 (d, J = 6 Hz, 6H). (3H-Not revealed by $^1$H NMR). MS m/z = 400.1 (M + H)$^+$ |
| 28 | (2-methyl-6-(4'-(pyrrolidin-1-ylmethyl)-[1,1'-biphenyl]-4-yl)-1H-benzimidazole-4-carboxylic acid, TFA salt) | A-1, B & E, G | $^1$H NMR (300 MHz, DMSO-d$_6$): δ 14.20 (bs, 1H), 11.45 (s, 1H), 8.25 (s, 2H), 7.85-7.95 (m, 8H), 4.40 (s, 2H), 3.40 (m, 2H), 3.20 (m, 2H), 2.65 (s, 3H), 2.0 (m, 4H). MS m/z = 412.1 (M + H)$^+$ |

TABLE II-continued

| Example No | Structure | General Procedure | Analytical data |
|---|---|---|---|
| 29 | (benzimidazole-carboxylic acid with biphenyl-CH2-thiomorpholine; TFA salt) | A-1, B & E, G | ¹H NMR (300 MHz, DMSO-d$_6$): δ 13.60 (bs, 1H), 10.00 (bs, 1H), 8.35 (m, 2H), 7.80 (m, 6H), 7.60 (m, 2H), 4.40 (s, 2H), 3.65 (m, 2H), 3.20 (m, 2H), 2.80 (m, 4H), 2.65 (s, 3H). MS m/z = 444.1 (M + H)⁺ |
| 30 | (benzimidazole-carboxylic acid with biphenyl-CH2-3,3-difluoropiperidine; TFA salt) | A-1, B & E, G | ¹H NMR (300 MHz, DMSO-d$_6$): δ 13.80 (bs, 1H), 8.28 (m, 2H), 7.90 (m, 6H), 7.54 (m, 3H), 4.20 (s, 2H), 3.20 (m, 2H), 2.80 (s, 3H), 2.0 (m, 3H), 1.60 (m, 3H). MS m/z = 462.1 (M + H)⁺ |
| 31 | (benzimidazole-carboxylic acid with 3'-piperidinylmethyl-biphenyl; TFA salt) | A-1, B & E, G | ¹H NMR (300 MHz, DMSO-d$_6$): δ 9.60 (bs, 1H), 8.40 (m, 2H), 7.90 (m, 6H), 7.60 (m, 1H), 7.52 (m, 1H), 4.40 (s, 2H), 3.40 (m, 2H), 2.95 (m, 2H), 2.75 (s, 3H), 1.75 (m, 2H), 1.70 (m, 3H), 1.40 (m, 1H). MS m/z = 426.2 (M + H)⁺ |

TABLE II-continued
| Example No | Structure | General Procedure | Analytical data |
|---|---|---|---|
| 32 | 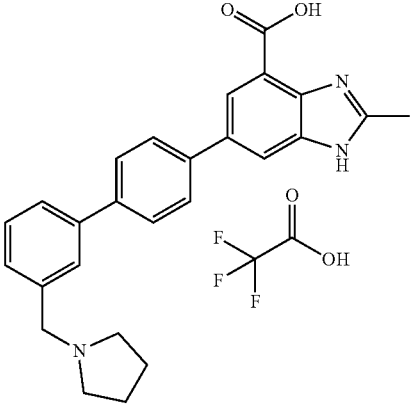 | A-1, B & E, G | $^1$H NMR (300 MHz, DMSO-d$_6$): δ 12.40 (bs, 1H), 8.00 (m, 2H), 7.65 (m, 6H), 7.40 (m, 2H), 4.00 (s, 2H), 2.80 (m, 4H), 2.60 (s, 3H), 1.80 (m, 4H). MS m/z = 412.0 (M + H)$^+$ |
| 33 | 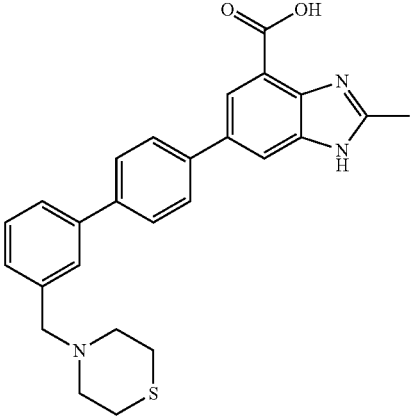 [SMILES: Cc1nc2c(C(=O)O)cc(-c3ccc(-c4cccc(CN5CCSCC5)c4)cc3)cc2[nH]1] | A-1, B & E, G | $^1$H NMR (300 MHz, DMSO-d$_6$): δ 14.20 (bs, 1H), 11.80 (s, 1H), 8.25 (s, 2H), 8.20 (s, 1H), 7.85 (m, 4H), 7.60 (m, 3H), 4.48 (s, 2H), 3.2-3.4 (m, 6H), 2.80 (s, 3H), 2.75 (m, 2H). MS m/z = 444.1 (M + H)$^+$ |
| 34 | 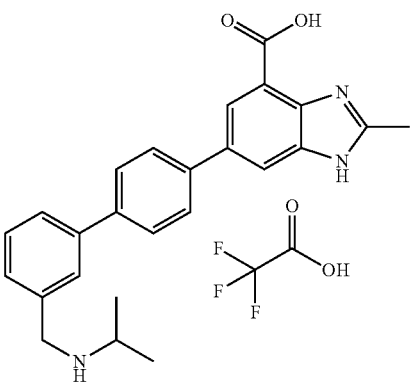 | A-1, B & E, G | $^1$H NMR (300 MHz, DMSO-d$_6$): δ 13.80 (bs, 1H), 8.80 (s, 2H), 8.25 (m, 2H), 7.85 (m, 6H), 7.60 (m, 2H), 4.25 (s, 2H), 3.10 (m, 1H), 2.80 (s, 3H), 1.25 (m, 6H). MS m/z = 400.1 (M + H)$^+$ |

TABLE II-continued

| Example No | Structure | General Procedure | Analytical data |
|---|---|---|---|
| 35 | 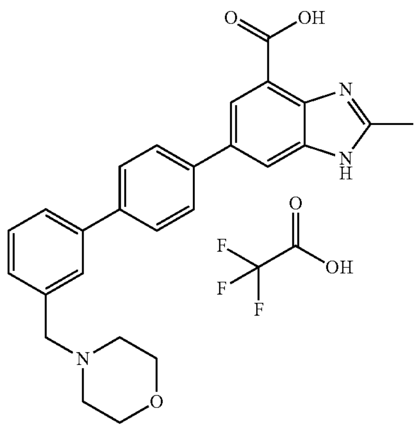 | A-1, B & E, G | $^1$H NMR (300 MHz, DMSO-d$_6$): δ 13.40 (bs, 1H), 11.80 (s, 1H), 8.20 (m, 3H), 7.85 (m, 5H), 7.60 (m, 2H), 4.40 (s, 2H), 3.20 (m, 8H), 2.80 (s, 3H). MS m/z = 428.1 (M + H)$^+$ |
| 36 | 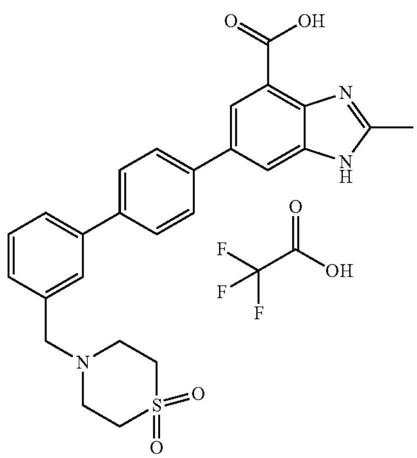 | A-1, B, C & E, G | $^1$H NMR (300 MHz, DMSO-d$_6$): δ 8.20 (s, 1H), 8.15 (s, 1H), 7.80 (m, 6H), 7.40 (m, 2H), 4.15 (s, 2H), 3.40 (m, 4H), 3.20 (m, 4H), 2.80 (s, 3H). (2H-Not revealed by $^1$H NMR). MS m/z = 474.1 (M − H)$^-$ |
| 37 | 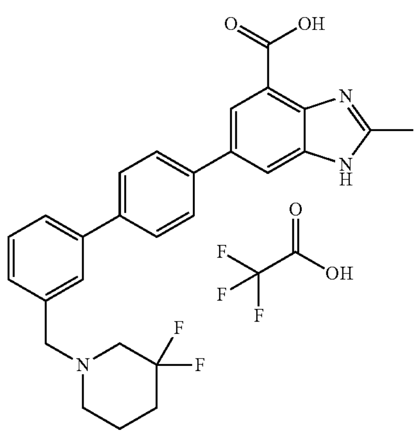 | A-1, B & E, G | $^1$H NMR (300 MHz, CD$_3$OD): δ 8.45 (s, 1H), 8.20 (s, 1H), 7.85 (m, 6H), 7.60 (m, 2H), 4.45 (s, 2H), 3.65 (m, 2H), 3.41 (s, 2H), 2.85 (s, 3H), 2.20 (m, 4H). (2H-Not revealed by $^1$H NMR). MS m/z = 462 (M + H)$^+$ |

TABLE II-continued
| Example No | Structure | General Procedure | Analytical data |
|---|---|---|---|
| 38 | 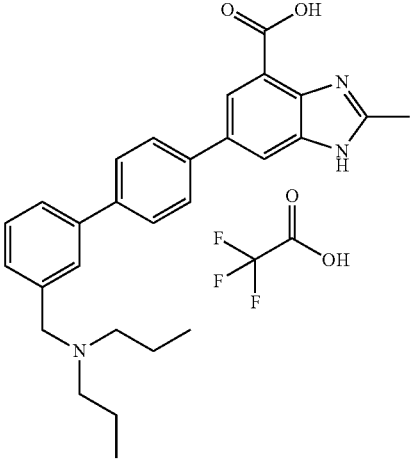 | A-1, B & E, G | $^1$H NMR (300 MHz, DMSO-d$_6$): δ 13.60 (bs, 1H), 9.60 (bs, 1H), 8.22 (d, J = 10.2 Hz, 2H), 7.85 (m, 6H), 7.60 (m, 2H), 4.45 (s, 2H), 3.20 (m, 4H), 2.80 (s, 3H), 1.65 (m, 4H), 0.90 (s, 6H). MS m/z = 442 (M + H)+ |
| 39 | 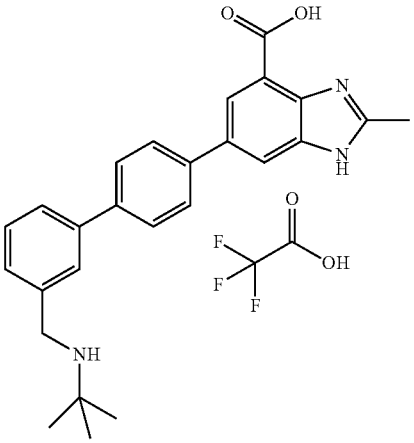 | A-1, B & E, G | $^1$H NMR (300 MHz, DMSO-d$_6$): δ 14.00 (bs, 1H), 8.81 (s, 2H), 7.55-8.30 (m, 8H), 4.20 (s, 2H), 2.80 (s, 3H), 1.40 (s, 9H). (2H-Not revealed by $^1$H NMR). MS m/z = 413.9 (M + H)$^+$ |
| 40 | 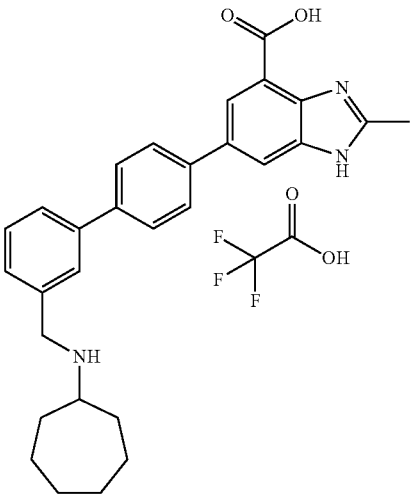 | A-1, B & E, G | $^1$H NMR (300 MHz, DMSO-d$_6$): δ 8.0 (m, 2H), 7.20-7.80 (m, 8H), 4.20 (s, 2H), 2.8 (s, 3H), 1.80 (m, 2H), 1.42-1.80 (m, 11H). (3H-Not revealed by $^1$H NMR). MS m/z = 454.1 (M + H)+ |

TABLE II-continued
| Example No | Structure | General Procedure | Analytical data |
|---|---|---|---|
| 41 | 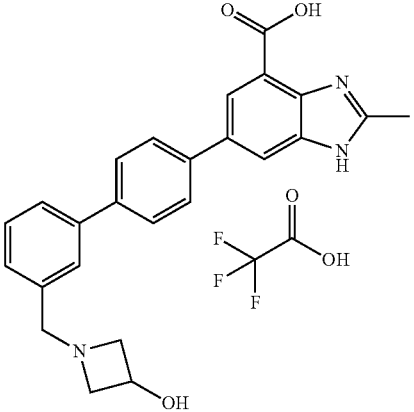 | A-1, B & E, G | $^1$H NMR (300 MHz, DMSO-d$_6$): δ 7.2-8.2 (m, 10H), 4.20 (s, 1H), 3.60 (m, 4H), 2.89 (s, 3H), 1.91 (s, 3H). (2H-Not revealed by $^1$H NMR). MS m/z = 414.1 (M + H)$^+$ |
| 42 | 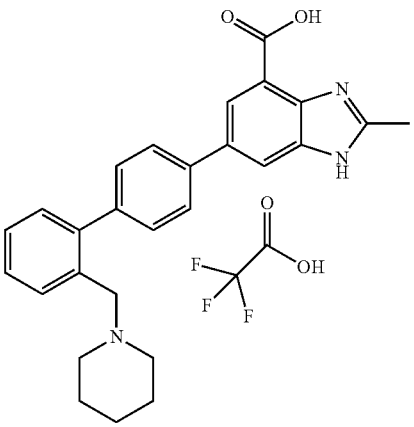 | A-1, B & E, G | $^1$H NMR (300 MHz, DMSO-d$_6$): δ 13.25 (bs, 1H), 9.20 (s, 1H), 8.23 (s, 1H), 8.20 (s, 1H), 7.85 (m, 3H), 7.45 (m, 5H), 4.40 (s, 2H), 3.20 (m, 4H), 2.80 (s, 3H), 1.65 (m, 4H), 1.30 (m, 2H). MS m/z = 425.9 (M + H)$^+$ |
| 43 | 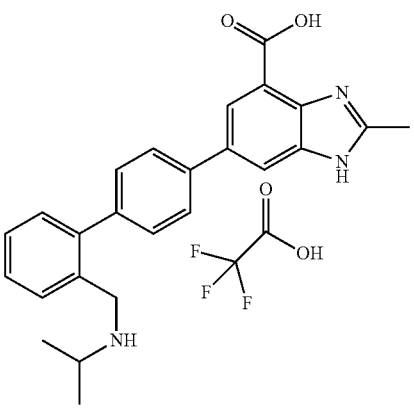 | A-1, B & E, G | $^1$H NMR (300 MHz, DMSO-d$_6$): δ 8.85 (bs, 2H), 8.30 (s, 1H), 8.20 (s, 1H), 7.85 (m, 2H), 7.75 (m, 1H), 7.55 (m, 4H), 7.45 (m, 1H), 4.15 (s, 2H), 3.45 (m, 1H), 2.75 (s, 3H), 1.15-1.13 (d, J = 6.0 Hz, 6H). (2H-Not revealed by $^1$H NMR). MS m/z = 400.1 (M + H)$^+$ |

TABLE II-continued

| Example No | Structure | General Procedure | Analytical data |
|---|---|---|---|
| 44 | 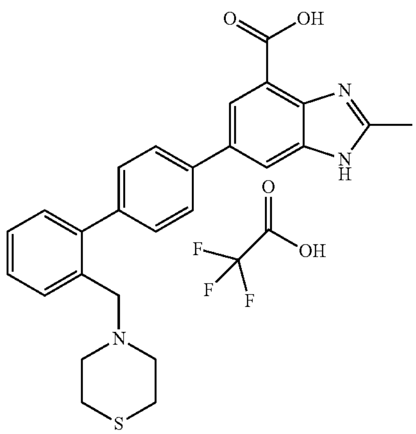 | A-1, B & E, G | $^1$H NMR (300 MHz, DMSO-d$_6$): δ 14.00 (bs, 1H), 10.00 (bs, 1H), 8.35 (s, 1H), 8.25 (s, 1H), 7.80 (m, 3H), 7.4-7.6 (m, 5H), 4.40 (s, 2H), 3.00 (m, 5H), 2.80 (s, 3H), 2.65 (m, 3H). MS m/z = 444 (M + H)+ |
| 45 | 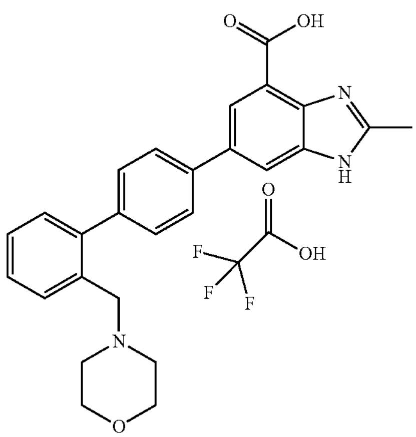 | A-1, B & E, G | $^1$H NMR (300 MHz, DMSO-d$_6$): δ 13.20 (bs, 1H), 8.60 (s, 1H), 8.20 (s, 2H), 8.00 (m, 3H), 7.4-7.6 (m, 5H), 4.30 (s, 2H), 3.80 (m, 4H), 2.80 (s, 3H), 2.70 (m, 4H). MS m/z = 428.1 (M + H)$^+$ |
| 46 | 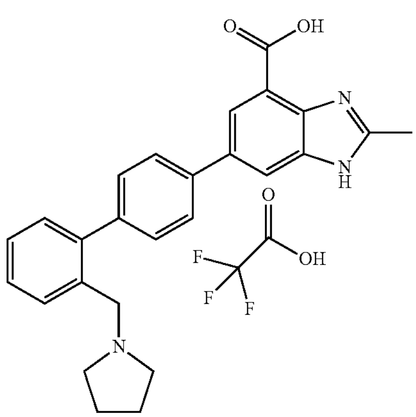 | A-1, B & E, G | $^1$H NMR (300 MHz, DMSO-d$_6$): δ 14.0 (bs, 1H), 9.0 (bs, 1H), 8.46 (s, 1H), 8.25 (s, 1H), 7.80 (m, 3H), 7.53 (m, 5H), 4.50 (s, 2H), 3.20 (m, 4H), 2.80 (s, 3H), 1.80 (m, 4H). MS m/z = 412.2 (M + H)$^+$ |

TABLE II-continued

| Example No | Structure | General Procedure | Analytical data |
|---|---|---|---|
| 47 | 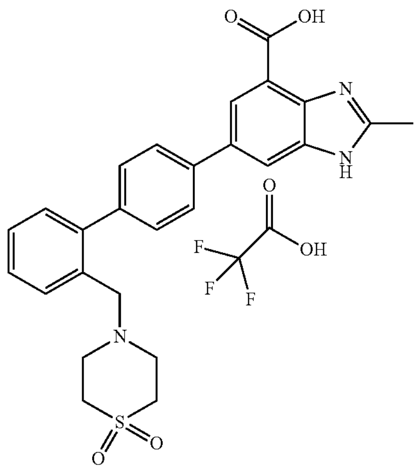 | A-1, B & E, G | $^1$H NMR (300 MHz, DMSO-d$_6$): δ 14.00 (bs, 1H), 8.25 (s, 2H), 7.85 (m, 2H), 7.60 (m, 3H), 7.40 (m, 3H), 3.65 (s, 2H), 3.00 (m, 4H), 2.83 (m, 7H). MS m/z = 476.1 (M + H)$^+$ |
| 48 | 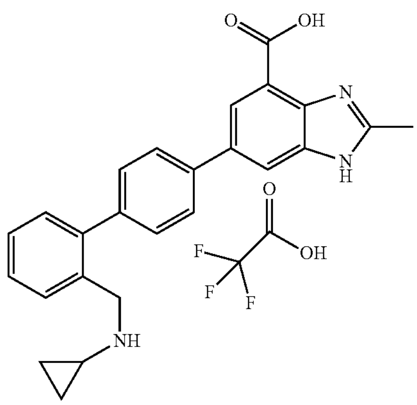 | A-1, B & E, G | $^1$H NMR (300 MHz, DMSO-d$_6$): δ 13.60 (bs, 1H), 9.17 (bs, 2H), 8.30 (s, 1H), 8.26 (s, 1H), 8.00 (m, 2H), 7.53 (m, 6H), 4.27 (m, 3H), 2.77 (s, 3H), 0.71 (m, 4H). MS m/z = 396.1 (M − H)$^-$ |
| 49 | 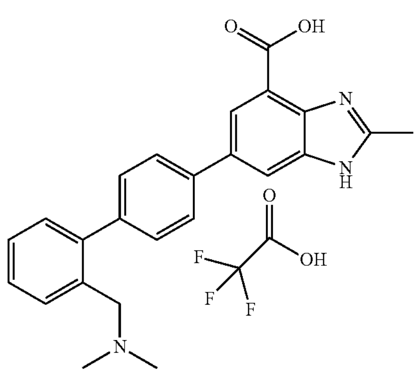 | A-1, B & E, G | $^1$H NMR (300 MHz, DMSO-d$_6$): δ 14.20 (bs, 1H), 10.80 (bs, 1H), 8.40 (s, 2H), 8.00 (m, 3H), 7.40 (m, 5H), 4.35 (s, 2H), 2.88 (s, 3H), 2.27 (s, 6H). MS m/z = 386.1 (M + H)$^+$ |

TABLE II-continued

| Example No | Structure | General Procedure | Analytical data |
|---|---|---|---|
| 50 | 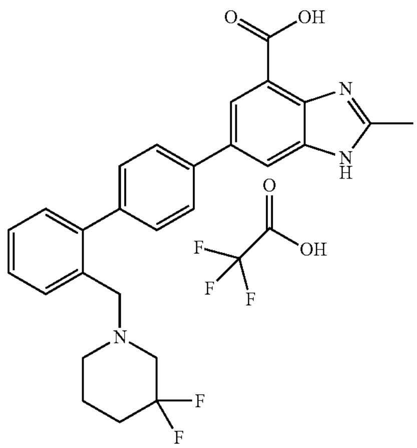 | A-1, B & E, G | ¹H NMR (300 MHz, DMSO-d₆): δ 14.00 (bs, 1H), 8.25 (m, 2H), 7.8-8.0 (m, 2H), 7.3-7.7 (m, 6H), 3.62 (s, 2H), 2.80 (s, 3H), 2.50 (m, 3H), 1.80 (m, 5H). MS m/z = 462.1 (M + H)⁺ |
| 51 | 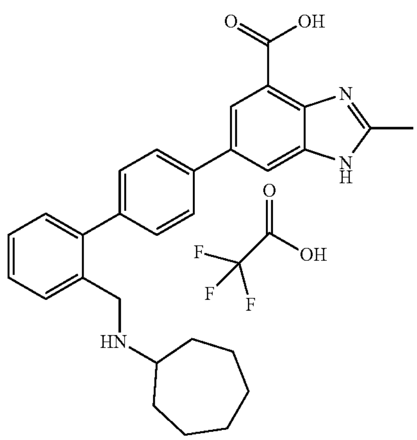 | A-1, B & E, G | ¹H NMR (300 MHz, DMSO-d₆): δ (ppm) 13.20 (bs, 1H), 8.73 (s, 1H), 8.21 (s, 1H), 8.16 (s, 1H), 7.4-7.9 (m, 7H), 4.20 (s, 2H), 2.80 (s, 3H), 1.80 (m, 2H), 1.40 (m, 11H). (2H-Not revealed by ¹H NMR). MS m/z = 454.2 (M + H)⁺ |
| 52 | 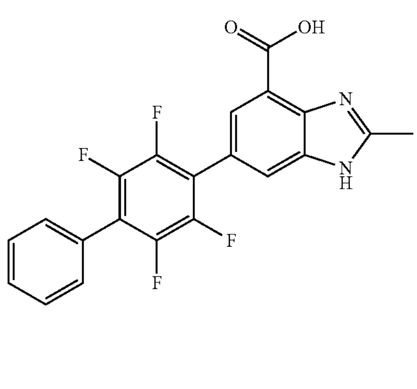 [SMILES: Cc1nc2c(C(=O)O)cc(-c3c(F)c(F)c(-c4ccccc4)c(F)c3F)cc2[nH]1] | A-2 & E | ¹H NMR (300 MHz, DMSO-d₆): δ 14.0 (bs, 1H), 8.3 (s, 1H), 8.2 (s, 1H), 7.6 (m, 5H), 3.0 (s, 3H). MS m/z = 401 (M + H)⁺ |

TABLE II-continued

| Example No | Structure | General Procedure | Analytical data |
|---|---|---|---|
| 53 | 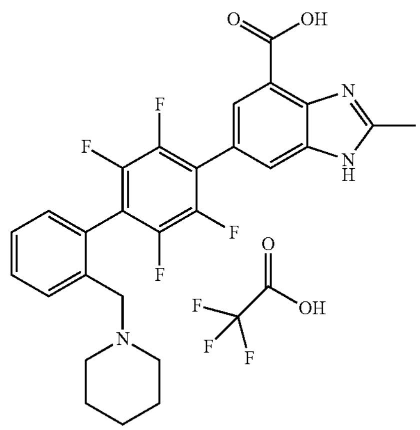 | A-2, B & E, G | ¹H NMR (300 MHz, DMSO-d₆): δ 13.0 (bs, 1H), 9.6 (bs, 1H), 8.0 (m, 3H), 7.6 (m, 3H), 4.2 (s, 2H), 2.6 (m, 4H), ), 2.2 (s, 3H), 1.7 (m, 4H), 1.2 (m, 2H). MS m/z = 496.1 (M − H)⁻ |
| 54 | 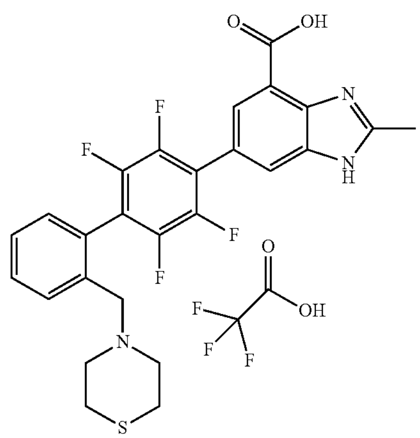 | A-2, B & E, G | ¹H NMR (300 MHz, DMSO-d₆): δ 8.19 (s, 1H), 8.02 (s, 1H), 7.74 (d, J = 6.0 Hz, 1H), 7.6 (m, 2H), 7.45 (d, J = 6.0 Hz 1H), 4.2 (s, 2H), 3.2 (m, 4H), 2.8 (m, 7H). (2H-Not revealed by ¹H NMR). MS m/z = 516.0 (M + H)⁺ |
| 55 | 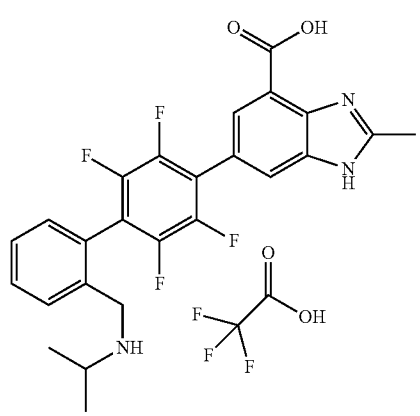 | A-2, B & E, G | ¹H NMR (300 MHz, DMSO-d₆): δ 13.0 (bs, 1H), 8.8 (bs, 2H), 7.5-8.2 (m, 6H), 4.2 (s, 2H), 3.40 (m, 1H), 2.8 (s, 3H), 1.25 (m, 6H). MS m/z = 472.1 (M + H)⁺ |

TABLE II-continued

| Example No | Structure | General Procedure | Analytical data |
|---|---|---|---|
| 56 | 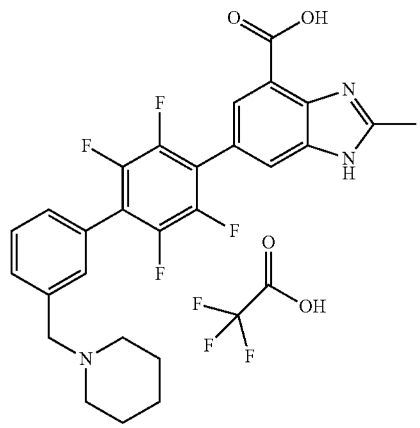 | A-2 B & E, G | $^1$H NMR (300 MHz, DMSO-d$_6$): δ 9.7 (bs, 1H), 8.1 (s, 1H), 8.0 (s, 1H), 7.7 (m, 4H), 4.4 (s, 2H), 2.8 (s, 3H), 2.6 (m, 4H), 1.8 (m, 6H). MS m/z = 498.1 (M + H)$^+$ |
| 57 | 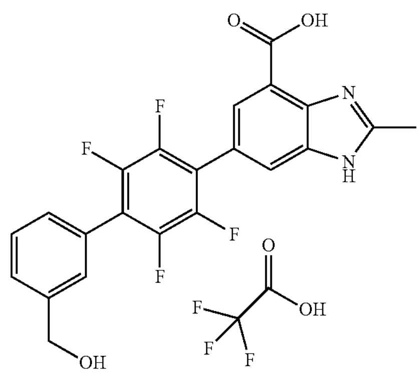 | A-2, B & E, G | $^1$H NMR (300 MHz, DMSO-d$_6$): δ 8.2 (s, 1H), 8.1 (s, 1H), 7.4 (m, 4H), 4.6 (s, 2H), 2.8 (s, 3H). (3H-Not revealed by $^1$H NMR). MS m/z = 431.1 (M + H)$^+$ |
| 58 | 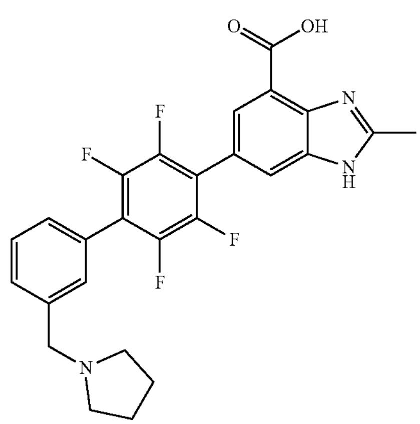 [SMILES: Cc1nc2c(C(=O)O)cc(-c3c(F)c(F)c(-c4cccc(CN5CCCC5)c4)c(F)c3F)cc2[nH]1] | A-2 B & E | $^1$H NMR (300 MHz, DMSO-d$_6$): δ 7.8 (s, 1H), 7.6 (s, 1H), 7.4 (m, 4H), 3.7 (s, 2H), 2.6 (s, 3H), 2.5 (m, 4H), 1.8 (m, 4H). (2H-Not revealed by $^1$H NMR). MS m/z = 483.9 (M + H)$^+$ |

TABLE II-continued

| Example No | Structure | General Procedure | Analytical data |
|---|---|---|---|
| 59 | (structure) | A-2, B & E, G | ¹H NMR (300 MHz, DMSO-d$_6$): δ 8.25 (s, 1H), 8.15 (s, 1H), 7.6 (m, 4H), 4.3 (s, 2H), 3.5 (m, 1H), 2.8 (s, 3H), 1.43-1.41 (d, J = 6.6 Hz, 6H). (3H-Not revealed by ¹H NMR). MS m/z = 471.9 (M + H)⁺ |
| 60 | (structure) | A-2, B & E, G | ¹H NMR (300 MHz, DMSO-d$_6$): δ 8.2 (s, 1H), 8.1 (s, 1H), 7.6 (m, 4H), 4.4 (s, 2H), 2.8 (m, 4H), 0.95 (m, 4H). (3H-Not revealed by ¹H NMR). MS m/z = 470.1 (M + H)⁺ |
| 61 | (structure) | A-2, B & E, G | ¹H NMR (300 MHz, DMSO-d$_6$): δ 8.3 (s, 1H), 8.12 (s, 1H), 7.80-7.69 (m, 4H), 4.42 (s, 2H), 3.56-3.49 (m, 2H), 3.12-3.01 (m, 2H), 2.88 (s, 3H), 2.01-1.70 (m, 6H). (2H-Not revealed by ¹H NMR). MS m/z = 498.1 (M + H)⁺ |
| 62 | (structure) | A-2, B & E, G | ¹H NMR (300 MHz, DMSO-d$_6$): δ 9.1 (bs, 1H), 8.2 (s, 1H), 8.1 (s, 1H), 7.43 (m, 4H), 3.7 (s, 2H), 2.8 (m, 7H), 1.8 (m, 4H). MS m/z = 482.1 (M − H)⁻ |

TABLE II-continued

| Example No | Structure | General Procedure | Analytical data |
|---|---|---|---|
| 63 | 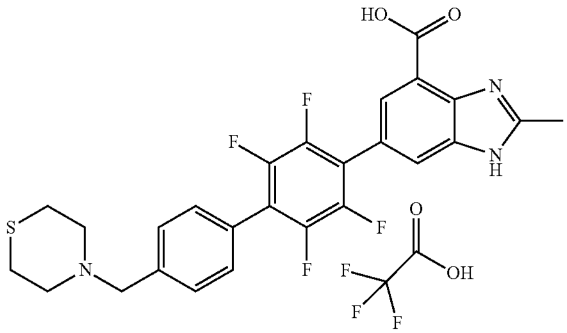 | A-2, B & E, G | ¹H NMR (300 MHz, DMSO-d$_6$): δ 8.2 (s, 1H), 8.1 (s, 1H), 7.75 (m, 4H), 4.4 (s, 2H), 3.5 (m, 4H), 3.0 (m, 4H), 2.8 (s, 3H). (2H-Not revealed by ¹H NMR). MS m/z = 515.9 (M + H)⁺ |
| 64 | 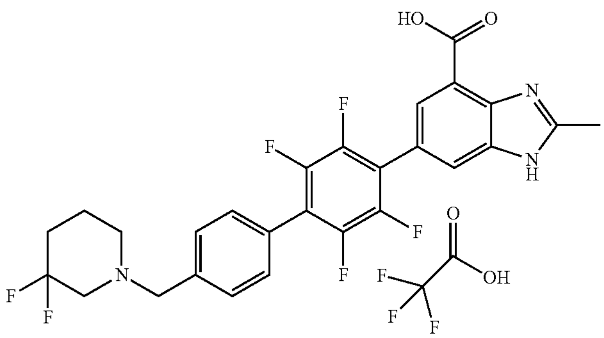 | A-2, B & E, G | ¹H NMR (300 MHz, DMSO-d$_6$): δ 8.2 (s, 1H), 8.1 (s, 1H), 7.75 (m, 4H), 4.4 (s, 2H), 3.5 (m, 4H), 3.0 (s, 3H), 2.2 (m, 4H). (2H-Not revealed by ¹H NMR). MS m/z = 534.1 (M + H)⁺ |
| 65 | 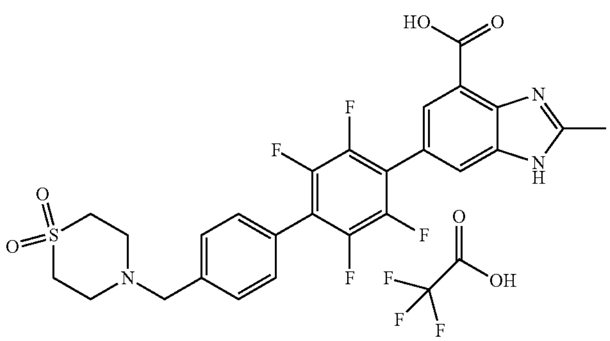 | A-2, B & E, G | ¹H NMR (300 MHz, DMSO-d$_6$): δ 8.2 (s, 1H), 8.1 (s, 1H), 7.6 (m, 4H), 4.0 (s, 2H), 3.0-3.4 (m, 8H), 2.8 (s, 3H). (2H-Not revealed by ¹H NMR). MS m/z = 548.0 (M + H)⁺ |
| 66 | 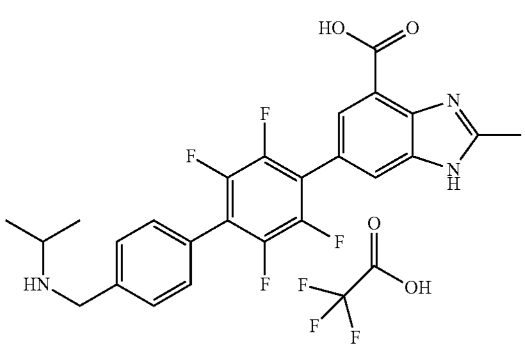 | A-2, B & E, G | ¹H NMR (300 MHz, DMSO-d$_6$): δ 13.80 (bs, 1H). 9.00 (s, 1H), 7.5-8.4 (m, 6H), 4.20 (s, 2H), 2.80 (s, 4H), 1.40 (m, 6H). MS m/z = 472.1 (M + H)⁺ |

TABLE II-continued

| Example No | Structure | General Procedure | Analytical data |
|---|---|---|---|
| 67 | 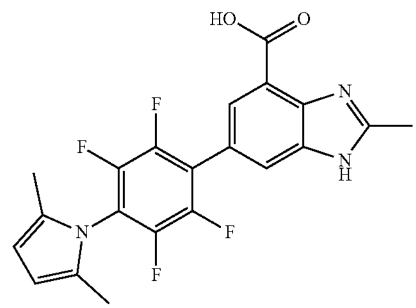 [SMILES: Cc1nc2c(C(=O)O)cc(-c3c(F)c(F)c(-n4c(C)ccc4C)c(F)c3F)cc2[nH]1] | A-2 & E | ¹H NMR (300 MHz, DMSO-d$_6$): δ 8.2 (s, 1H), 8.1 (s, 1H), 6.0 (s, 2H), 2.9 (s, 3H), 2.0 (s, 6H). (2H-Not revealed by ¹H NMR). MS m/z = 418 (M + H)⁺ |
| 68 | 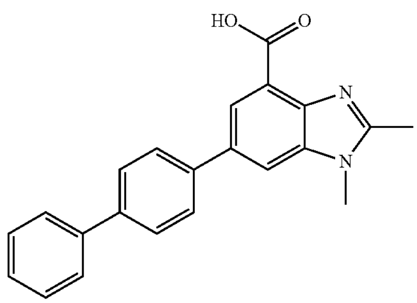 [SMILES: Cc1nc2c(C(=O)O)cc(-c3ccc(-c4ccccc4)cc3)cc2n1C] | 169. A-1 & E | ¹H NMR (300 MHz, DMSO-d$_6$): δ 614.4 (bs, 1H), 8.68 (s, 1H), 8.63(s, 1H), 7.99-7.75 (m, 6H), 7.54-7.41 (m, 3H), 4.05 (s, 3H), 2.91 (s, 3H). MS m/z = 343 (M + H)⁺ |
| 69 | 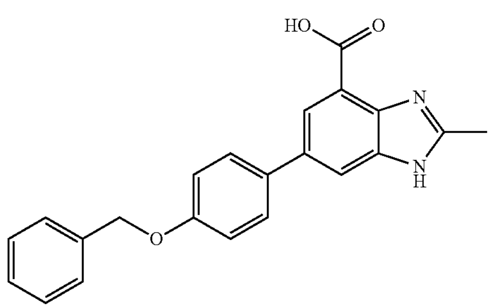 [SMILES: Cc1nc2c(C(=O)O)cc(-c3ccc(OCc4ccccc4)cc3)cc2[nH]1] | A-1 & E | ¹H NMR (300 MHz, DMSO-d$_6$): δ 14 (bs, 1H), 8.12-8.10 (d, J = 6 Hz, 2H), 7.71-7.68 (d, J = 9 Hz, 2H), 7.49-7.34 (m, 5H), 7.16-7.13 (d, J = 8.7 Hz, 2H), 5.18 (s, 2H), 2.76 (s, 3H). MS m/z = 357 (M − H)⁻ |
| 70 | 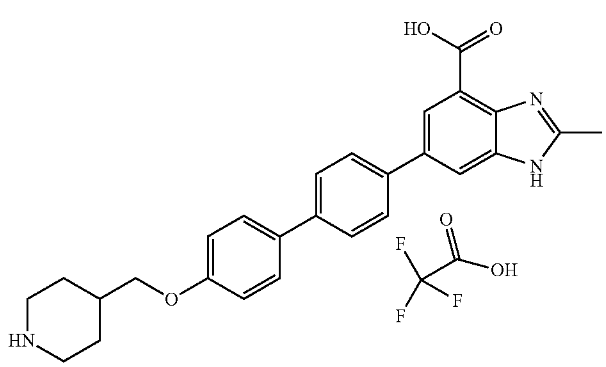 | A-1, D & E, G | ¹H NMR (300 MHz, DMSO-d$_6$): δ 13.6 (bs, 1H), 8.56 (m, 1H), 8.27-8.25 (m, 1H), 8.17-8.14 (d, J = 8.4 Hz, 2H), 7.83-7.67 (m, 6H), 7.08-7.05 (d, J = 8.7 Hz, 2H), 3.94-3.92 (d, J = 6, 2H), 3.49-3.31 (m, 2H), 2.99-2.72 (m, 2H), 2.69 (s, 3H), 2.09 (m, 1H), 1.97-1.93 (m, 2H), 1.54-1.42 (m, 2H). MS m/z = 442. (M + H)⁺ |

TABLE II-continued

| Example No | Structure | General Procedure | Analytical data |
|---|---|---|---|
| 71 | 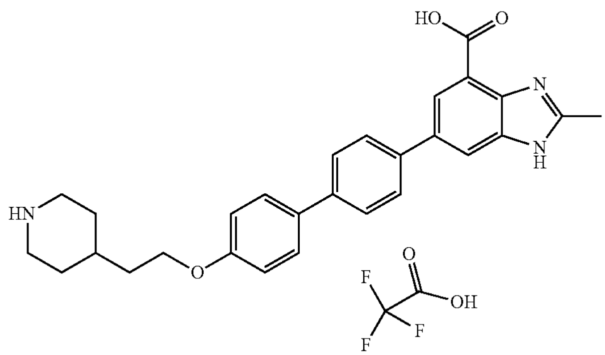 [SMILES: Cc1nc2c(C(=O)O)cc(-c3ccc(-c4ccc(OCCC5CCNCC5)cc4)cc3)cc2[nH]1 ; O=C(O)C(F)(F)F] | A-1, D & E, G | ¹H NMR (300 MHz, DMSO-d₆): δ 13.6 (bs, 1H), 8.75(m, 1H), 8.50 (m, 1H), 8.18-8.17 (m, 2H), 7.83-7.74 (m, 4H), 7.69-7.66 (d, J = 8.4 Hz, 2H), 7.07-7.04 (d, J = 8.7 Hz, 2H), 4.10 (m, 2H), 3.38-3.24 (m, 2H), 2.92-2.81 (q, 2H), 2.72(s, 3H), 1.82-1.73 (m, 2H), 1.73 (m, 2H), 1.44-1.36 (m, 2H). MS m/z = 456 (M + H)⁺ |
| 72 | 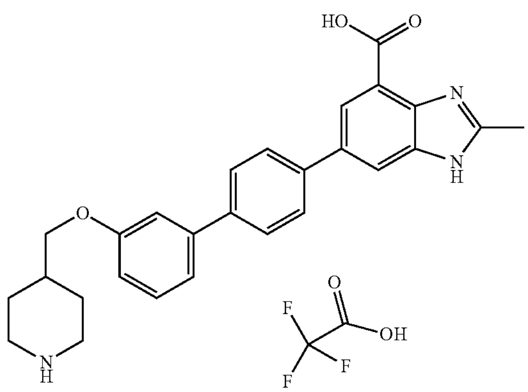 [SMILES: Cc1nc2c(C(=O)O)cc(-c3ccc(-c4cccc(OCC5CCNCC5)c4)cc3)cc2[nH]1 ; O=C(O)C(F)(F)F] | A-1, D & E, G | ¹H NMR (300 MHz, DMSO-d₆): δ 8.81 (m, 1H), 8.52-8.49 (m, 1H), 8.27-8.24 (d, J = 8.7 Hz, 2H), 7.86-7.80 (m, 4H), 7.43-7.26 (m, 3H), 6.98-6.95 (d, J = 7.8 Hz, 1H), 3.98-3.96 (d, J = 6 Hz, 2H), 2.98-2.91(m, 2H), 2.79 (s, 3H), 2.10 (m, 1H), 1.98-1.93 (m, 2H), 1.57-1.45 (q, 2H). (3H-Not revealed by ¹H NMR). MS m/z = 442 (M + H)⁺ |
| 73 | 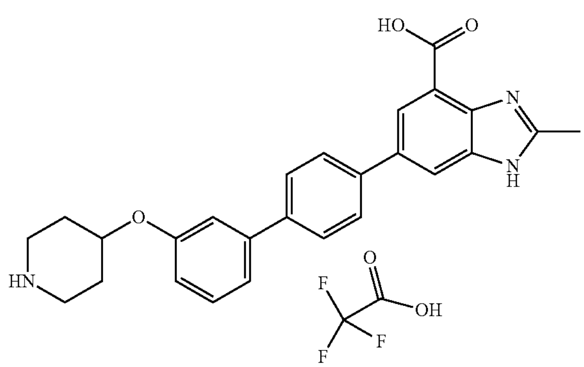 | A-1, D & E, G | ¹H NMR (300 MHz, DMSO-d₆): δ 8.82 (m, 2H), 8.26-8.22 (m, 2H), 7.83 (m, 4H), 7.41-7.33 (m, 3H), 7.04 (m, 1H), 4.79 (m, 1H), 3.28 (m, 2H), 3.13 (m, 2H), 2.79 (s, 3H), 2.13 (m, 2H), 1.88 (m, 2H). MS m/z = 428 (M + H)⁺ |
| 74 | 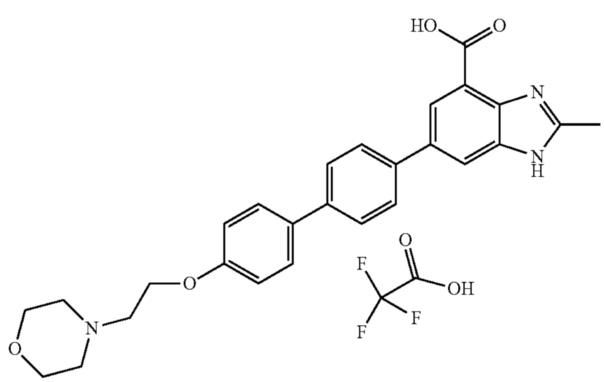 | A-1, D & E, G | ¹H NMR (300 MHz, DMSO-d₆): δ 9.65 (bs, 1H), 8.57(s, 1H), 8.32 (s, 1H), 7.9 (m, 2H), 7.78 (m, 2H), 7.6 (m, 2H), 6.89 (m, 2H), 4.8 (m, 2H), 3.79(m, 7H), 3.23 (m, 2H), 3.01 (m, 2H), 2.95 (s, 3H). MS m/z = 458 (M + H)⁺ |

TABLE II-continued

| Example No | Structure | General Procedure | Analytical data |
|---|---|---|---|
| 75 | 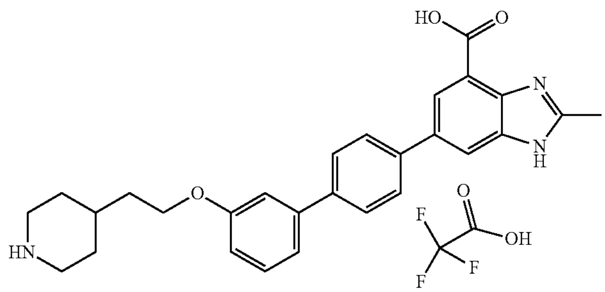 | A-1, D & E, G | ¹H NMR (300 MHz, DMSO-d₆): δ 8.72(m, 1H), 8.43 (m, 1H), 8.23-8.19 (m, 2H), 7.82 (m, 4H), 7.39-7.37 (m, 1H), 7.30-7.25 (m, 2H), 6.96-6.94 (m, 1H), 4.11 (m, 2H), 3.29-3.25 (m, 2H), 2.89-2.86 (m, 2H), 2.74 (s, 3H), 1.91-1.72 (m, 5H), 1.38-1.35 (m, 2H).<br>MS m/z = 456 (M + H)⁺ |
| 76 | 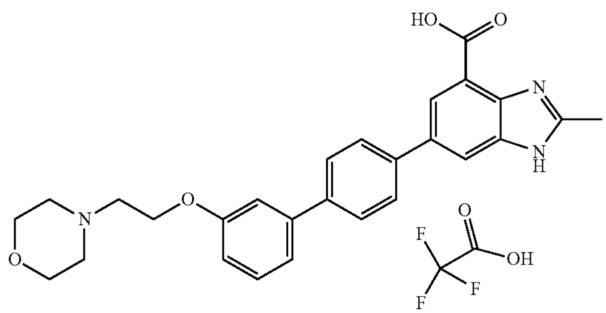 | A-1 & D, E, G | ¹H NMR (300 MHz, DMSO-d₆): δ 8.16 (m, 2H), 7.83-7.71(m, 4H), 7.28 (m, 1H), 7.14-7.09 (m, 2H), 6.80-6.78 (m, 1H, ), 4.93 (m, 2H), 3.88 (m, 4H), 3.50-3.36 (m, 6H), 2.75-2.72 (m, 3H). (2H-Not revealed by ¹H NMR).<br>MS m/z = 458 (M + H)⁺ |
| 77 | 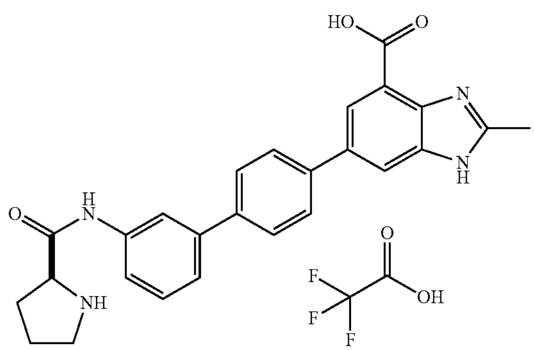 | A-1, F & E, G | ¹H NMR (300 MHz, DMSO-d₆): δ 13.9(bs, 1H), 10.75 (s, 1H), 9.50 (bs, 1H), 8.73 (bs, 1H), 8.28-8.26 (d, J = 6.6 Hz, 2H), 8.01 (s, 1H), 7.92-7.89 (d, J = 8.1 Hz, 2H), 7.80-7.77 (d, J = 8.1 Hz, 2H), 7.63-7.60 (m, 1H), 7.50-7.47(m, 2H), 4.40 (m, 1H), 3.39-3.30 (m, 2H), 2.79 (s, 3H), 2.44-2.40 (m, 1H), 2.05-1.92(m, 3H).<br>MS m/z = 441 (M + H)⁺ |
| 78 | 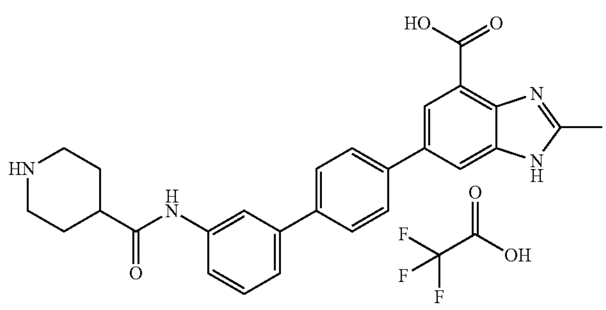 | A-1, F & E, G | ¹H NMR (300 MHz, DMSO-d₆): δ 13.9 (bs, 1H), 10.19 (s, 1H), 8.64 (m, 1H), 8.40-8.37(m, 1H), 8.26-8.25 (m, 2H), 8.03 (s, 1H), 7.91-7.88 (d, J = 8.4 Hz, 2H), 7.78-7.75 (d, J = 8.4 Hz, 2H), 7.62-7.58 (m, 1H), 7.44-7.42 (m, 2H), 3.41-3.35 (m, 2H), 3.02-2.91 (q, 2H), 2.78(s, 3H), 2.73-2.72(m, 1H), 2.08-1.81(m, 4H).<br>MS m/z = 455 (M + H)⁺ |
| 79 | 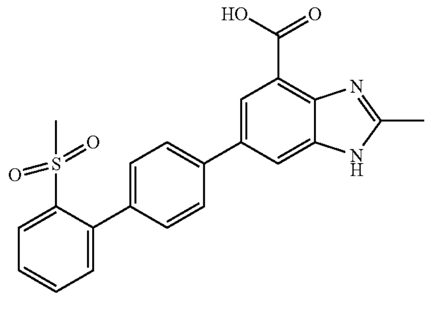 [SMILES: Cc1nc2c(C(=O)O)cc(-c3ccc(-c4ccccc4S(C)(=O)=O)cc3)cc2[nH]1] | A-1, C & E | ¹H NMR (300 MHz, DMSO-d₆): δ 13.9 (bs, 1H), 8.24-8.20 (m, 2H), 8.14-8.12 (d, J = 7.5 Hz, 1H), 7.86-7.68 (m, 4H), 7.56-7.54 (d, J = 8.1 Hz, 2H), 7.48-7.46 (d, J = 7.2 Hz, 1H), 2.90 (s, 3H), 2.71 (s, 3H).<br>MS m/z = 407 (M + H)⁺ |

TABLE II-continued

| Example No | Structure | General Procedure | Analytical data |
|---|---|---|---|
| 80 | 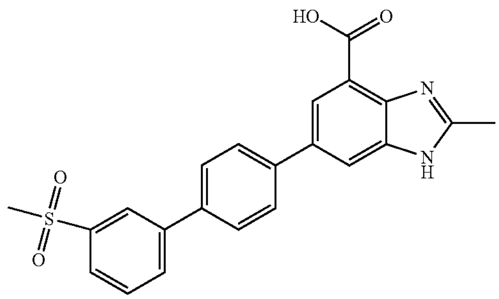 | A-1, C & E | $^1$H NMR (300 MHz, DMSO-d$_6$): δ 8.42-8.20 (m, 3H), 8.13-8.11(m, 1H), 7.92 (m, 5H), 7.81-7.78 (m, 1H), 3.32(s, 3H), 2.72 (s, 3H). (2H-Not revealed by $^1$H NMR). MS m/z = 407 (M + H)$^+$ |
| 81 | 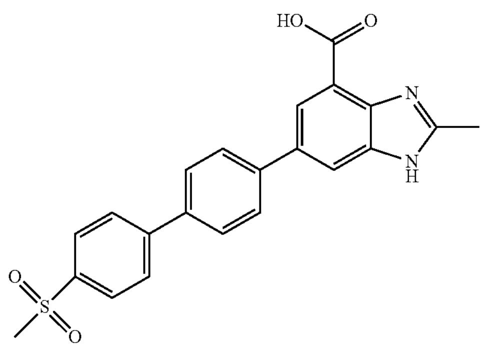 | A-1, C & E | $^1$H NMR (300 MHz, DMSO-d$_6$): δ 14.01 (bs, 1H), 8.26-8.25 (m, 2H), 8.03 (m, 4H), 7.93 (m, 4H), 3.28 (s, 3H), 2.79 (s, 3H). MS m/z = 407 (M + H)$^+$ |
| 82 | 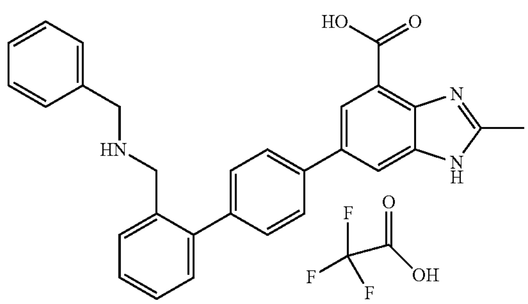 | A-1, B & E, G | $^1$H NMR (300 MHz, DMSO-d$_6$): δ 8.05-8.04 (m, 2H), 7.70-7.67 (m, 3H), 7.45-7.27 (m, 10H), 3.82-3.79 (d, J = 7.2 Hz, 4H), 3.16 (s, 2H), 2.58 (s, 3H). MS m/z = 448.2 (M + H)$^+$ |
| 83 | 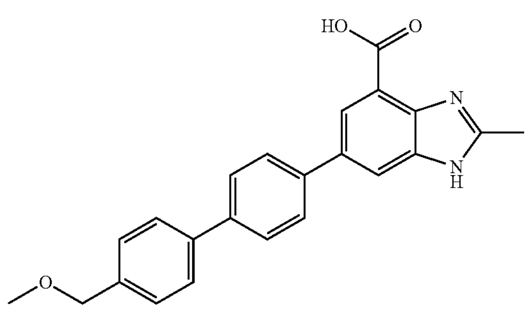 | A-1 & E | $^1$H NMR (300 MHz, DMSO-d$_6$): δ 13.8 (bs, 1H), 8.24-8.18 (m, 2H), 7.93-7.71 (m, 7H), 7.49-7.40 (m, 2H), 4.5 (s, 2H), 3.4 (s, 3H), 2.75(s, 3H). MS m/z = 371 (M − H)$^-$ |

TABLE II-continued

| Example No | Structure | General Procedure | Analytical data |
|---|---|---|---|
| 84 | 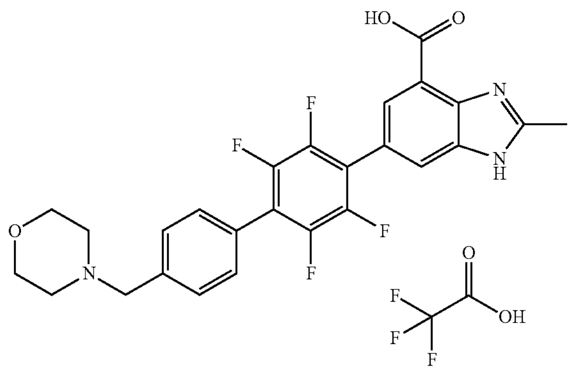 [SMILES: Cc1nc2c(C(=O)O)cc(-c3c(F)c(F)c(-c4ccc(CN5CCOCC5)cc4)c(F)c3F)cc2[nH]1 ; O=C(O)C(F)(F)F] | A-1 B & E, G | $^1$H NMR (300 MHz, DMSO-d$_6$): δ 13.6 (bs, 1H), 10.4 (bs, 1H), 8.17-8.05 (m, 2H), 7.75-7.71 (m, 4H), 4.47 (s, 2H), 3.96-3.70 (m, 4H), 3.39-3.17 (m, 4H), 2.74 (s, 3H). MS m/z = 498.1 (M − H)$^-$ |
| 85 | 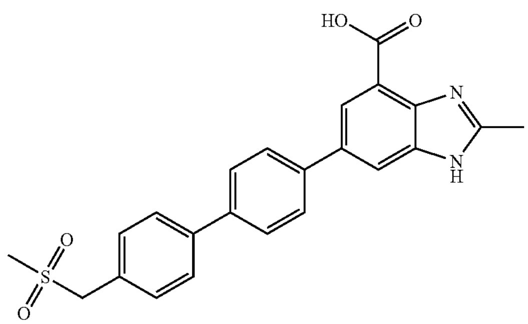 | A-1, C & E | $^1$H NMR (300 MHz, DMSO-d$_6$): δ 8.26-8.23 (m, 2H), 7.88-7.78 (m, 6H), 7.55-7.52 (m, 2H), 4.56 (s, 2H), 2.96 (s, 3H), 2.76 (s, 3H). (2H-Not revealed by $^1$H NMR). MS m/z = 419 (M − H)$^-$ |
| 86 | 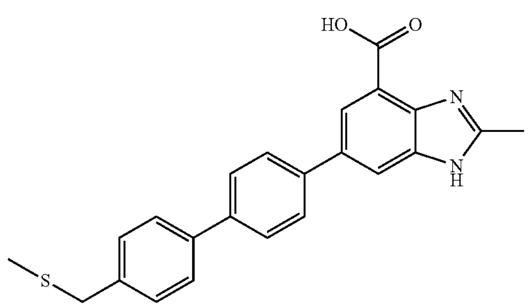 | A-1 & E | $^1$H NMR (300 MHz, DMSO-d$_6$): δ 8.21-8.18 (m, 2H), 7.84-7.83 (m, 7H), 7.44-7.41 (m, 2H), 2.72 (s, 3H), 2.08 (s, 3H), 1.99 (s, 2H). MS m/z = 389 (M − H)$^-$ |
| 87 | 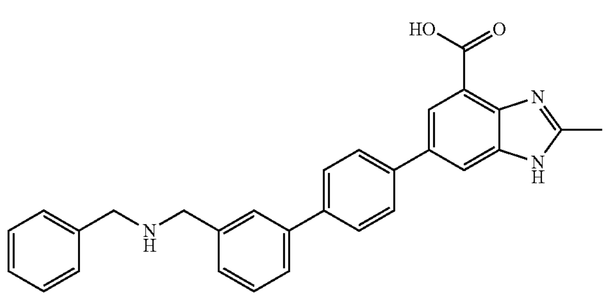 [SMILES: Cc1nc2c(C(=O)O)cc(-c3ccc(-c4cccc(CNCc5ccccc5)c4)cc3)cc2[nH]1] | A-1, B & E | $^1$H NMR (300 MHz, DMSO-d$_6$): δ 12.4 (bs, 1H), 10.01 (bs, 1H), 8.10-7.79 (m, 9H), 7.54-7.43 (m, 7H), 4.22-4.186 (m, 4H), 2.79 (s, 3H). MS m/z = 448.0 (M + H)$^+$ |

TABLE II-continued

| Example No | Structure | General Procedure | Analytical data |
|---|---|---|---|
| 88 | 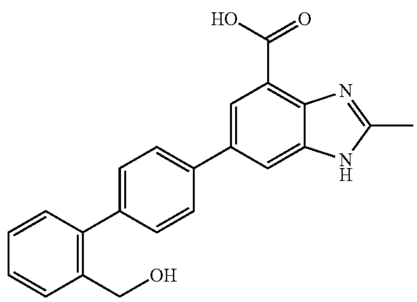 [SMILES: Cc1nc2c(C(=O)O)cc(-c3ccc(-c4ccccc4CO)cc3)cc2[nH]1] | A-1, B & E | ¹H NMR (300 MHz, DMSO-d$_6$): δ 12.22 (bs, 1H), 8.05 (m, 2H), 7.78-7.75 (d, J = 7.8 Hz, 2H), 7.61-7.58 (d, J = 7.2 Hz, 1H), 7.50-7.47 (m, 2H), 7.38-7.28 (m, 3H), 5.1 (m, 1H), 4.47 (m, 2H), 2.79 (s, 3H). MS m/z = 359.0 (M + H)⁺ |
| 89 | 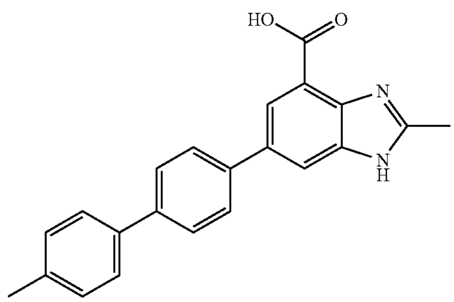 | A-1 & E | ¹H NMR (300 MHz, DMSO-d$_6$): δ 14.2 (bs, 1H), 8.27 (s, 2H), 7.88-7.80 (m, 4H), 7.66-7.63 (d, J = 7.5 Hz, 2H), 7.33-7.30 (d, J = 8.1 Hz, 2H), 2.82 (s, 3H), 2.36 (s, 3H). MS m/z = 341.1 (M + H)⁺ |
| 90 | 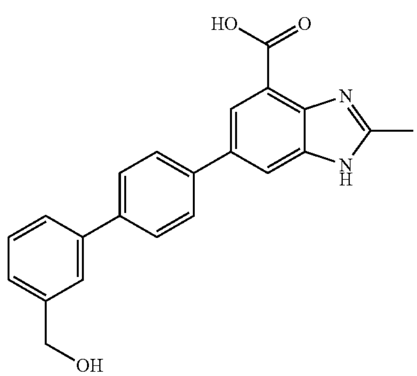 [SMILES: Cc1nc2c(C(=O)O)cc(-c3ccc(-c4cccc(CO)c4)cc3)cc2[nH]1] | A-1, B & E | ¹H NMR (300 MHz, DMSO-d$_6$): δ 13.5(bs, 1H), 8.2 (m, 2H), 7.9-7.75 (m, 4H), 7.7-7.6 (m, 2H), 7.50-7.4 (m, 1H), 7.4-7.3 (m, 1H), 5.3 (m, 1H), 4.6 (m, 2H), 2.7 (s, 3H). MS m/z = 359.1 (M + H)⁺ |
| 91 | 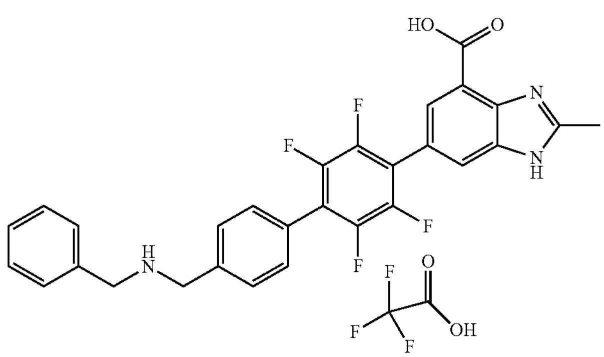 | A-1, B & E, G | ¹H NMR (300 MHz, DMSO-d$_6$): δ 8.25-8.05 (m, 2H), 7.75-7.25 (m, 10H), 4.4-4.29 (m, 4H), 2.9 (s, 3H). (2H-Not revealed by ¹H NMR). MS m/z = 519.9 (M + H)⁺ |

TABLE II-continued

| Example No | Structure | General Procedure | Analytical data |
|---|---|---|---|
| 92 | 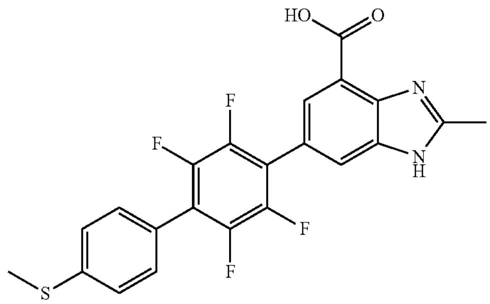 | A-2 & E | ¹H NMR (300 MHz, DMSO-d₆): δ 14.2 (bs, 1H), 8.25-8.15 (m, 2H), 7.6-7.4 (m, 4H), 2.9 (s, 3H), 2.62 (s, 3H). MS m/z = 447.0 (M + H)⁺ |
| 93 | 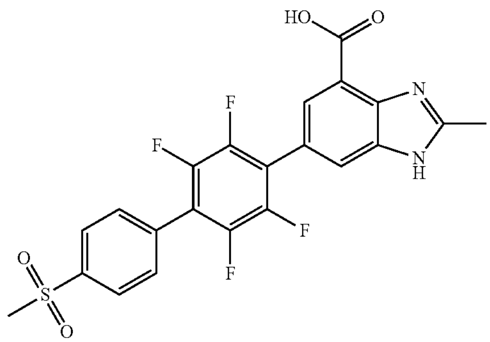 | A-2, C & E | ¹H NMR (300 MHz, DMSO-d₆): δ 8.2-8.05 (m, 2H), 8-7.74 (m, 4H), 3.2 (s, 3H), 2.7 (s, 3H). (2H-Not revealed by ¹H NMR). MS m/z = 479.0 (M + H)⁺ |
| 94 | 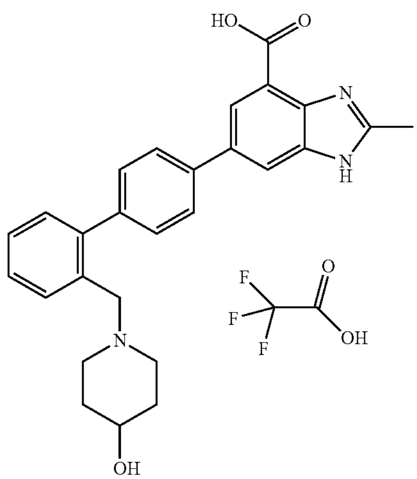 [SMILES: Cc1nc2c(C(=O)O)cc(-c3ccc(-c4ccccc4CN4CCC(O)CC4)cc3)cc2[nH]1 ; O=C(O)C(F)(F)F] | A-1, B & E, G | ¹H NMR (300 MHz, DMSO-d₆): δ 14 (bs, 1H), 9.62 (bs, 1H), 8.29-8.25 (d, J = 11.7 Hz, 2H), 7.91-7.85 (m, 3H), 7.56-7.42 (m, 5H), 4.37 (m, 2H), 3.83 (m, 1H), 3.52 (bs, 1H), 3.19 (m, 2H), 3.03 (m, 2H), 2.77 (m, 3H), 1.81-1.59 (m, 4H). MS m/z = 442.1 (M + H)⁺ |
| 95 | 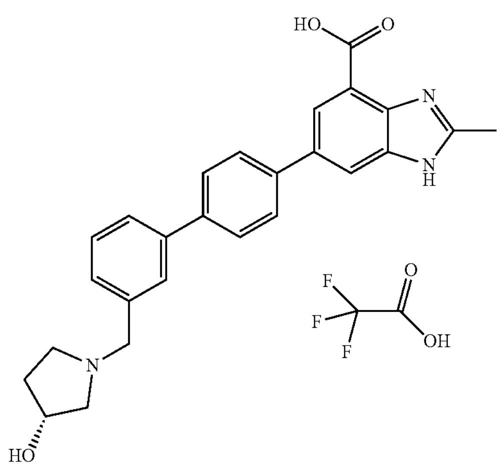 [SMILES: Cc1nc2c(C(=O)O)cc(-c3ccc(-c4cccc(CN5CC[C@@H](O)C5)c4)cc3)cc2[nH]1 ; O=C(O)C(F)(F)F] | A-1, B & E, G | ¹H NMR (300 MHz, CD₃OD): δ 8.42-8.21 (m, 2H), 7.84-7.56 (m, 8H), 4.57-4.54 (m, 3H), 3.55-3.312 (m, 3H), 2.92 (s, 3H), 2.34-2.10 (m, 3H). (3H-Not revealed by ¹H NMR). MS m/z = 428.0 (M + H)⁺ |

TABLE II-continued
| Example No | Structure | General Procedure | Analytical data |
|---|---|---|---|
| 96 | 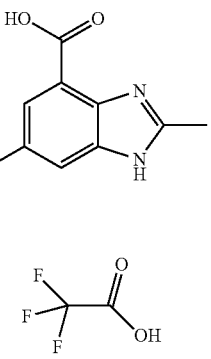 | A-1 & E, G | ¹H NMR (300 MHz, DMSO-$d_6$): δ 14.1(bs, 1H), 8.27 (m, 2H), 7.83-7.66 (m, 6H), 7.17 (m, 2H), 3.29 (m, 4H), 2.82 (s, 3H), 1.68-1.60 (m, 6H). MS m/z = 412 (M + H)⁺ |
| 97 | 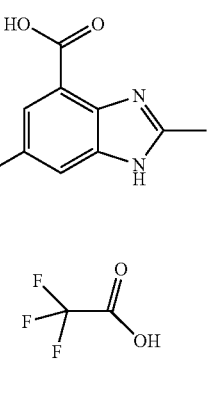 | A-1, B & E, G | ¹H NMR (300 MHz, DMSO-$d_6$): δ 13.9 (bs, 1H), 8.29-8.24 (m, 2H), 7.90-7.52 (m, 8H), 4.37 (s, 2H), 3.37 (m, 1H), 2.96-2.78 (m, 6H), 1.83-1.60 (m, 4H), 1.36-1.32 (m, 2H), 0.90 (s, 3H). MS m/z = 440 (M + H)⁺ |
| 98 | 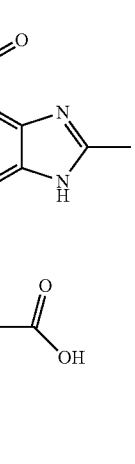 | A-1, B & E, G | ¹H NMR (300 MHz, DMSO-$d_6$): δ 9.0 (m, 2H), 8.26 (d, J = 8.1 Hz, 2H), 7.94-7.80 (m, 6H), 7.61-7.51 (m, 2H), 4.26 (m, 2H), 3.55 (m, 1H), 2.78 (s, 3H), 2.05-1.99 (m, 2H), 1.73-1.56 (m, 6H). MS m/z = 426 (M + H)⁺ |

TABLE II-continued

| Example No | Structure | General Procedure | Analytical data |
|---|---|---|---|
| 99 | 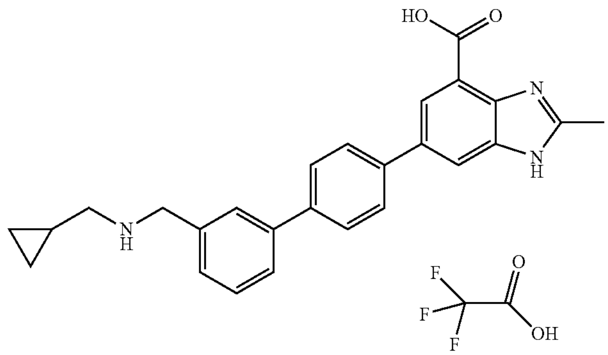 [SMILES: Cc1nc2c(C(=O)O)cc(-c3ccc(-c4cccc(CNCC5CC5)c4)cc3)cc2[nH]1 ; O=C(O)C(F)(F)F] | A-1, B & E, G | ¹H NMR (300 MHz, DMSO-d₆): δ 13.9 (s, 1H), 9.02 (m, 2H), 8.28-8.25 (m, 2H), 7.92-7.52 (m, 8H), 4.27 (m, 2H), 2.90-2.78 (m, 6H), 1.09 (m, 1H), 0.62 (m, 2H), 0.38 (m, 1H). MS m/z = 412 (M + H)⁺ |
| 100 | 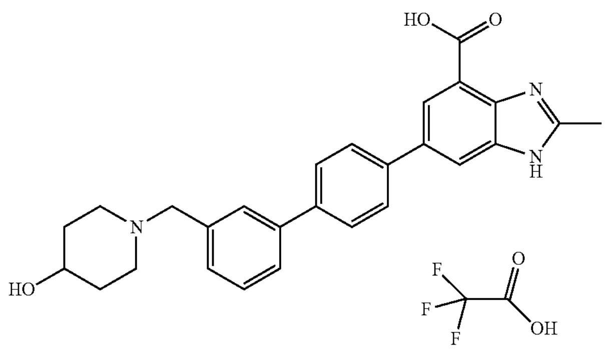 [SMILES: Cc1nc2c(C(=O)O)cc(-c3ccc(-c4cccc(CN5CCC(O)CC5)c4)cc3)cc2[nH]1 ; O=C(O)C(F)(F)F] | A-1, B & E, G | ¹H NMR (300 MHz, DMSO-d₆): δ 14.01 (bs, 1H), 9.64 (bs, 1H), 8.29-8.26 (m, 2H), 7.91-7.58 (m, 7H), 4.42 (s, 2H), 3.96 (m, 1H), 3.38-3.22 (m, 4H), 3.06-3.02 (m, 2H), 2.79 (s, 3H), 1.97-1.80 (m, 3H), 1.59 (m, 1H). MS m/z = 442 (M + H)⁺ |
| 101 | 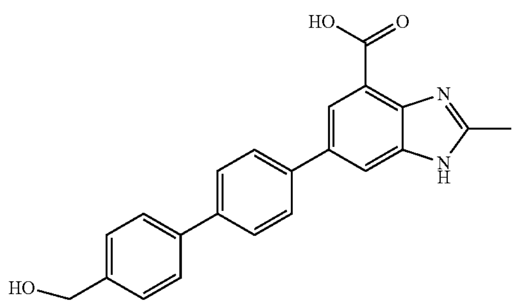 [SMILES: Cc1nc2c(C(=O)O)cc(-c3ccc(-c4ccc(CO)cc4)cc3)cc2[nH]1] | A-1, B & E | ¹H NMR (300 MHz, DMSO-d₆): δ 13.2 (bs, 1H), 8.32 (m, 2H), 7.9-7.7 (m, 6H), 7.45 (m, 2H), 4.52 (m, 2H), 2.79 (s, 3H). (2H-Not revealed by ¹H NMR). MS m/z = 359 (M + H)⁺ |
| 102 | 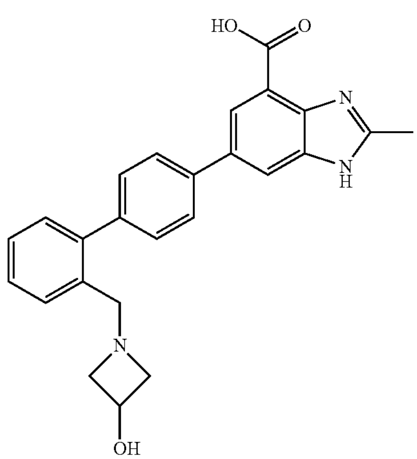 [SMILES: Cc1nc2c(C(=O)O)cc(-c3ccc(-c4ccccc4CN4CC(O)C4)cc3)cc2[nH]1] | A-1, B & E | ¹H NMR (300 MHz, DMSO-d₆): δ 14.01 (bs, 1H), 11.48 (bs, 1H), 8.27 (s, 2H), 7.95-7.80 (m, 3H), 7.60-7.39 (m, 5H), 4.50-4.45 (m, 2H), 4.2 (m, 2H), 3.95 (m, 2H), 3.62 (m, 2H), 2.85 (s, 3H). MS m/z = 414 (M + H)⁺ |

TABLE II-continued
| Example No | Structure | General Procedure | Analytical data |
|---|---|---|---|
| 103 | 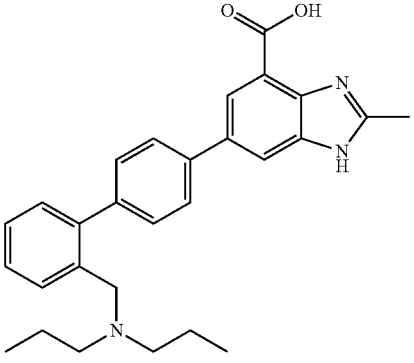 [SMILES: CCCN(CCC)Cc1ccccc1-c1ccc(-c2cc(C(=O)O)c3nc(C)[nH]c3c2)cc1] | A-1, B & E | $^1$H NMR (300 MHz, DMSO-d$_6$): δ 13.9 (bs, 1H), 10.88 (bs, 1H), 8.26 (s, 2H), 8.15-8.13 (m, 1H), 7.91 (d, J = 8.1 Hz, 2H), 7.54-7.40 (m, 5H), 4.38 (s, 2H), 2.82 (s, 3H), 2.71-2.63 (m, 4H), 1.53-1.35 (m, 4H), 1.09-0.70 (m, 6H). MS m/z = 442(M + H)$^+$ |
| 104 | 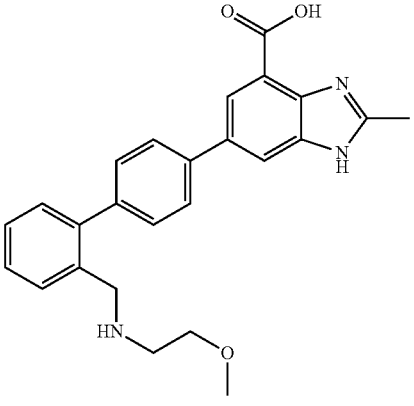 [SMILES: COCCNCc1ccccc1-c1ccc(-c2cc(C(=O)O)c3nc(C)[nH]c3c2)cc1] | A-1, B & E | $^1$H NMR (300 MHz, DMSO-d$_6$): δ 13.9 (bs, 1H), 9.69 (m, 2H), 8.26 (s, 2H), 7.99-7.97 (m, 1H), 7.89 (d, J = 8.4 Hz, 2H), 7.57-7.36 (m, 5H), 4.16 (m, 2H), 3.56-3.54 (m, 2H), 3.16 (s, 3H), 2.97 (m, 2H), 2.81 (s, 3H). MS m/z = 416(M + H)$^+$ |
| 105 | 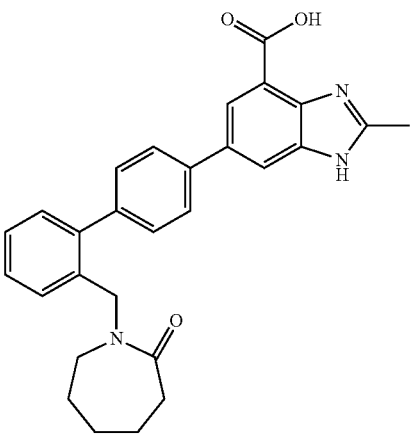 [SMILES: Cc1nc2c(C(=O)O)cc(-c3ccc(-c4ccccc4CN4CCCCCC4=O)cc3)cc2[nH]1] | A-1, B & E | $^1$H NMR (300 MHz, CD$_3$OD): δ 8.43-8.20 (m, 2H), 7.80 (m, 2H), 7.42-7.27 (m, 6H), 3.21 (m, 2H), 2.89 (s, 3H), 2.50 (s, 2H), 1.64-1.43 (m, 8H). (2H-Not revealed by $^1$H NMR). MS m/z = 454(M + H)$^+$ |

TABLE II-continued

| Example No | Structure | General Procedure | Analytical data |
|---|---|---|---|
| 106 | 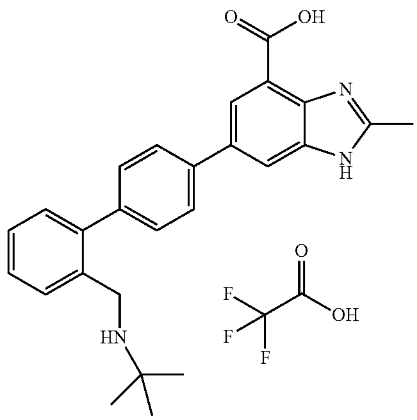 | A-1, B & E, G | ¹H NMR (300 MHz, CD₃OD): δ 8.43 (s, 1H), 8.22 (s, 1H), 7.89 (d, J = 8.1 Hz, 2H), 7.69-7.68 (m, 1H), 7.57-7.46 (m, 5H), 4.24 (m, 2H), 2.91 (s, 3H), 1.22 (s, 9H). (3H-Not revealed by ¹H NMR). MS m/z = 414(M + H)⁺ |
| 107 | 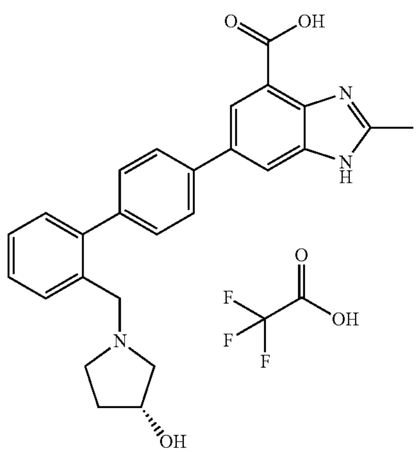 [SMILES: Cc1nc2c(C(=O)O)cc(-c3ccc(-c4ccccc4CN4CC[C@@H](O)C4)cc3)cc2[nH]1 ; O=C(O)C(F)(F)F] | A-1, B & E, G | ¹H NMR (300 MHz, DMSO-d₆): δ 13.9(bs, 1H), 8.31-8.23(m, 2H), 7.95-7.41(m, 8H), 4.53-4.29(m, 5H), 3.11-2.77(m, 6H), 1.72(m, 2H). MS m/z = 428(M + H)⁺ |
| 108 | 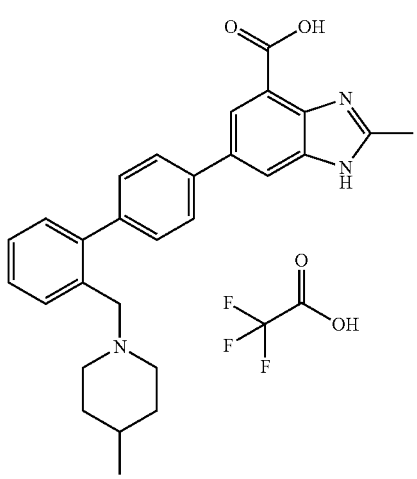 [SMILES: Cc1nc2c(C(=O)O)cc(-c3ccc(-c4ccccc4CN4CCC(C)CC4)cc3)cc2[nH]1 ; O=C(O)C(F)(F)F] | A-1, B & E, G | ¹H NMR (300 MHz, CD₃OD): δ 8.45 (s, 1H), 8.23 (s, 1H), 7.90 (m, 2H), 7.72 (m, 1H), 7.58-7.52 (m, 5H), 4.42 (s, 2H), 2.90 (s, 3H), 2.66 (m, 2H), 1.77-1.56 (m, 4H), 1.38-1.35 (m, 3H), 0.92 (m, 3H). (2H-Not revealed by ¹H NMR). MS m/z = 440(M + H)⁺ |

TABLE II-continued

| Example No | Structure | General Procedure | Analytical data |
|---|---|---|---|
| 109 | 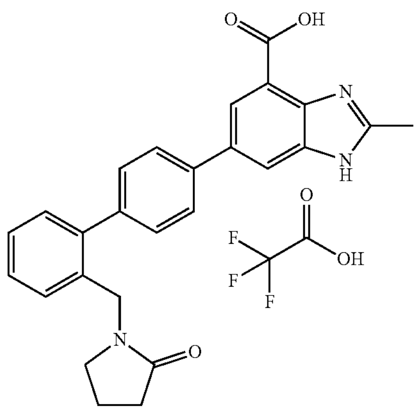 | A-1 & B, E, G | ¹H NMR (300 MHz, DMSO-d$_6$): δ 8.21 (d, J = 13.2 Hz, 2H), 7.84 (m, 2H), 7.49 (m, 2H), 7.39 (m, 2H), 7.31 (m, 2H), 4.41 (s, 2H), 3.10 (m, 2H), 2.72 (s, 3H), 2.20 (m, 2H), 1.86 (m, 2H). (2H-Not revealed by ¹H NMR). MS m/z = 425.9 (M + H)$^+$ |
| 110 | 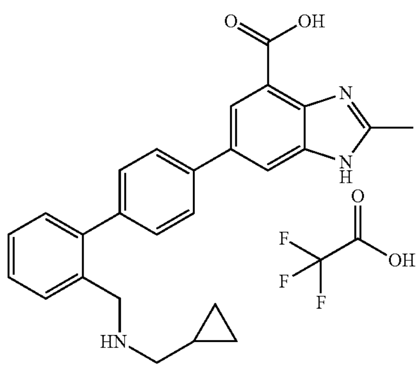 | A-1 & B, E, G | ¹H NMR (300 MHz, DMSO-d$_6$): δ 13.9 (bs, 1H), 9.10 (s, 2H), 8.27 (d, J = 14.8 Hz, 2H), 7.91 (d, J = 10.4 Hz, 2H), 7.77 (s, 1H), 7.55 (m, 4H), 7.42 (s, 1H), 4.20 (s, 2H), 2.76 (m, 5H), 0.95 (m, 1H), 0.50 (m, 2H), 0.28 (m, 2H). MS m/z = 412.1 (M + H)$^+$ |
| 111 | 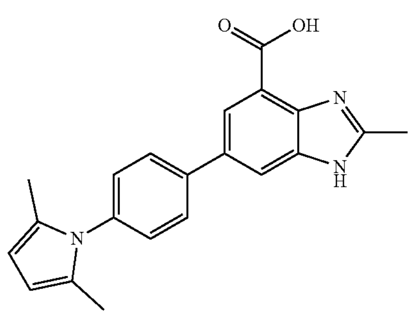 [SMILES: Cc1nc2c(C(=O)O)cc(-c3ccc(-n4c(C)ccc4C)cc3)cc2[nH]1] | A-2 & E | ¹H NMR (300 MHz, DMSO-d$_6$): δ 13.41 (bs, 1H), 12.25 (bs, 1H), 8.11-8.04 (m, 2H), 7.85 (d, J = 8.4 Hz, 2H), 7.36 (d, J = 10.4 Hz, 2H) 5.82 (s, 2H), 2.57 (s, 3H), 2.02 (s, 6H). MS m/z = 346.0 (M + H)$^+$ |
| 112 | 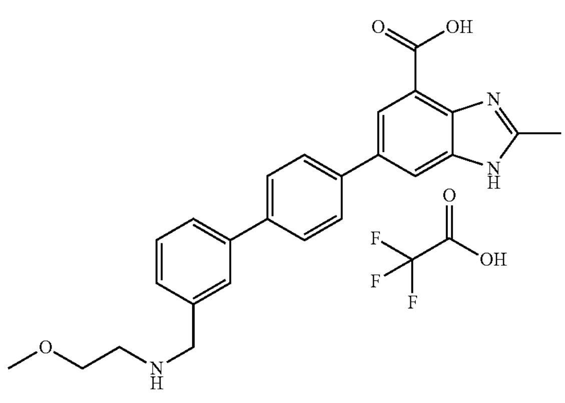 | A-1, B & E, G | ¹H NMR (300 MHz, DMSO-d$_6$): δ 8.31 (s, 2H), 7.92-7.82 (m, 6H), 7.60 (m, 2H), 4.26 (s, 2H), 3.87 (s, 3H) 3.33 (m, 2H), 2.84 (m, 2H), 2.54 (s, 3H). (3H-Not revealed by ¹H NMR). MS m/z = 416.1 (M + H)$^+$ |

TABLE II-continued

| Example No | Structure | General Procedure | Analytical data |
|---|---|---|---|
| 113 | 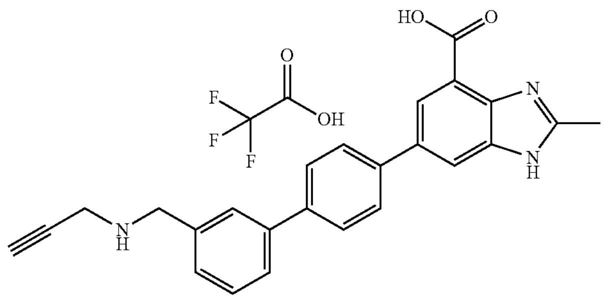 | A-1, B & E, G | ¹H NMR (300 MHz, DMSO-d₆): δ 9.59 (bs, 1H), 8.21 (d, J = 14.8, 2H), 7.91-7.80 (m, 6H), 7.59-7.46 (m, 2H), 4.29 (s, 2H), 3.98 (s, 2H), 2.70 (s, 3H). (3H-Not revealed by ¹H NMR). MS m/z = 395.9 (M + H)⁺ |
| 114 | 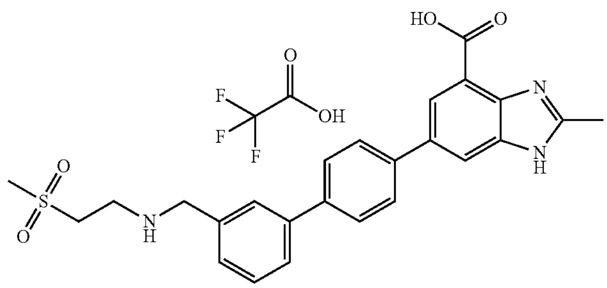 | A-1, B & E, G | ¹H NMR (300 MHz, DMSO-d₆): δ 13.95 (bs, 1H), 9.27 (bs, 1H), 8.28 (m, 2H), 7.94-7.82 (m, 6H), 7.62-7.50 (m, 2H), 4.33 (s, 2H), 3.61 (m, 2H), 3.47 (m, 2H), 3.15 (s, 3H), 2.77 (s, 3H). MS m/z = 464.0 (M + H)⁺ |
| 115 | 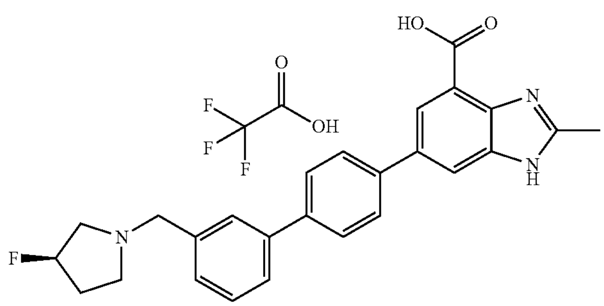 | A-1, B & E, G | ¹H NMR (300 MHz, CD₃OD): δ 8.44 (m, 1H), 8.22 (m, 1H), 7.91-7.85 (m, 6H), 7.65-7.54 (m, 2H), 5.56-5.38 (m, 1H), 4.56 (s, 2H), 3.70-3.55 (m, 4H), 2.92 (m, 3H), 2.39 (m, 2H). (2H-Not revealed by ¹H NMR). MS m/z = 430.1 (M + H)⁺ |
| 116 | 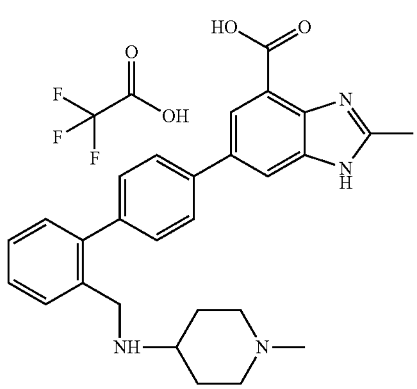 | A-1, B & E, G | ¹H NMR (300 MHz, DMSO-d₆): δ 13.95 (bs, 1H), 9.95 (bs, 1H), 9.38 (m, 2H), 8.31 (m, 2H), 7.92-7.75 (m, 3H), 7.55-7.42 (m, 5H), 4.22 (s, 2H), 3.47 (m, 2H), 3.21 (m, 2H), 2.79 (s, 3H), 2.71 (s, 3H), 2.09 (m, 2H), 1.78 (m, 2H). MS m/z = 455.2 (M + H)⁺ |

TABLE II-continued

| Example No | Structure | General Procedure | Analytical data |
|---|---|---|---|
| 117 | 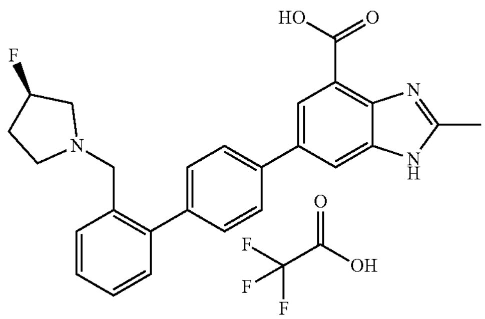 | A-1, B & E, G | $^1$H NMR (300 MHz, CD$_3$OD): δ 8.46 (s, 1H), 8.25 (s, 1H), 7.95-7.90 (m, 2H), 7.75-7.48 (m, 6H), 5.39-5.21 (m, 1H), 4.61 (s, 2H), 3.00-2.87 (m 6H), 2.32-2.18(m, 2H). (2H-Not revealed by $^1$H NMR). MS m/z = 430.0 (M + H)$^+$ |
| 118 | 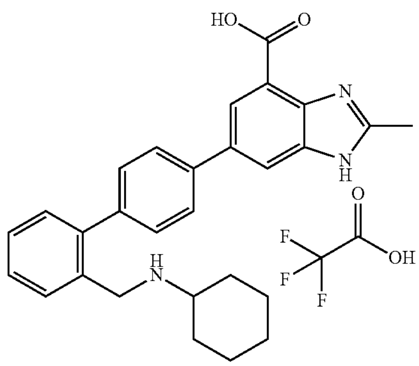 | A-1, B & E, G | $^1$H NMR (300 MHz, DMSO-d$_6$): δ 13.9 (bs, 1H), 8.80 (m, 2H), 8.26 (d, J = 7.8 Hz, 2H), 7.92 (d, J = 7.8 Hz, 2H), 7.73 (m, 1H), 7.56-7.42 (m, 5H), 4.18 (s, 2H) 2.87-2.75 (m, 4H), 1.82-1.52 (m, 5H), 1.22-1.06 (m, 5H). MS m/z = 440.1 (M + H)$^+$ |
| 119 | 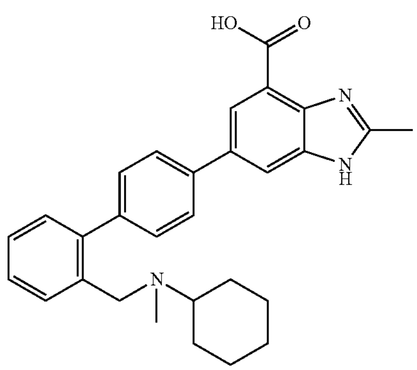 [SMILES: Cc1nc2c(C(=O)O)cc(-c3ccc(-c4ccccc4CN(C)C4CCCCC4)cc3)cc2[nH]1] | A-1, B & E | $^1$H NMR (300 MHz, CD$_3$OD): δ 8.46 (s, 1H), 8.26 (s, 1H), 7.94 (d, J = 7.8 Hz , 2H), 7.74-7.49 (m, 6H), 4.70 (m, 1H), 4.30 (m, 1H), 2.94 (m, 4H), 2.62 (s, 3H), 1.85-1.62 (m, 4H), 1.43-1.15 (m, 6H). (2H-Not revealed by $^1$H NMR). MS m/z = 454.1 (M + H)$^+$ |
| 120 | 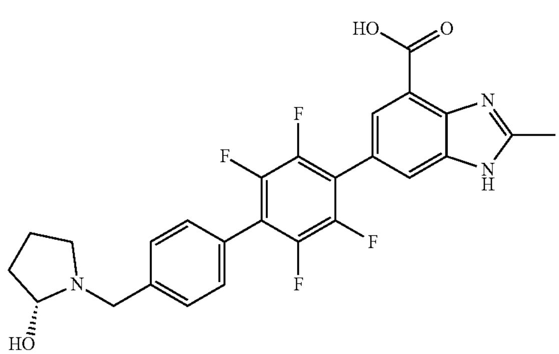 [SMILES: Cc1nc2c(C(=O)O)cc(-c3c(F)c(F)c(-c4ccc(CN5CCC[C@H]5O)cc4)c(F)c3F)cc2[nH]1] | A-2, B & E | $^1$H NMR (300 MHz, DMSO-d$_6$): δ 13.1 (bs, 1H), 11.62 (bs, 1H), 8.11 (m, 2H), 7.86 (m, 2H), 7.68 (m, 2H), 5.63 (bs, 1H), 4.45 (s, 2H), 3.392-3.02 (m, 4H), 2.70 (m, 4H), 1.98 (m, 2H). MS m/z = 499.9 (M + H)$^+$ |

TABLE II-continued

| Example No | Structure | General Procedure | Analytical data |
|---|---|---|---|
| 121 | 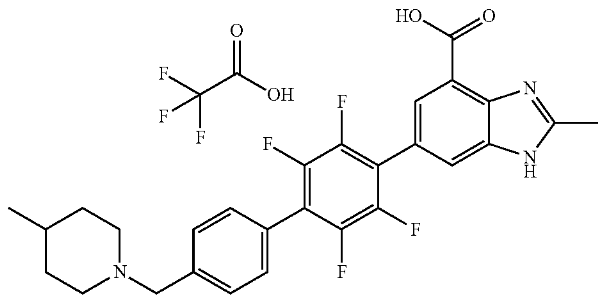 | A-2, B & E, G | ¹H NMR (300 MHz, CD₃OD): δ 8.23 (m, 2H), 7.72 (m, 4H), 4.40 (s, 2H), 3.55 (m, 2H), 3.06 (m, 4H), 1.97-1.92 (m, 3H), 1.46-1.39 (m, 3H), 1.03 (m, 3H). (2H-Not revealed by ¹HNMR). MS m/z = 512.1 (M + H)⁺ |
| 122 | 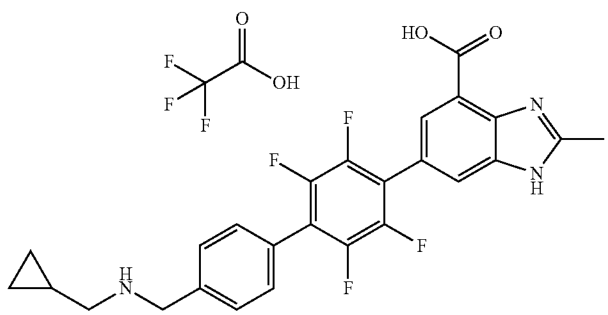 [SMILES: Cc1nc2c(C(=O)O)cc(-c3c(F)c(F)c(-c4ccc(CNCC5CC5)cc4)c(F)c3F)cc2[nH]1 ; O=C(O)C(F)(F)F] | A-2, B & E, G | ¹H NMR (300 MHz, CD₃OD): δ 8.19 (m, 2H), 7.70 (m, 4H), 4.33 (s, 2H), 3.03 (m, 2H), 2.83 (s, 3H), 1.15 (m, 1H), 0.76 (m, 2H), 0.45 (m, 2H). (3H-Not revealed by ¹H NMR). MS m/z = 484.1 (M + H)⁺ |
| 123 | 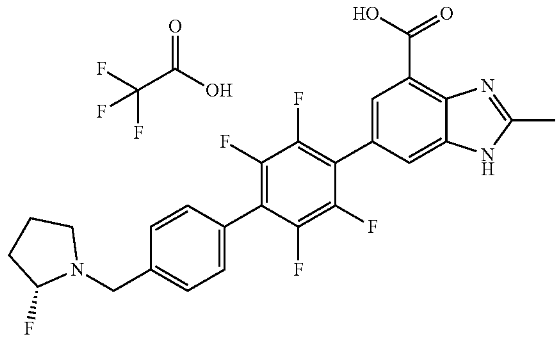 | A-2, B & E, G | ¹H NMR (300 MHz, CD₃OD): δ 8.26 (m, 2H), 7.74 (m, 4H), 5.58 (m, 1H), 4.57 (s, 2H), 3.73 (m 2H), 2.89(s, 3H), 2.48-2.42(m, 2H), 1.40 (s, 2H). (2H-Not revealed by ¹H NMR). MS m/z = 502.1 (M + H)⁺ |
| 124 | 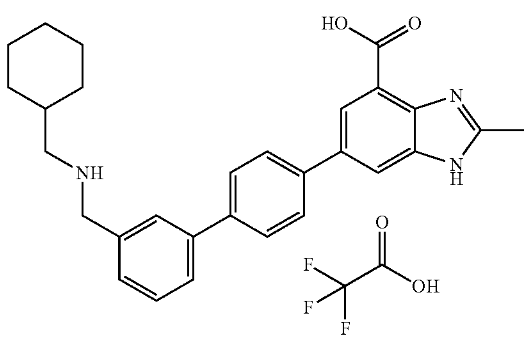 | A-1, B & E, G | ¹H NMR (300 MHz, CD₃OD): δ 8.45 (m, 2H), 7.86-7.81 (m, 6H), 7.63-7.45 (m, 2H), 4.32 (s, 2H), 2.96-2.92 (m, 5H), 1.81-1.78 (m, 5H), 1.36-1.04 (m, 6H). (3H-Not revealed by ¹H NMR). MS m/z = 454.1 (M + H)⁺ |

TABLE II-continued

| Example No | Structure | General Procedure | Analytical data |
|---|---|---|---|
| 125 | 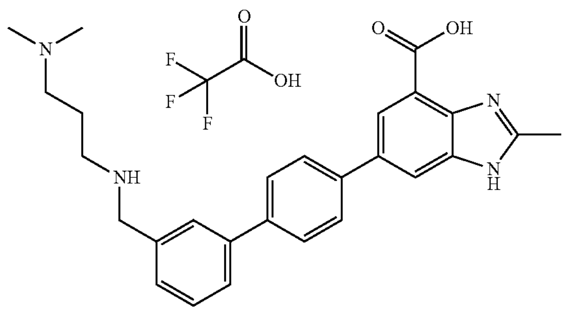 | A-2, B & E, G | ¹H NMR (300 MHz, DMSO-d₆): δ 13.9 (bs, 1H), 9.87 (bs, 1H), 9.14 (s, 1H), 8.26 (m, 2H), 7.90-7.81 (m, 5H), 7.59 (m, 3H), 4.28 (s, 2H), 3.14-3.06 (m, 5H), 2.78-2.50 (m, 8H), 2.03 (m, 2H). MS m/z = 443.1 (M + H)⁺ |
| 126 | 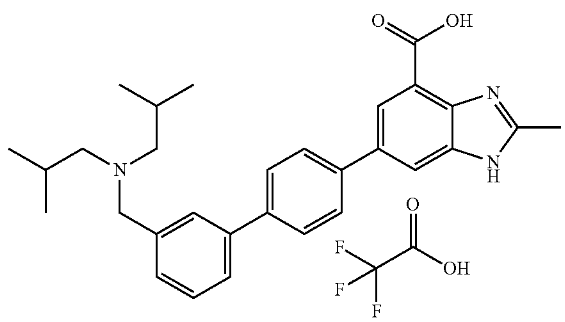 | A-1, B & E, G | ¹H NMR (300 MHz, DMSO-d₆): δ 13.8 (bs, 1H), 8.82 (m, 1H), 8.26 (d, J = 9.9 Hz , 2H), 7.99-7.85 (m, 6H), 7.62 (m, 2H), 4.48 (s, 2H), 2.96-2.88 (m, 4H), 2.75 (s, 3H), 2.26 (m, 2H), 1.23-0.94 (m, 12H). MS m/z = 470.0 (M + H)⁺ |
| 127 | 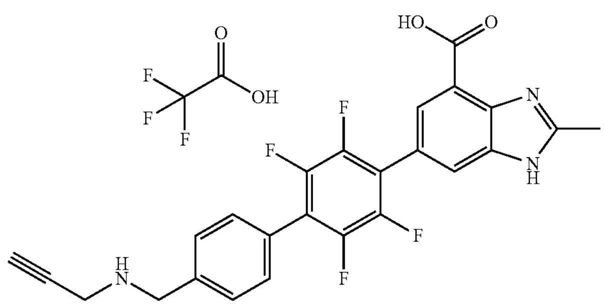 | A-2, B & E, G | ¹H NMR (300 MHz, CD₃OD): δ 8.15 (m, 2H), 7.70 (m, 4H), 4.83 (s, 1H), 4.40 (s, 2H), 4.03 (s, 2H), 2.79 (s, 3H). (3H-Not revealed by ¹H NMR). MS m/z = 468.0 (M + H)⁺ |
| 128 | 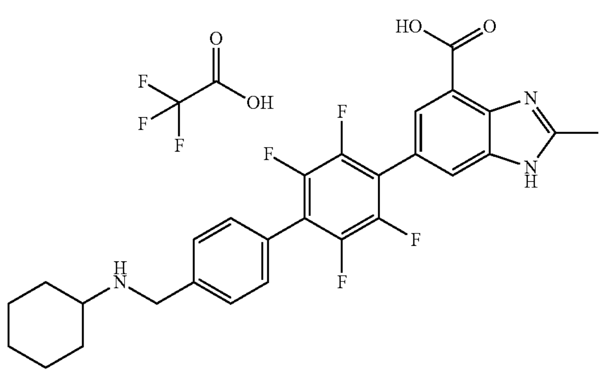 | A-2, B & E, G | ¹H NMR (300 MHz, DMSO-d₆): δ 13.6 (bs, 1H), 12.6 (bs, 1H), 8.81 (bs, 1H), 7.99-7.71 (m, 6H), 4.28 (s, 2H), 2.71 (s, 3H), 1.82-1.66 (m, 4H), 1.2-1.24 (m 7H). MS m/z = 512.0 (M + H)⁺ |

TABLE II-continued

| Example No | Structure | General Procedure | Analytical data |
|---|---|---|---|
| 129 | 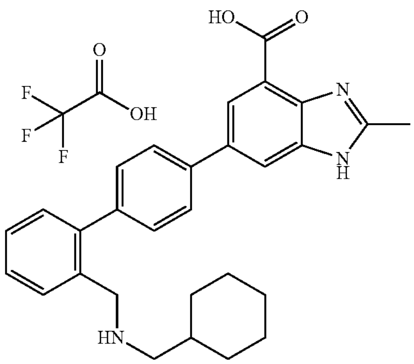 | A-1, B & E, G | $^1$H NMR (300 MHz, DMSO-d$_6$): δ 8.78 (m, 2H), 8.25 (d, J = 8.4 Hz, 2H), 7.90-7.73 (m, 3H), 7.55-7.40 (m, 5H), 4.18 (s, 2H), 2.75-2.65 (m, 5H), 1.62-1.59(m, 6H), 1.11-0.81(m, 5H). MS m/z = 454.2 (M + H)$^+$ |
| 130 | 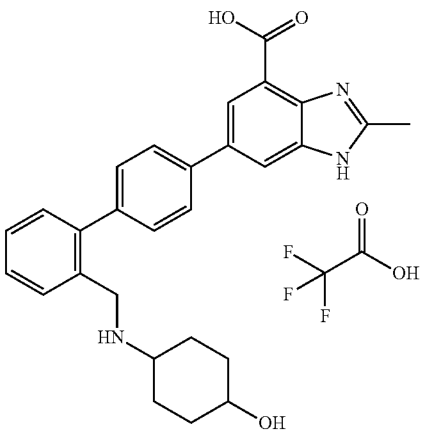 | A-1, B & E, G | $^1$H NMR (300 MHz, DMSO-d$_6$): δ 14.2 (bs, 1H), 9.19 (m, 2H), 8.31 (m, 2H), 7.94 (m, 3H), 7.58-7.40 (m, 5H), 4.13 (s, 2H), 3.392-3.28 (m, 2H), 2.83 (m, 4H), 1.79-174 (m, 4H), 1.37 (m, 2H), 1.11 (m, 2H). MS m/z = 456.1 (M + H)$^+$ |
| 131 | 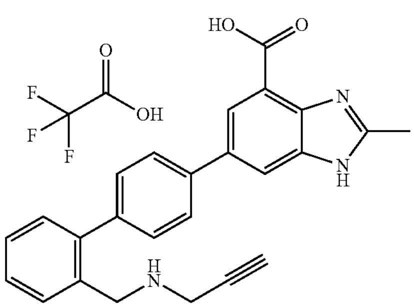 | A-1, B & E, G | $^1$H NMR (300 MHz, CD$_3$OD): δ 8.44 (s, 1H), 8.22 (s, 1H), 7.90-7.87 (m, 2H), 7.66-7.45 (m, 6H), 4.41 (s, 2H), 3.86 (s, 2H), 3.121 (s, 1H), 2.90 (s, 3H). (3H-Not revealed by $^1$H NMR). MS m/z = 395.9 (M + H)$^+$ |
| 132 | 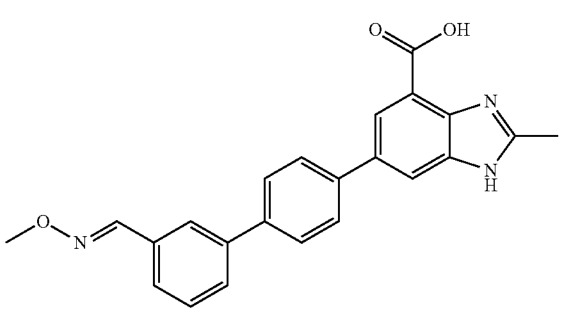 | A-1, B & E | $^1$H NMR (300 MHz, DMSO-d$_6$): δ 8.34-8.22 (m, 3H), 7.96-7.55 (m, 8H), 3.93 (s, 3H), 2.75 (s, 3H). (2H-Not revealed by $^1$H NMR). MS m/z = 386.1(M + H)$^+$ |

TABLE II-continued

| Example No | Structure | General Procedure | Analytical data |
|---|---|---|---|
| 133 | [structure] | A-1, B & E, G | ¹H NMR (300 MHz, DMSO-d$_6$): δ 13.85(bs, 1H), 9.79 (bs, 1H), 9.13 (bs, 2H), 8.27-8.23 (d, J = 13.2 Hz, 2H), 7.91-7.88 (d, J = 8.4 Hz, 2H), 7.73-7.71 (m, 1H), 7.55-7.44 (m, 5H), 4.20 (m, 2H), 3.07 (m, 2H), 2.94 (m, 2H), 2.76-2.74 (m, 8H), 1.95-1.92 (m, 2H). MS m/z = 443.2(M + H)⁺. |
| 134 | [structure] | A-2 & E | ¹H NMR (300 MHz, DMSO-d$_6$): δ 14.00 (bs, 1H), 7.73-7.58 (m, 5H), 7.42-7.38 (m, 2H), 5.69 (s, 2H), 2.76 (s, 3H), 1.80 (s, 6H). MS m/z = 346.0(M + H)⁺. |
| 135 | [structure] | A-1, B & E, G | ¹H NMR (300 MHz, DMSO-d$_6$): δ 8.31-8.29 (d, J = 5.4 Hz, 2H), 7.94-7.85 (m, 5H), 7.77-7.74 (m, 1H), 7.56-7.45 (m, 2H), 4.17 (s, 2H), 3.80-3.76 (m, 2H), 2.82 (s, 3H). (3H-Not revealed by ¹H NMR). MS m/z = 440.1(M + H)⁺. |

TABLE II-continued
| Example No | Structure | General Procedure | Analytical data |
|---|---|---|---|
| 136 | 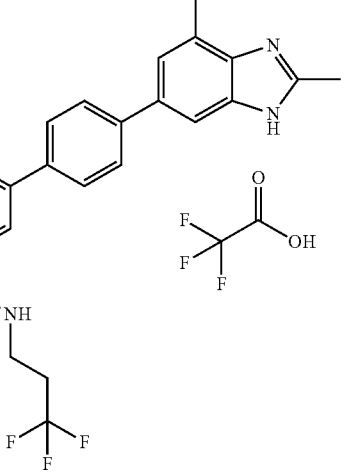 | A-1, B & E, G | ¹H NMR (300 MHz, DMSO-d$_6$): δ 9.30(bs, 2H), 8.31-8.28(d, J = 9.9 Hz, 2H), 7.95-7.83(m, 6H), 7.62-7.50(m, 2H), 4.33(s, 2H), 3.29(m, 2H), 2.81-2.74(m, 5H). MS m/z = 453.9(M + H)⁺. |
| 137 | 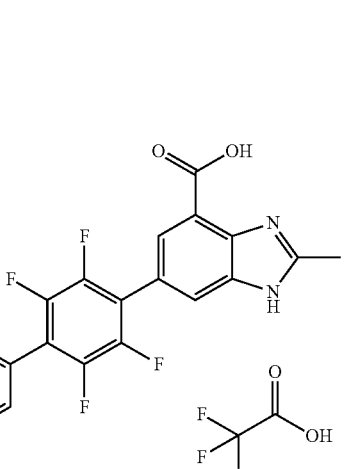 | A-2, B, C & E, G | ¹H NMR (300 MHz, DMSO-d$_6$): δ 14.00 (bs, 1H), 8.20 (s, 1H), 8.08 (s, 1H), 7.59-7.55 (m, 4H), 3.96 (s, 2H), 3.21-3.16 (m, 4H), 3.03 (m, 4H), 2.76 (s, 3H). MS m/z = 548.0(M + H)⁺. |
| 138 | 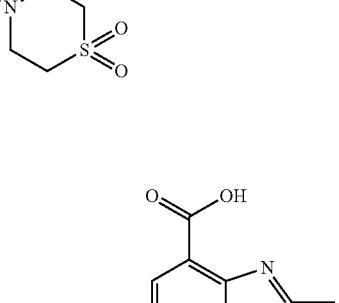 | A-2 & E, G | ¹H NMR (300 MHz, DMSO-d$_6$): δ 14.00 (bs, 1H), 8.33-8.29 (d, J = 11.1 Hz, 2H), 7.93-7.90 (d, J = 8.4 Hz, 2H), 7.69-7.66 (d, J = 8.4 Hz, 2H), 6.13 (s, 1H), 2.84(s, 3H), 2.38(s, 3H), 2.22(s, 3H). MS m/z = 347.0(M + H)⁺. |

TABLE II-continued

| Example No | Structure | General Procedure | Analytical data |
|---|---|---|---|
| 139 | 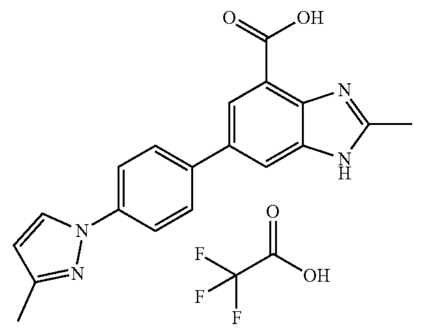 | A-2 & E, G | ¹H NMR (300 MHz, DMSO-d₆): δ 13.85 (bs, 1H), 8.47 (s, 1H), 8.20-8.19 (m, 2H), 7.94-7.84 (m, 4H), 6.38 (s, 1H), 2.71 (s, 3H), 2.29 (s, 3H). MS m/z = 332.9(M + H)⁺. |
| 140 | 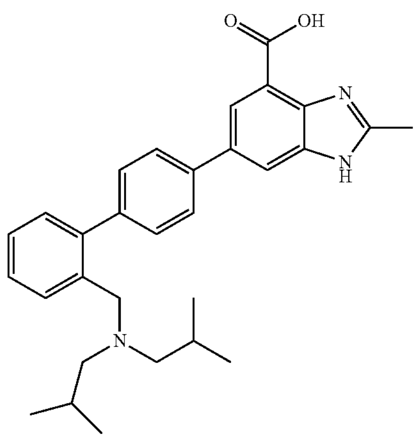 [SMILES: Cc1nc2c(C(=O)O)cc(-c3ccc(-c4ccccc4CN(CC(C)C)CC(C)C)cc3)cc2[nH]1] | A-1, B & E | ¹H NMR (300 MHz, CD₃OD): δ 8.37 (s, 1H), 8.19 (s, 1H), 7.93-7.91 (m, 2H), 7.73-7.50 (m, 6H), 4.64 (s, 2H), 2.84-2.78 (m, 7H), 1.94-1.90 (m, 2H), 0.88-0.86 (m, 12H). (2H-Not revealed by ¹H NMR). MS m/z = 470.2(M + H)⁺. |
| 141 | 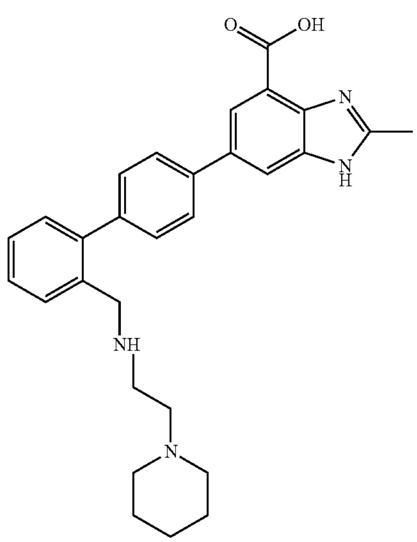 [SMILES: Cc1nc2c(C(=O)O)cc(-c3ccc(-c4ccccc4CNCCN4CCCCC4)cc3)cc2[nH]1] | A-1, B & E | ¹H NMR (300 MHz, DMSO-d₆): δ 13.80(bs, 1H), 9.40-9.30(m, 2H), 8.26-8.22(m, 2H), 7.91-7.88(m, 2H), 7.69-7.68(m, 1H), 7.57-7.42(m, 5H), 4.25(s, 2H), 3.39-3.34(m, 6H), 2.91-2.75(m, 5H), 1.77-1.63(m, 2H), 1.60 (m, 4H). MS m/z = 469.2(M + H)⁺. |

TABLE II-continued

| Example No | Structure | General Procedure | Analytical data |
|---|---|---|---|
| 142 | 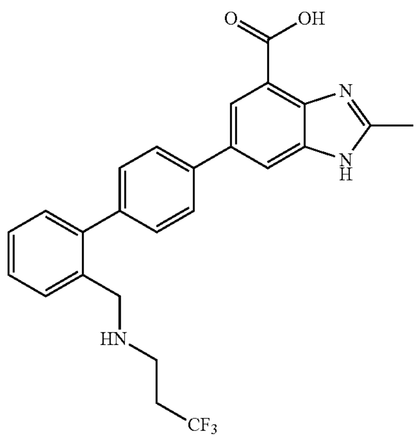 [SMILES: Cc1nc2c(C(=O)O)cc(-c3ccc(-c4ccccc4CNCCC(F)(F)F)cc3)cc2[nH]1] | A-1, B & E | ¹H NMR (300 MHz, CD$_3$OD): δ 8.45 (s, 1H), 8.22 (s, 1H), 7.91-7.88 (m, 2H), 7.69-7.46 (m, 6H), 4.38 (s, 2H), 3.21-3.16 (m, 2H), 2.91 (s, 3H), 2.56-2.50 (m, 2H). (3H-Not revealed by ¹H NMR). MS m/z = 454.0(M + H)⁺. |
| 143 | 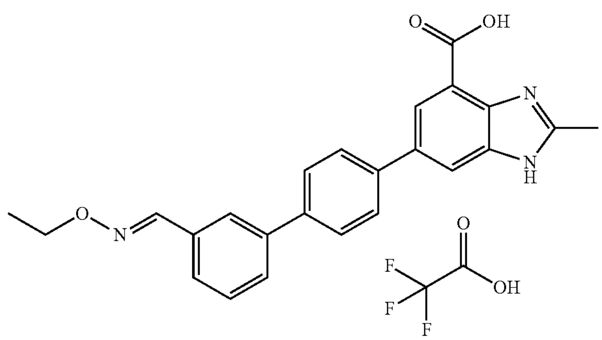 | A-1 B & E, G | ¹H NMR (300 MHz, CD$_3$OD): δ 8.38 (s, 1H), 8.19-8.15 (m, 2H), 7.93-7.50 (m, 8H), 4.24-4.22 (m, 2H), 2.85 (s, 3H), 1.35-1.30 (t, J = 6.9 Hz, 3H). (2H-Not revealed by ¹H NMR). MS m/z = 399.9(M + H)⁺. |
| 144 | 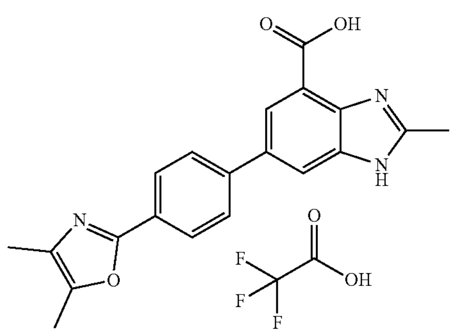 | A-2 & E, G | ¹H NMR (300 MHz, DMSO-d$_6$): δ 14.00 (bs, 1H), 8.28-8.24 (m, 2H), 8.04-7.91 (m, 4H), 2.77 (s, 3H), 2.35 (s, 3H), 2.12 (s, 3H). MS m/z = 348.0(M + H)⁺. |
| 145 | 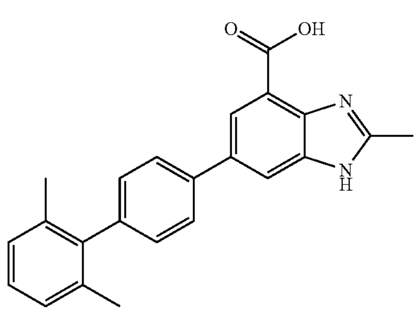 [SMILES: Cc1nc2c(C(=O)O)cc(-c3ccc(-c4c(C)cccc4C)cc3)cc2[nH]1] | A-1 & E | ¹H NMR (300 MHz, DMSO-d$_6$): δ 8.33-8.31 (d, J = 5.1 Hz, 2H), 7.90-7.87 (d, J = 7.8 Hz, 2H), 7.33-7.31 (d, J = 6.0 Hz, 2H), 7.19-7.13 (m, 3H), 2.84 (s, 3H), 2.03 (s, 6H). (2H-Not revealed by ¹H NMR). MS m/z = 357.1(M + H)⁺. |

TABLE II-continued

| Example No | Structure | General Procedure | Analytical data |
|---|---|---|---|
| 146 | 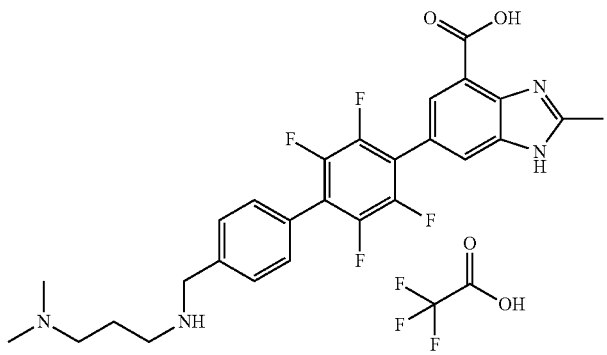 | A-2, B & E, G | $^1$H NMR (300 MHz, CD$_3$OD): δ (ppm) 8.27-8.15 (d, J = 3.6 Hz, 2H), 7.71 (s, 4H), 4.36 (s, 2H), 3.52-3.47 (m, 2H), 2.92-2.90 (m, 9H), 2.20 (m, 2H), 1.20-1.15 (t, J = 6.0 Hz, 2H). (3H-Not revealed by $^1$H NMR). MS m/z = 515.1(M + H)$^+$. |
| 147 | 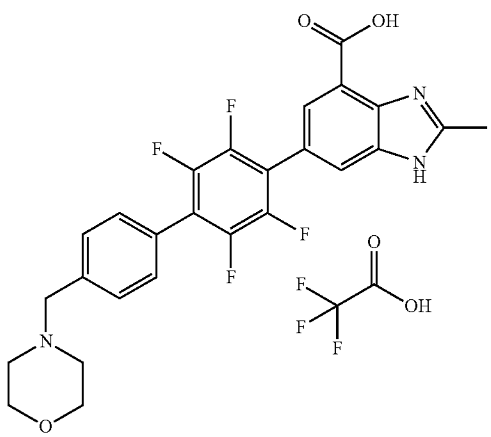 | A-2, B & E, G | $^1$H NMR (300 MHz, DMSO-d$_6$): δ 13.80 (bs, 1H), 10.20 (bs, 1H), 8.14 (s, 1H), 8.02 (s, 1H), 7.72 (s, 4H), 4.45 (s, 2H), 3.68 (m, 4H), 3.23 (m, 4H), 2.71 (s, 3H). MS m/z = 500.0(M + H)$^+$. |
| 148 | 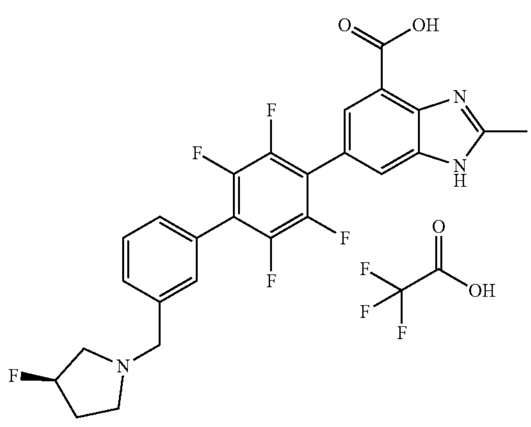 | A-2, B & E, G | $^1$H NMR (300 MHz, DMSO-d$_6$): δ 13.80 (bs, 1H), 10.80 (bs, 1H), 8.17 (s, 1H), 8.05 (s, 1H), 7.80-7.71 (m, 4H), 5.58 (m, 1H), 5.40 (m, 1H), 4.54 (m, 3H), 3.56 (m, 4H), 2.73 (s, 3H). MS m/z = 502.0(M + H)$^+$. |

TABLE II-continued

| Example No | Structure | General Procedure | Analytical data |
|---|---|---|---|
| 149 | 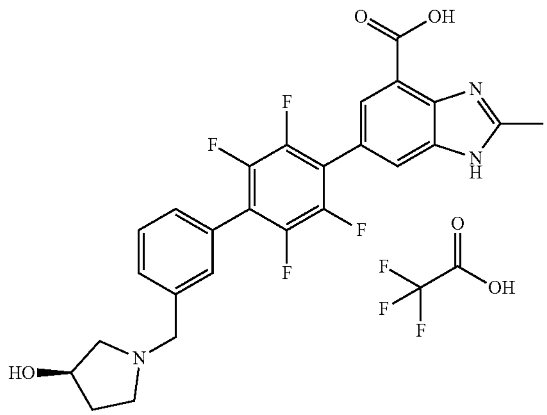 | A-2, B & E, G | $^1$H NMR (300 MHz, DMSO-d$_6$): δ 13.80 (bs, 1H), 10.50 (bs, 1H), 8.15 (s, 1H), 8.03 (s, 1H), 7.78-7.70 (m, 4H), 4.53-4.47 (m, 3H), 3.55 (m, 2H), 3.21 (m, 2H), 2.72 (s, 3H), 2.27-2.08 (m, 3H). MS m/z = 499.9(M + H)$^+$. |
| 150 | 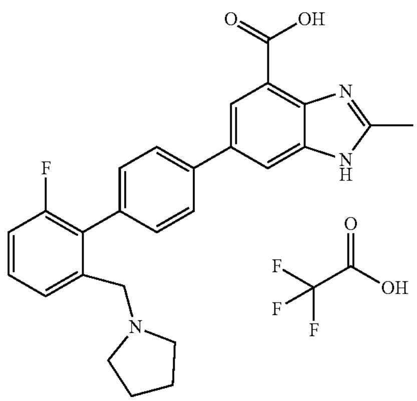 [SMILES: Cc1nc2c(C(=O)O)cc(-c3ccc(-c4c(F)cccc4CN4CCCC4)cc3)cc2[nH]1 ; O=C(O)C(F)(F)F] | A-1, B & E, G | $^1$H NMR (300 MHz, DMSO-d$_6$): δ 13.80 (bs, 1H), 9.76 (bs, 1H), 8.28-8.24 (d, J = 12.0 Hz, 2H), 7.94-7.91 (d, J = 6.6 Hz, 2H), 7.61-7.49 (m, 5H), 4.30 (s, 2H), 3.61-3.40 (m, 3H), 2.84 (m, 3H), 1.81 (m, 5H). MS m/z = 430.1(M + H)$^+$. |
| 151 | 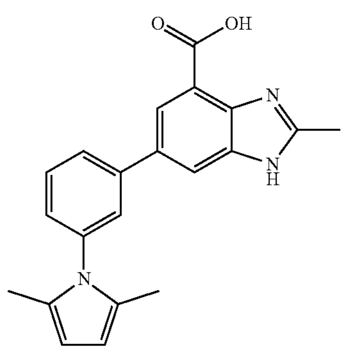 | A-2 & E | $^1$H NMR (300 MHz, DMSO-d$_6$): δ 13.80 (bs, 1H), 12.40 (bs, 1H), 8.10 (s, 1H), 8.01 (s, 1H), 7.80-7.78 (m, 2H), 7.63-7.54 (m, 2H), 5.82 (s, 2H), 2.56 (s, 3H), 2.03 (s, 6H). MS m/z = 346.1(M + H)$^+$. |
| 152 | 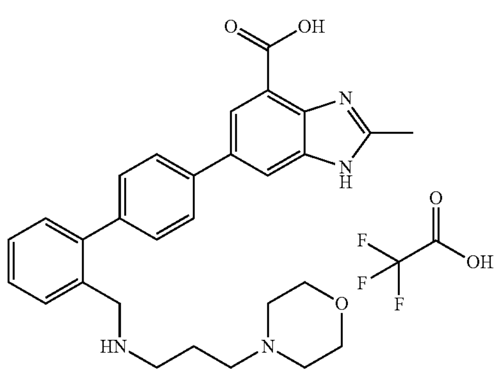 | A-1, B & E, G | $^1$H NMR (300 MHz, DMSO-d$_6$): δ 13.80 (bs, 1H), 10.40 (bs, 1H), 9.17 (bs, 1H), 8.29-8.25 (d, J = 12.0 Hz, 2H), 7.92-7.89 (d, J = 9.0 Hz, 2H), 7.75-7.72 (m, 1H), 7.55-7.53 (m, 4H), 7.44-7.41 (m, 1H), 4.20 (m, 2H), 3.64 (m, 4H), 3.11 (m, 6H), 2.95 (s, 2H), 2.78 (s, 3H), 1.96 (m, 2H). MS m/z = 485.2(M + H)$^+$. |

TABLE II-continued
| Example No | Structure | General Procedure | Analytical data |
|---|---|---|---|
| 153 | 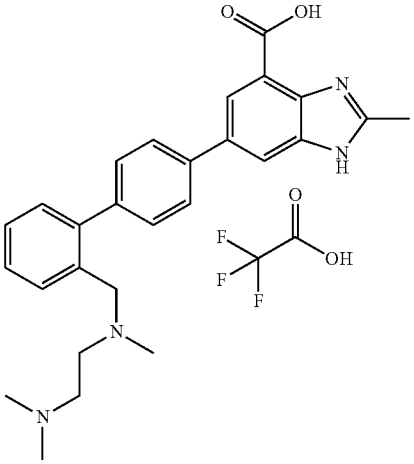 | A-1, B & E, G | ¹H NMR (300 MHz, CD₃OD): δ 8.35(s, 1H), 8.16 (s, 1H), 7.82 (d, J = 8.1 Hz, 2H), 7.65-7.63 (m, 1H), 7.50-7.33 (m, 5H), 3.75 (s, 2H), 3.15-3.11 (m, 2H), 2.82 (s, 3H), 2.65-2.67 (m, 8H), 2.22 (s, 3H). (2H-Not revealed by ¹H NMR). MS m/z = 443.0(M + H)⁺. |
| 154 | 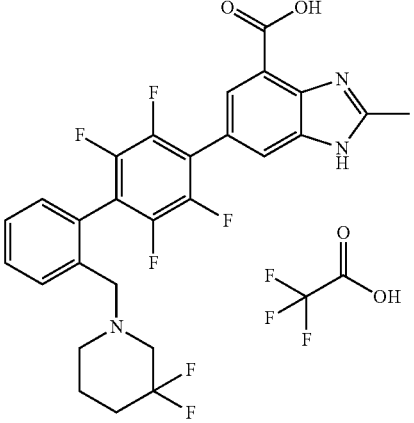 [SMILES: Cc1nc2c(C(=O)O)cc(-c3c(F)c(F)c(-c4ccccc4CN4CCCC(F)(F)C4)c(F)c3F)cc2[nH]1 ; O=C(O)C(F)(F)F] | A-2, B & E, G | ¹H NMR (300 MHz, DMSO-d₆): δ 13.80 (bs, 1H), 8.16-8.05 (m, 2H), 7.61 (m, 4H), 3.04 (m, 4H), 2.73 (s, 5H), 1.99-1.77 (m, 4H). MS m/z = 534.0(M + H)⁺. |
| 155 | 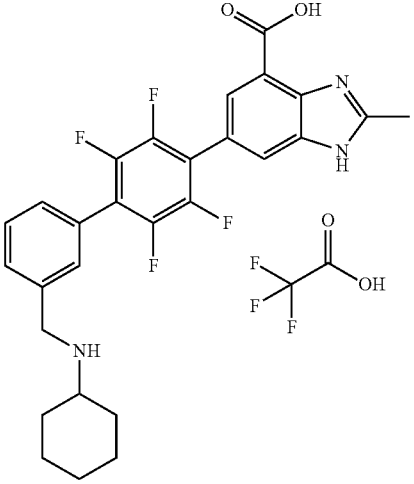 | A-2, B & E, G | ¹H NMR (300 MHz, CD₃OD): δ 8.12 (s, 1H), 8.02 (s, 1H), 7.72-7.68 (m, 4H), 4.34 (s, 2H), 2.77 (s, 3H), 2.22 (m, 2H), 1.93 (m, 2H), 1.73 (m, 1H), 1.41-1.29 (m, 6H). (3H-Not revealed by ¹H NMR). MS m/z = 512.1(M + H)⁺. |

| Example No | Structure | General Procedure | Analytical data |
|---|---|---|---|
| 156 | 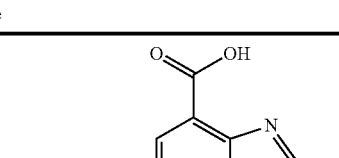 | A-1, B & E, G | $^1$H NMR (300 MHz, DMSO-$d_6$): δ 13.90 (bs, 1H), 9.20 (m, 2H), 8.27 (d, J = 8.7 Hz, 2H), 7.90 (d, J = 7.5 Hz, 2H), 7.71-7.70 (m, 1H), 7.55-7.43 (m, 5H), 4.27 (s, 2H), 3.49-3.37 (m, 4H), 3.08 (s, 3H), 2.77 (s, 3H). MS m/z = 464.1(M + H)$^+$. |

The following examples are prepared using the General Procedures A to G (A-1(method-1 & A-2(method-2), appropriate boronic acids/boronic esters were used in Suzuki reaction and appropriate basic amines were used in reductive aminations).

Measurement of DHODH Inhibitory Enzyme Activity (In Vitro Assays)

The DHODH activity assay is a coupled enzyme assay in which oxidation of DHO and subsequent reduction of ubiquinone are stoichiometrically equivalent to the reduction of DCIP (2,6-dichlorophenol). The reduction of DCIP is accompanied by a loss of absorbance at 610 nm.

Reagents used: L-Dihydroorotic acid, Sigma, D7128, 2,6-Dichloroindophenol sodium salt hydrate, sigma, D1878 Dimethyl sulfoxide (DMSO), spectroscopic grade purchased from Spectrochem, cat no. 0704209, B. no.—3183650 Decylubiquinone, Sigma, D7911.

Preparation of Solutions/Reagents:

Buffer Preparation: 50 mM tris HCl, 150 mM KCl, and pH 8.0, 0.8% triton.

L-Dihydroorotic acid stock solution of 20 mM in buffer.

2, 6-Dichloroindophenol Sodium salt hydrate stock solution of 20 mM in buffer.

Decylubiquinone stock solution of 20 mM in buffer.

DMSO used as vehicle.

Procedure:

5 μL of Dimethyl sulfoxide or a compound of formula (I) in DMSO solution was added to the wells of a 96 well plate. Compounds of formula (I) were measured at 10 μM.

Protein along with buffer was added, so that the total volume including the DMSO was 87 μL. Compound and protein were incubated for half an hour at room temperature after mixing. 5 μL of 20 mM solution of L-Dihydroorotic acid, 5 μL of 2 mM solution of Decylubiquinone and 3 μL of 2 mM solution of 2, 6-Dichloroindophenol sodium salt hydrate were added to the above solution (total assay volume 100 μL). The mixture was stirred for 2 min and absorbance was recorded at every 10 min at 610 nanometers. Percent inhibition is calculated as follows 100*{(Abs610 for reaction containing compound)−(Abs610 for positive control) (Abs610 for no enzyme reaction)−(Abs610 for positive control)

Reaction containing compound has compound, buffer, enzyme and substrates

Positive control contains DMSO, buffer, enzyme and substrates

No Enzyme reaction contains DMSO, buffer and substrates

IC50 determination: A 2 mM DMSO stock solution of the selected 1, 4, 6-trisubstituted-2-alkyl-1H-benzo[d]imidazole derivatives of formula (I) of the present invention to be examined was prepared. Subsequent ⅓rd dilutions were made as follows:

| S. No. | Stock Concentration of Compound in DMSO (mM) | Assay Concentration for Compound (μM) | Composition of compound solution used for assay |
|---|---|---|---|
| 1 | 2 | 100 | 60 μL 2 mM |
| 2 | 0.66667 | 33 | 20 μL 2 mM + 40 μL DMSO |
| 3 | 0.22222 | 11 | 20 μL 0.66667 mM + 40 μL DMSO |
| 4 | 0.07407 | 3.7 | 20 μL 0.22222 mM + 40 μL DMSO |
| 5 | 0.02469 | 1.2 | 20 μL 0.07407 mM + 40 μL DMSO |
| 6 | 0.00823 | 0.4 | 20 μL 0.02469 mM + 40 μL DMSO |
| 7 | 0.00274 | 0.13 | 20 μL 0.00823 mM + 40 μL DMSO |
| 8 | 0.00091 | 0.0457 | 20 μL 0.00274 mM + 40 μL DMSO |
| 9 | 0.00031 | 0.0152 | 20 μL 0.00091 mM + 40 μL DMSO |
| 10 | 0.0001 | 0.0051 | 20 μL 0.00031 mM + 40 μL DMSO |
| 11 | 0.00003 | 0.00017 | 20 μL 0.00010 mM + 40 μL DMSO |

5 μL of each stock of compound of formula (I) (solution indicated in column 4 of table) was used for each 100 μL assay. Therefore, 5 μL of the 2 mM stock provided 100 μL of 100 μM solution of compound of formula (I), when made up with buffer, protein and substrate. See also: Ulrich et al. (2001) Eur. J. Biochem. 268, 1861-1868.

Measurement of Cell Proliferation Activity (Jurkat Cell)

Jurkat cells are an immortalized cell line of T lymphocyte cells, which are used to study acute T cell leukaemia, T cell signalling, and the expression of various chemokine receptors susceptible to viral entry, particularly HIV. Jurkat cells are also useful in science because of their ability to produce interleukin 2. Their primary use, however, is to determine the mechanism of differential susceptibility of cancers to drugs and radiation.

PROTOCOL

Jurkat cells are cultured in RPMI medium with 10% FBS, and seeded at a density of 100,000 cells per well in a 96 well plate. Compound is added at different concentrations (typically starting at 10 μM followed by half log dilutions for a total of 8-10 concentrations). Each concentration is tested in triplicate and DMSO concentration is kept constant at 0.25-0.5%. The cells are then incubated in a $CO_2$ incubator at 37° C. for 72 hrs before determining cell viability using XTT assay. Cell viability is plotted as a function of concentration and $EC_{50}$ is determined using GraphPad Prism software

REFERENCES

Roehm, N et al [1991] An improved colorimetric assay for cell proliferation and viability utilizing the tetrazolium salt XTT. J. Immunol. Methods 142:257-265. Reagents:
Roswells park memorial institute's medium, (RPMI-1640 complete media) pH-7.4±0.2 (Sigma R6504).
Dimethyl sulfoxide (DMSO), spectroscopic grade purchased from Spectrochem, (cat no. 0704209, B. no.— 3183650 MEM Cat. No. M0268, Sigma). Fetal Bovine Serum (Cat. No. F9665, Sigma Aldrich). XTT sodium salt (Sigma Cat. No. X4251). PMS (Sigma Cat. No. 68600).
Preparation of Solutions/Reagents
RPMI media supplemented with antibiotics, 10% FBS, Sodium Pyruvate and NEA (non essential amino acids).
XTT—A freshly prepared solution of XTT is made in the growth medium, with a final concentration of 1 mg/ml.
PMS—Stock is prepared with 1×PBS at 0.383 mg/ml and stored in aliquots at −20° C. The XTT solution at 20 μl/ml was added just before use.
Test solution—Serially diluted DMSO solutions are further diluted with media to 2× the required concentration in well.
Procedure:
Culture Jurkat cells in T-25 flasks at a density of 0.2× 106/ml 2-3 days before the day of experiment set up.
Centrifuge Jurkat T-cell suspension at 1200 rpm for 10 minutes and resuspend cells again in fresh RPMI medium with 10% FBS. Count the cells and dilute suspension to a density of 2×106 cells/ml. Seed 50 μL of this suspension in each well of a 96 well plate (100,000 cells per well). Keep the edges of the plate empty to avoid evaporation.
Serially dilute DMSO stocks of compounds to get different concentrations for an EC50 curve. 50 μL of compound diluted in media (2× concentration required in well) is added to each well. DMSO concentration should be kept constant at 0.25-0.5% for all wells.
Typically, for all compounds with IC50<μM, compound concentration can start at 10 μM followed by half log dilutions for a total of 8-10 concentrations. Each concentration has to be tested in triplicate.
Include controls such as cells without compound (with same DMSO concentration as compound wells), and media control, Incubate the 96 well plate in a $CO_2$ incubator at 37° C. for 72 hrs before determining cell viability using XTT assay.
XTT assay: to each well, add 50 μL of 1 mg/ml XTT solution with 20 μl of PMS/mL. Read the plates after 2 hours at 465 nm using the spectrophotometer. XTT reading for media without cells is used as background reading.

Calculate % cell viability assuming that the cells without compound are 100% viable.

Plot % cell viability as a function of concentration and determine EC50 by using software such as GraphPad Prism to fit the curve.

The compounds were screened at 1 μM/10 μM concentration and the results are summarized in the table below along with the $IC_{50}$ (uM) and $EC_{50}$ (uM) details for selected examples. $IC_{50}$ (uM) and $EC_{50}$ (uM) values of the compounds are set forth in below Table wherein "A" refers to an $IC_{50}$ (uM) value in range of 0.001 to 0.0099 uM, "B" refers to $IC_{50}$ (uM) value in range of 0.01 to 0.099 uM and "C" refers to $IC_{50}$ (uM) value of greater than 0.1 uM.

| Ex. No. | $IC_{50}$ DHODH (μM) | $EC_{50}$ Proliferation Jurkat cells (μM) |
|---|---|---|
| 1 | B | 0.133 |
| 4 | C | — |
| 5 | B | 0.049 |
| 10 | B | 0.032 |
| 15 | B | — |
| 16 | B | — |
| 17 | B | — |
| 18 | B | 0.111 |
| 20 | B | — |
| 21 | B | — |
| 23 | B | — |
| 25 | A | — |
| 36 | B | — |
| 39 | B | — |
| 42 | B | — |
| 45 | B | — |
| 46 | A | — |
| 52 | A | — |
| 53 | A | — |
| 56 | A | — |
| 57 | A | — |
| 59 | B | — |
| 60 | A | — |
| 61 | A | — |
| 62 | B | — |
| 64 | A | — |
| 65 | A | — |
| 67 | A | — |
| 69 | A | — |
| 84 | B | — |
| 90 | B | — |
| 111 | A | — |
| 117 | A | — |
| 145 | B | — |
| 150 | A | — |

The invention claimed is:
1. A compound of formula (I):

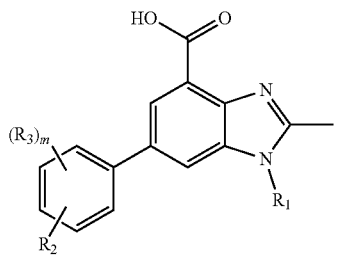

or a pharmaceutically acceptable salt, solvate, tautomer, hydrate, stereoisomer and mixture of isomers, or N-oxide thereof;
wherein;
$R_1$ is hydrogen or linear or branched $C_1$-$C_6$ alkyl;
$R_2$ is an optionally substituted Cb, an optionally substituted Het or —O—$(CH_2)_p$Cb'; wherein the optional substituent, at each occurrence, is independently selected from one or more occurrences of $R_4$;
$R_3$ is hydrogen, halogen, linear or branched $C_1$-$C_6$ alkyl or —$OR_5$;
$R_4$ is independently selected from hydrogen, halogen, linear or branched $C_1$-$C_6$ alkyl, —$(CH_2)_pO(CH_2)_qR_7$, —$(CH_2)_pS(=O)_xR_5$, —$C(R_5)=NOR_5$, —$(CH_2)_p$Het' and —$(CH_2)_pNR_5(CH_2)_qR_6$;
$R_5$ is independently selected from hydrogen and linear or branched $C_1$-$C_6$ alkyl;
$R_6$ is independently selected from hydrogen, linear or branched $C_1$-$C_6$ alkyl, —(CO)Het, Cb', Het', —$CF_3$, —C≡$CR_5$, —$N(R_5)_2$, —$S(=O)_xR_5$ and $OR_5$;
$R_7$ is independently selected from hydrogen, linear or branched $C_1$-$C_6$ alkyl, Cb', Het', —$CF_3$, —C≡$CR_5$, —$N(R_5)_2$ or —$S(=O)_xR_5$;
Cb and Cb' independently represents a monocyclic, a fused or non-fused bicyclic, saturated, unsaturated or aromatic carbocyclic ring system having 3 to 14 carbon atoms; wherein the Cb and Cb' are optionally substituted with 'n' occurrences of $R_7$;
Het and Het' independently represents a 3- to 14-membered, monocyclic, a fused or non-fused bicyclic, saturated, unsaturated or aromatic heterocyclic ring system having at least 1 to 4 heteroatom or heterogroup selected from N, O, S, CO, NH, SO and $SO_2$; wherein the Het and Het' are optionally substituted with 'n' occurrences of $R_8$;
$R_8$, at each occurrence, is independently selected from halogen, hydroxy, oxo and linear or branched C1-C6 alkyl;
'm' is 0 to 4; 'n', 'p' and 'q' independently represents 0 to 3; and 'x' is 0 to 2.

2. The compound according to claim 1, wherein the compound is represented by formula (IA);

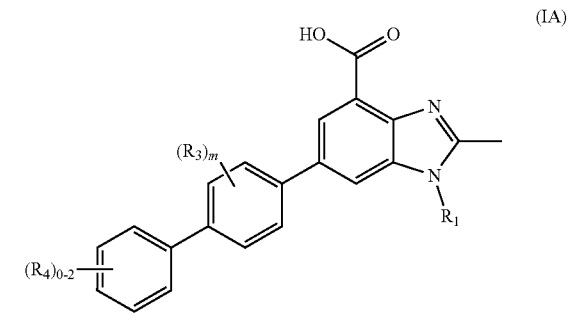

or a pharmaceutically acceptable salt or a stereoisomer thereof.

3. The compound according to claim 1, wherein the compound is represented by formula (IB);

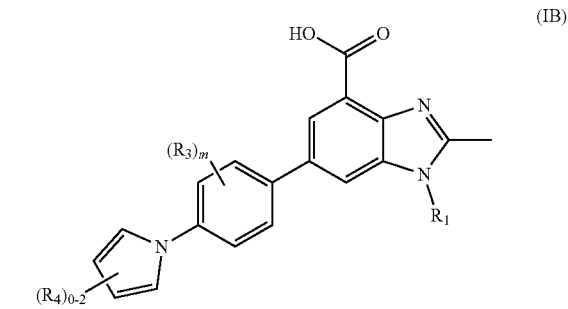

or a pharmaceutically acceptable salt or a stereoisomer thereof.

4. The compound according to claim 2, wherein $R_1$ is hydrogen.

5. The compound according to claim 1, with all tautomeric forms of formula (Ia) and (Ia') when $R_1$ is hydrogen;

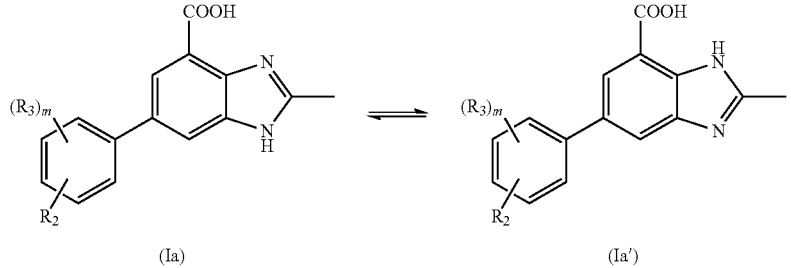

or a pharmaceutically acceptable salt or a stereoisomer thereof.

6. The compound according to claim 1, wherein $R_2$ is an optionally substituted phenyl; wherein the optional substituent, at each occurrence, is independently selected from one or more occurrences of $R_4$.

7. The compound according to claim 2, wherein $R_4$ is independently selected from hydrogen, halogen, linear or branched $C_1$-$C_6$ alkyl, —$(CH_2)_p$Het', —$(CH_2)_p$NR$_5$ $(CH_2)_q$R$_6$ and —$(CH_2)_p$O$(CH_2)_q$R$_7$; wherein $R_5$ is hydrogen; and $R_6$ and $R_7$ independently represents Cb' and Het'.

8. The compound according to claim 7, wherein Cb' represents phenyl or cyclopropyl; and Het' denotes piperidine, morpholine, 3-fluoro pyrrolidine, or thiomorpholine 1,1-dioxide.

9. The compound according to claim 1, wherein $R_3$ is hydrogen or halogen.

10. A compound, or a pharmaceutically acceptable salt or a stereoisomer thereof, selected from one or more of the following:

| Example No | IUPAC names |
|---|---|
| 1. | 6-([1,1'-biphenyl]-4-yl)-2-methyl-1H-benzo[d]imidazole-4-carboxylic acid; |
| 2. | 6-(3',5'-difluoro-[1,1'-biphenyl]-4-yl)-2-methyl-1H-benzo[d]imidazole-4-carboxylic acid; |
| 3. | 6-(3',4'-difluoro-[1,1'-biphenyl]-4-yl)-2-methyl-1H-benzo[d]imidazole-4-carboxylic acid; |
| 4. | 6-(2',3'-difluoro-[1,1'-biphenyl]-4-yl)-2-methyl-1H-benzo[d]imidazole-4-carboxylic acid; |
| 5. | 6-(2'-fluoro-[1,1'-biphenyl]-4-yl)-2-methyl-1H-benzo[d]imidazole-4-carboxylic acid; |
| 6. | 6-(4'-fluoro-[1,1'-biphenyl]-4-yl)-2-methyl-1H-benzo[d]imidazole-4-carboxylic acid; |
| 7. | 2-methyl-6-(4-(pyridin-3-yl)phenyl)-1H-benzo[d]imidazole-4-carboxylic acid; |
| 8. | 6-(3'-fluoro-[1,1'-biphenyl]-4-yl)-2-methyl-1H-benzo[d]imidazole-4-carboxylic acid.; |
| 9. | 2-methyl-6-(4-(pyridin-4-yl)phenyl)-1H-benzo[d]imidazole-4-carboxylic acid; |
| 10. | 6-(3'-methoxy-[1,1'-biphenyl]-4-yl)-2-methyl-1H-benzo[d]imidazole-4-carboxylic acid; |
| 11. | 2-methyl-6-(3'-(trifluoromethoxy)-[1,1'-biphenyl]-4-yl)-1H-benzo[d]imidazole-4-carboxylic acid; |
| 12. | 6-(2',5'-difluoro-[1,1'-biphenyl]-4-yl)-2-methyl-1H-benzo[d]imidazole-4-carboxylic acid; |
| 13. | 2-methyl-6-(4'-(trifluoromethoxy)-[1,1'-biphenyl]-4-yl)-1H-benzo[d]imidazole-4-carboxylic acid; |
| 14. | 6-(4'-methoxy-[1,1'-biphenyl]-4-yl)-2-methyl-1H-benzo[d]imidazole-4-carboxylic acid; |
| 15. | 6-(3'-(benzyloxy)-[1,1'-biphenyl]-4-yl)-2-methyl-1H-benzo[d]imidazole-4-carboxylic acid; |
| 16. | 6-(3'-hydroxy-[1,1'-biphenyl]-4-yl)-2-methyl-1H-benzo[d]imidazole-4-carboxylic acid; |
| 17. | 6-(2'-(benzyloxy)-[1,1'-biphenyl]-4-yl)-2-methyl-1H-benzo[d]imidazole-4-carboxylic acid; |
| 18. | 6-(2'-methoxy-[1,1'-biphenyl]-4-yl)-2-methyl-1H-benzo[d]imidazole-4-carboxylic acid; |
| 19. | 6-(4'-(benzyloxy)-[1,1'-biphenyl]-4-yl)-2-methyl-1H-benzo[d]imidazole-4-carboxylic acid; |
| 20. | 6-(4'-hydroxy-[1,1'-biphenyl]-4-yl)-2-methyl-1H-benzo[d]imidazole-4-carboxylic acid; |
| 21. | 6-(2'-fluoro-3'-methoxy-[1,1'-biphenyl]-4-yl)-2-methyl-1H-benzo[d]imidazole-4-carboxylic acid; |
| 22. | 6-(3'-(benzyloxy)-5'-fluoro-[1,1'-biphenyl]-4-yl)-2-methyl-1H-benzo[d]imidazole-4-carboxylic acid; |
| 23. | 6-(2'-hydroxy-[1,1'-biphenyl]-4-yl)-2-methyl-1H-benzo[d]imidazole-4-carboxylic acid; |
| 24. | 2-methyl-6-(3'-methyl-[1,1'-biphenyl]-4-yl)-1H-benzo[d]imidazole-4-carboxylic acid; |
| 25. | 2-methyl-6-(2'-methyl-[1,1'-biphenyl]-4-yl)-1H-benzo[d]imidazole-4-carboxylic acid; |
| 26. | 2-methyl-6-(4'-(piperidin-1-ylmethyl)-[1,1'-biphenyl]-4-yl)-1H-benzo[d]imidazole-4-carboxylic acid.2,2,2-trifluoroacetic acid; |
| 27. | 6-(4'-((isopropylamino)methyl)-[1,1'-biphenyl]-4-yl)-2-methyl-1H-benzo[d]imidazole-4-carboxylic acid.2,2,2-trifluoroacetic acid; |
| 28. | 2-methyl-6-(4'-(pyrrolidin-1-ylmethyl)-[1,1'-biphenyl]-4-yl)-1H-benzo[d]imidazole-4-carboxylic acid.2,2,2-trifluoroacetic acid; |
| 29. | 2-methyl-6-(4'-(thiomorpholinomethyl)-[1,1'-biphenyl]-4-yl)-1H-benzo[d]imidazole-4-carboxylic acid.2,2,2-trifluoroacetic acid; |
| 30. | 6-(4'-((3,3-difluoropiperidin-1-yl)methyl)-[1,1'-biphenyl]-4-yl)-2-methyl-1H-benzo[d]imidazole-4-carboxylic acid.2,2,2-trifluoroacetic acid; |
| 31. | 2-methyl-6-(3'-(piperidin-1-ylmethyl)-[1,1'-biphenyl]-4-yl)-1H-benzo[d]imidazole-4-carboxylic acid.2,2,2-trifluoroacetic acid; |
| 32. | 2-methyl-6-(3'-(pyrrolidin-1-ylmethyl)-[1,1'-biphenyl]-4-yl)-1H-benzo[d]imidazole-4-carboxylic acid.2,2,2-trifluoroacetic acid; |
| 33. | 2-methyl-6-(3'-(thiomorpholinomethyl)-[1,1'-biphenyl]-4-yl)-1H-benzo[d]imidazole-4-carboxylic acid; |
| 34. | 6-(3'-((isopropylamino)methyl)-[1,1'-biphenyl]-4-yl)-2-methyl-1H-benzo[d]imidazole-4-carboxylic acid.2,2,2-trifluoroacetic acid; |
| 35. | 2-methyl-6-(3'-(morpholinomethyl)-[1,1'-biphenyl]-4-yl)-1H-benzo[d]imidazole-4-carboxylic acid.2,2,2-trifluoroacetic acid; |
| 36. | 6-(3'-((1,1-dioxidothiomorpholino)methyl)-[1,1'-biphenyl]-4-yl)-2-methyl-1H-benzo[d]imidazole-4-carboxylic acid.2,2,2-trifluoroacetic acid; |
| 37. | 6-(3'-((3,3-difluoropiperidin-1-yl)methyl)-[1,1'-biphenyl]-4-yl)-2-methyl-1H-benzo[d]imidazole-4-carboxylic acid.2,2,2-trifluoroacetic acid; |
| 38. | 6-(3'-((dipropylamino)methyl)-[1,1'-biphenyl]-4-yl)-2-methyl-1H-benzo[d]imidazole-4-carboxylic acid.2,2,2-trifluoroacetic acid; |
| 39. | 6-(3'-((tert-butylamino)methyl)-[1,1'-biphenyl]-4-yl)-2-methyl-1H-benzo[d]imidazole-4-carboxylic acid.2,2,2-trifluoroacetic acid; |
| 40. | 6-(3'-((cycloheptylamino)methyl)-[1,1'-biphenyl]-4-yl)-2-methyl-1H-benzo[d]imidazole-4-carboxylic acid.2,2,2-trifluoroacetic acid; |
| 41. | 6-(3'-((3-hydroxyazetidin-1-yl)methyl)-[1,1'-biphenyl]-4-yl)-2-methyl-1H-benzo[d]imidazole-4-carboxylic acid.2,2,2-trifluoroacetic acid; |
| 42. | 2-methyl-6-(2'-(piperidin-1-ylmethyl)-[1,1'-biphenyl]-4-yl)-1H-benzo[d]imidazole-4-carboxylic acid.2,2,2-trifluoroacetic acid; |

| Example No | IUPAC names |
|---|---|
| 43. | 6-(2'-((isopropylamino)methyl)-[1,1'-biphenyl]-4-yl)-2-methyl-1H-benzo[d]imidazole-4-carboxylic acid.2,2,2-trifluoroacetic acid; |
| 44. | 2-methyl-6-(2'-(thiomorpholinomethyl)-[1,1'-biphenyl]-4-yl)-1H-benzo[d]imidazole-4-carboxylic acid.2,2,2-trifluoroacetic acid; |
| 45. | 2-methyl-6-(2'-(morpholinomethyl)-[1,1'-biphenyl]-4-yl)-1H-benzo[d]imidazole-4-carboxylic acid.2,2,2-trifluoroacetic acid; |
| 46. | 2-methyl-6-(2'-(pyrrolidin-1-ylmethyl)-[1,1'-biphenyl]-4-yl)-1H-benzo[d]imidazole-4-carboxylic acid.2,2,2-trifluoroacetic acid; |
| 47. | 6-(2'-((1,1-dioxidothiomorpholino)methyl)-[1,1'-biphenyl]-4-yl)-2-methyl-1H-benzo[d]imidazole-4-carboxylic acid.2,2,2-trifluoroacetic acid; |
| 48. | 6-(2'-((cyclopropylamino)methyl)-[1,1'-biphenyl]-4-yl)-2-methyl-1H-benzo[d]imidazole-4-carboxylic acid.2,2,2-trifluoroacetic acid; |
| 49. | 6-(2'-((dimethylamino)methyl)-[1,1'-biphenyl]-4-yl)-2-methyl-1H-benzo[d]imidazole-4-carboxylic acid.2,2,2-trifluoroacetic acid; |
| 50. | 6-(2'-((3,3-difluoropiperidin-1-yl)methyl)-[1,1'-biphenyl]-4-yl)-2-methyl-1H-benzo[d]imidazole-4-carboxylic acid.2,2,2-trifluoroacetic acid; |
| 51. | 6-(2'-((cycloheptylamino)methyl)-[1,1'-biphenyl]-4-yl)-2-methyl-1H-benzo[d]imidazole-4-carboxylic acid.2,2,2-trifluoroacetic acid; |
| 52. | 2-methyl-6-(2,3,5,6-tetrafluoro-[1,1'-biphenyl]-4-yl)-1H-benzo[d]imidazole-4-carboxylic acid; |
| 53. | 2-methyl-6-(2,3,5,6-tetrafluoro-2'-(piperidin-1-ylmethyl)-[1,1'-biphenyl]-4-yl)-1H-benzo[d]imidazole-4-carboxylic acid.2,2,2-trifluoroacetic acid; |
| 54. | 2-methyl-6-(2,3,5,6-tetrafluoro-2'-(thiomorpholinomethyl)-[1,1'-biphenyl]-4-yl)-1H-benzo[d]imidazole-4-carboxylic acid.2,2,2-trifluoroacetic acid; |
| 55. | 2-methyl-6-(2,3,5,6-tetrafluoro-2'-((isopropylamino)methyl)-[1,1'-biphenyl]-4-yl)-1H-benzo[d]imidazole-4-carboxylic acid.2,2,2-trifluoroacetic acid; |
| 56. | 2-methyl-6-(2,3,5,6-tetrafluoro-3'-(piperidin-1-ylmethyl)-[1,1'-biphenyl]-4-yl)-1H-benzo[d]imidazole-4-carboxylic acid.2,2,2-trifluoroacetic acid; |
| 57. | 2-methyl-6-(2,3,5,6-tetrafluoro-3'-(hydroxymethyl)-[1,1'-biphenyl]-4-yl)-1H-benzo[d]imidazole-4-carboxylic acid.2,2,2-trifluoroacetic acid; |
| 58. | 2-methyl-6-(2,3,5,6-tetrafluoro-3'-(pyrrolidin-1-ylmethyl)-[1,1'-biphenyl]-4-yl)-1H-benzo[d]imidazole-4-carboxylic acid; |
| 59. | 2-methyl-6-(2,3,5,6-tetrafluoro-3'-((isopropylamino)methyl)-[1,1'-biphenyl]-4-yl)-1H-benzo[d]imidazole-4-carboxylic acid.2,2,2-trifluoroacetic acid; |
| 60. | 6-(3'-((cyclopropylamino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 61. | 2-methyl-6-(2,3,5,6-tetrafluoro-4'-(piperidin-1-ylmethyl)-[1,1'-biphenyl]-4-yl)-1H-benzo[d]imidazole-4-carboxylic acid.2,2,2-trifluoroacetic acid; |
| 62. | 2-methyl-6-(2,3,5,6-tetrafluoro-4'-(pyrrolidin-1-ylmethyl)-[1,1'-biphenyl]-4-yl)-1H-benzo[d]imidazole-4-carboxylic acid.2,2,2-trifluoroacetic acid; |
| 63. | 2-methyl-6-(2,3,5,6-tetrafluoro-4'-(thiomorpholinomethyl)-[1,1'-biphenyl]-4-yl)-1H-benzo[d]imidazole-4-carboxylic acid.2,2,2-trifluoroacetic acid; |
| 64. | 6-(4'-((3,3-difluoropiperidin-1-yl)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 65. | 6-(4'-((1,1-dioxidothiomorpholino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 66. | 2-methyl-6-(2,3,5,6-tetrafluoro-4'-((isopropylamino)methyl)-[1,1'-biphenyl]-4-yl)-1H-benzo[d]imidazole-4-carboxylic acid.2,2,2-trifluoroacetic acid; |
| 67. | 6-(4-(2,5-dimethyl-1H-pyrrol-1-yl)-2,3,5,6-tetrafluorophenyl)-2-methyl-1H-benzo[d]imidazole-4-carboxylic acid; |
| 68. | 6-([1,1'-biphenyl]-4-yl)-1,2-dimethyl-1H-benzo[d]imidazole-4-carboxylic acid; |
| 69. | 6-(4-(benzyloxy)phenyl)-2-methyl-1H-benzo[d]imidazole-4-carboxylic acid; |
| 70. | 2-methyl-6-(4'-(piperidin-4-ylmethoxy)-[1,1'-biphenyl]-4-yl)-1H-benzo[d]imidazole-4-carboxylic acid.2,2,2-trifluoroacetic acid; |
| 71. | 2-methyl-6-(4'-(2-(piperidin-4-yl)ethoxy)-[1,1'-biphenyl]-4-yl)-1H-benzo[d]imidazole-4-carboxylic acid.2,2,2-trifluoroacetic acid; |
| 72. | 2-methyl-6-(3'-(piperidin-4-ylmethoxy)-[1,1'-biphenyl]-4-yl)-1H-benzo[d]imidazole-4-carboxylic acid.2,2,2-trifluoroacetic acid; |
| 73. | 2-methyl-6-(3'-(piperidin-4-yloxy)-[1,1'-biphenyl]-4-yl)-1H-benzo[d]imidazole-4-carboxylic acid.2,2,2-trifluoroacetic acid; |
| 74. | 2-methyl-6-(4'-(2-morpholinoethoxy)-[1,1'-biphenyl]-4-yl)-1H-benzo[d]imidazole-4-carboxylic acid.2,2,2-trifluoroacetic acid; |
| 75. | 2-methyl-6-(3'-(2-(piperidin-4-yl)ethoxy)-[1,1'-biphenyl]-4-yl)-1H-benzo[d]imidazole-4-carboxylic acid.2,2,2-trifluoroacetic acid; |
| 76. | 2-methyl-6-(3'-(2-(tetrahydro-2H-pyran-4-yl)ethoxy)-[1,1'-biphenyl]-4-yl)-1H-benzo[d]imidazole-4-carboxylic acid.2,2,2-trifluoroacetic acid; |
| 77. | (S)-2-methyl-6-(3'-(pyrrolidine-2-carboxamido)-[1,1'-biphenyl]-4-yl)-1H-benzo[d]imidazole-4-carboxylic acid.2,2,2-trifluoroacetic acid; |
| 78. | 2-methyl-6-(3'-(piperidine-4-carboxamido)-[1,1'-biphenyl]-4-yl)-1H-benzo[d]imidazole-4-carboxylic acid.2,2,2-trifluoroacetic acid; |
| 79. | 2-methyl-6-(2'-(methylsulfonyl)-[1,1'-biphenyl]-4-yl)-1H-benzo[d]imidazole-4-carboxylic acid.2,2,2-trifluoroacetic acid; |
| 80. | 2-methyl-6-(3'-(methylsulfonyl)-[1,1'-biphenyl]-4-yl)-1H-benzo[d]imidazole-4-carboxylic acid; |
| 81. | 2-methyl-6-(4'-(methylsulfonyl)-[1,1'-biphenyl]-4-yl)-1H-benzo[d]imidazole-4-carboxylic acid.2,2,2-trifluoroacetic acid; |
| 82. | 6-(2'-((benzylamino)methyl)-[1,1'-biphenyl]-4-yl)-2-methyl-1H-benzo[d]imidazole-4-carboxylic acid.2,2,2-trifluoroacetic acid; |
| 83. | 6-(4'-(methoxymethyl)-[1,1'-biphenyl]-4-yl)-2-methyl-1H-benzo[d]imidazole-4-carboxylic acid; |
| 84. | 2-methyl-6-(2,3,5,6-tetrafluoro-3'-(morpholinomethyl)-[1,1'-biphenyl]-4-yl)-1H-benzo[d]imidazole-4-carboxylic acid.2,2,2-trifluoroacetic acid; |
| 85. | 2-methyl-6-(4'-((methylsulfonyl)methyl)-[1,1'-biphenyl]-4-yl)-1H-benzo[d]imidazole-4-carboxylic acid; |
| 86. | 2-methyl-6-(4'-((methylthio)methyl)-[1,1'-biphenyl]-4-yl)-1H-benzo[d]imidazole-4-carboxylic acid; |
| 87. | 6-(3'-((benzylamino)methyl)-[1,1'-biphenyl]-4-yl)-2-methyl-1H-benzo[d]imidazole-4-carboxylic acid; |

| Example No | IUPAC names |
|---|---|
| 88. | 6-(2'-(hydroxymethyl)-[1,1'-biphenyl]-4-yl)-2-methyl-1H-benzo[d]imidazole-4-carboxylic acid; |
| 89. | 2-methyl-6-(4'-methyl-[1,1'-biphenyl]-4-yl)-1H-benzo[d]imidazole-4-carboxylic acid; |
| 90. | 6-(3'-(hydroxymethyl)-[1,1'-biphenyl]-4-yl)-2-methyl-1H-benzo[d]imidazole-4-carboxylic acid; |
| 91. | 6-(4'-((benzylamino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 92. | 2-methyl-6-(2,3,5,6-tetrafluoro-4'-(methylthio)-[1,1'-biphenyl]-4-yl)-1H-benzo[d]imidazole-4-carboxylic acid; |
| 93. | 2-methyl-6-(2,3,5,6-tetrafluoro-4'-(methylsulfonyl)-[1,1'-biphenyl]-4-yl)-1H-benzo[d]imidazole-4-carboxylic acid; |
| 94. | 6-(2'-((4-hydroxypiperidin-1-yl)methyl)-[1,1'-biphenyl]-4-yl)-2-methyl-1H-benzo[d]imidazole-4-carboxylic acid.2,2,2-trifluoroacetic acid; |
| 95. | (R)-6-(3'-((3-hydroxypyrrolidin-1-yl)methyl)-[1,1'-biphenyl]-4-yl)-2-methyl-1H-benzo[d]imidazole-4-carboxylic acid.2,2,2-trifluoroacetic acid; |
| 96. | 2-methyl-6-(4'-(piperidin-1-yl)-[1,1'-biphenyl]-4-yl)-1H-benzo[d]imidazole-4-carboxylic acid.2,2,2-trifluoroacetic acid; |
| 97. | 2-methyl-6-(3'-((4-methylpiperidin-1-yl)methyl)-[1,1'-biphenyl]-4-yl)-1H-benzo[d]imidazole-4-carboxylic acid.2,2,2-trifluoroacetic acid; |
| 98. | 6-(3'-(cyclopentylamino)methyl)-[1,1'-biphenyl]-4-yl)-2-methyl-1H-benzo[d]imidazole-4-carboxylic acid.2,2,2-trifluoroacetic acid; |
| 99. | 6-(3'-(((cyclopropylmethyl)amino)methyl)-[1,1'-biphenyl]-4-yl)-2-methyl-1H-benzo[d]imidazole-4-carboxylic acid.2,2,2-trifluoroacetic acid; |
| 100. | 6-(3'-((4-hydroxypiperidin-1-yl)methyl)-[1,1'-biphenyl]-4-yl)-2-methyl-1H-benzo[d]imidazole-4-carboxylic acid.2,2,2-trifluoroacetic acid; |
| 101. | 6-(4'-(hydroxymethyl)-[1,1'-biphenyl]-4-yl)-2-methyl-1H-benzo[d]imidazole-4-carboxylic acid; |
| 102. | 6-(2'-((3-hydroxyazetidin-1-yl)methyl)-[1,1'-biphenyl]-4-yl)-2-methyl-1H-benzo[d]imidazole-4-carboxylic acid; |
| 103. | 6-(2'-((dipropylamino)methyl)-[1,1'-biphenyl]-4-yl)-2-methyl-1H-benzo[d]imidazole-4-carboxylic acid; |
| 104. | 6-(2'-(((2-methoxyethyl)amino)methyl)-[1,1'-biphenyl]-4-yl)-2-methyl-1H-benzo[d]imidazole-4-carboxylic acid; |
| 105. | 2-methyl-6-(2'-((2-oxoazepan-1-yl)methyl)-[1,1'-biphenyl]-4-yl)-1H-benzo[d]imidazole-4-carboxylic acid; |
| 106. | 6-(2'-((tert-butylamino)methyl)-[1,1'-biphenyl]-4-yl)-2-methyl-1H-benzo[d]imidazole-4-carboxylic acid.2,2,2-trifluoroacetic acid; |
| 107. | (R)-6-(2'-((3-hydroxypyrrolidin-1-yl)methyl)-[1,1'-biphenyl]-4-yl)-2-methyl-1H-benzo[d]imidazole-4-carboxylic acid.2,2,2-trifluoroacetic acid; |
| 108. | 2-methyl-6-(2'-((4-methylpiperidin-1-yl)methyl)-[1,1'-biphenyl]-4-yl)-1H-benzo[d]imidazole-4-carboxylic acid.2,2,2-trifluoroacetic acid; |
| 109. | 2-methyl-6-(2'-((2-oxopyrrolidin-1-yl)methyl)-[1,1'-biphenyl]-4-yl)-1H-benzo[d]imidazole-4-carboxylic acid.2,2,2-trifluoroacetic acid; |
| 110. | 6-(2'-(((cyclopropylmethyl)amino)methyl)-[1,1'-biphenyl]-4-yl)-2-methyl-1H-benzo[d]imidazole-4-carboxylic acid.2,2,2-trifluoroacetic acid; |
| 111. | 6-(4-(2,5-dimethyl-1H-pyrrol-1-yl)phenyl)-2-methyl-1H-benzo[d]imidazole-4-carboxylic acid; |
| 112. | 6-(3'-(((2-methoxyethyl)amino)methyl)-[1,1'-biphenyl]-4-yl)-2-methyl-1H-benzo[d]imidazole-4-carboxylic acid.2,2,2-trifluoroacetic acid; |
| 113. | 2-methyl-6-(3'-((prop-2-yn-1-ylamino)methyl)-[1,1'-biphenyl]-4-yl)-1H-benzo[d]imidazole-4-carboxylic acid.2,2,2-trifluoroacetic acid; |
| 114. | 2-methyl-6-(3'-(((2-(methylsulfonyl)ethyl)amino)methyl)-[1,1'-biphenyl]-4-yl)-1H-benzo[d]imidazole-4-carboxylic acid.2,2,2-trifluoroacetic acid; |
| 115. | (R)-6-(3'-((3-fluoropyrrolidin-1-yl)methyl)-[1,1'-biphenyl]-4-yl)-2-methyl-1H-benzo[d]imidazole-4-carboxylic acid.2,2,2-trifluoroacetic acid; |
| 116. | 2-methyl-6-(2'-(((l-methylpiperidin-4-yl)amino)methyl)-[1,1'-biphenyl]-4-yl)-1H-benzo[d]imidazole-4-carboxylic acid.2,2,2-trifluoroacetic acid; |
| 117. | (R)-6-(2'-((3-fluoropyrrolidin-1-yl)methyl)-[1,1'-biphenyl]-4-yl)-2-methyl-1H-benzo[d]imidazole-4-carboxylic acid.2,2,2-trifluoroacetic acid; |
| 118. | 6-(2'-((cyclohexylamino)methyl)-[1,1'-biphenyl]-4-yl)-2-methyl-1H-benzo[d]imidazole-4-carboxylic acid.2,2,2-trifluoroacetic acid; |
| 119. | 6-(2'-((cyclohexyl(methyl)amino)methyl)-[1,1'-biphenyl]-4-yl)-2-methyl-1H-benzo[d]imidazole-4-carboxylic acid; |
| 120. | (R)-2-methyl-6-(2,3,5,6-tetrafluoro-4'-((2-hydroxypyrrolidin-1-yl)methyl)-[1,1'-biphenyl]-4-yl)-1H-benzo[d]imidazole-4-carboxylic acid; |
| 121. | 2-methyl-6-(2,3,5,6-tetrafluoro-4'-((4-methylpiperidin-1-yl)methyl)-[1,1'-biphenyl]-4-yl)-1H-benzo[d]imidazole-4-carboxylic acid.2,2,2-trifluoroacetic acid; |
| 122. | 6-(4'-(((cyclopropylmethyl)amino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 123. | (R)-2-methyl-6-(2,3,5,6-tetrafluoro-4'-((2-fluoropyrrolidin-1-yl)methyl)-[1,1'-biphenyl]-4-yl)-1H-benzo[d]imidazole-4-carboxylic acid.2,2,2-trifluoroacetic acid; |
| 124. | 6-(3'-(((cyclohexylmethyl)amino)methyl)-[1,1'-biphenyl]-4-yl)-2-methyl-1H-benzo[d]imidazole-4-carboxylic acid.2,2,2-trifluoroacetic acid; |
| 125. | 6-(3'-(((3-(dimethylamino)propyl)amino)methyl)-[1,1'-biphenyl]-4-yl)-2-methyl-1H-benzo[d]imidazole-4-carboxylic acid.2,2,2-trifluoroacetic acid; |
| 126. | 6-(3'-((diisobutylamino)methyl)-[1,1'-biphenyl]-4-yl)-2-methyl-1H-benzo[d]imidazole-4-carboxylic acid.2,2,2-trifluoroacetic acid; |
| 127. | 2-methyl-6-(2,3,5,6-tetrafluoro-4'-((prop-2-yn-1-ylamino)methyl)-[1,1'-biphenyl]-4-yl)-1H-benzo[d]imidazole-4-carboxylic acid.2,2,2-trifluoroacetic acid; |
| 128. | 6-(4'-((cyclohexylamino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 129. | 6-(2'-(((cyclohexylmethyl)amino)methyl)-[1,1'-biphenyl]-4-yl)-2-methyl-1H-benzo[d]imidazole-4-carboxylic acid.2,2,2-trifluoroacetic acid; |

| Example No | IUPAC names |
|---|---|
| 130. | 6-(2'-(((4-hydroxycyclohexyl)amino)methyl)-[1,1'-biphenyl]-4-yl)-2-methyl-1H-benzo[d]imidazole-4-carboxylic acid.2,2,2-trifluoroacetic acid; |
| 131. | 2-methyl-6-(2'-((prop-2-yn-1-ylamino)methyl)-[1,1'-biphenyl]-4-yl)-1H-benzo[d]imidazole-4-carboxylic acid.2,2,2-trifluoroacetic acid; |
| 132. | (E)-6-(3'-((methoxyimino)methyl)-[1,1'-biphenyl]-4-yl)-2-methyl-1H-benzo[d]imidazole-4-carboxylic acid; |
| 133. | 6-(2'-(((3-(dimethylamino)propyl)amino)methyl)-[1,1'-biphenyl]-4-yl)-2-methyl-1H-benzo[d]imidazole-4-carboxylic acid.2,2,2-trifluoroacetic acid; |
| 134. | 6-(2-(2,5-dimethyl-1H-pyrrol-1-yl)phenyl)-2-methyl-1H-benzo[d]imidazole-4-carboxylic acid; |
| 135. | 2-methyl-6-(3'-(((2,2,2-trifluoroethyl)amino)methyl)-[1,1'-biphenyl]-4-yl)-1H-benzo[d]imidazole-4-carboxylic acid.2,2,2-trifluoroacetic acid; |
| 136. | 2-methyl-6-(3'-(((3,3,3-trifluoropropyl)amino)methyl)-[1,1'-biphenyl]-4-yl)-1H-benzo[d]imidazole-4-carboxylic acid.2,2,2-trifluoroacetic acid; |
| 137. | 6-(3'-((1,1-dioxidothiomorpholino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 138. | 6-(4-(3,5-dimethyl-1H-pyrazol-1-yl)phenyl)-2-methyl-1H-benzo[d]imidazole-4-carboxylic acid.2,2,2-trifluoroacetic acid; |
| 139. | 2-methyl-6-(4-(3-methyl-1H-pyrazol-1-yl)phenyl)-1H-benzo[d]imidazole-4-carboxylic acid.2,2,2-trifluoroacetic acid; |
| 140. | 6-(2'-((diisobutylamino)methyl)-[1,1'-biphenyl]-4-yl)-2-methyl-1H-benzo[d]imidazole-4-carboxylic acid; |
| 141. | 2-methyl-6-(2'-(((2-(piperidin-1-yl)ethyl)amino)methyl)-[1,1'-biphenyl]-4-yl)-1H-benzo[d]imidazole-4-carboxylic acid; |
| 142. | 2-methyl-6-(2'-(((3,3,3-trifluoropropyl)amino)methyl)-[1,1'-biphenyl]-4-yl)-1H-benzo[d]imidazole-4-carboxylic acid; |
| 143. | (E)-6-(3'-((ethoxyimino)methyl)-[1,1'-biphenyl]-4-yl)-2-methyl-1H-benzo[d]imidazole-4-carboxylic acid.2,2,2-trifluoroacetic acid; |
| 144. | 6-(4-(4,5-dimethyloxazol-2-yl)phenyl)-2-methyl-1H-benzo[d]imidazole-4-carboxylic acid.2,2,2-trifluoroacetic acid; |
| 145. | 6-(2',6'-dimethyl-[1,1'-biphenyl]-4-yl)-2-methyl-1H-benzo[d]imidazole-4-carboxylic acid; |
| 146. | 6-(4'-(((3-(dimethylamino)propyl)amino)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 147. | 2-methyl-6-(2,3,5,6-tetrafluoro-4-(morpholinomethyl)phenyl)-1H-benzo[d]imidazole-4-carboxylic acid.2,2,2-trifluoroacetic acid; |
| 148. | (R)-2-methyl-6-(2,3,5,6-tetrafluoro-3'-((3-fluoropyrrolidin-1-yl)methyl)-[1,1'-biphenyl]-4-yl)-1H-benzo[d]imidazole-4-carboxylic acid.2,2,2-trifluoroacetic acid; |
| 149. | (R)-2-methyl-6-(2,3,5,6-tetrafluoro-3'-((3-hydroxypyrrolidin-1-yl)methyl)-[1,1'-biphenyl]-4-yl)-1H-benzo[d]imidazole-4-carboxylic acid.2,2,2-trifluoroacetic acid; |
| 150. | 6-(2'-fluoro-6'-(pyrrolidin-1-ylmethyl)-[1,1'-biphenyl]-4-yl)-2-methyl-1H-benzo[d]imidazole-4-carboxylic acid.2,2,2-trifluoroacetic acid; |
| 151. | 6-(3-(2,5-dimethyl-1H-pyrrol-1-yl)phenyl)-2-methyl-1H-benzo[d]imidazole-4-carboxylic acid; |
| 152. | 2-methyl-6-(2'-(((3-morpholinopropyl)amino)methyl)-[1,1'-biphenyl]-4-yl)-1H-benzo[d]imidazole-4-carboxylic acid.2,2,2-trifluoroacetic acid; |
| 153. | 6-(2'-(((2-(dimethylamino)ethyl)(methyl)amino)methyl)-[1,1'-biphenyl]-4-yl)-2-methyl-1H-benzo[d]imidazole-4-carboxylic acid.2,2,2-trifluoroacetic acid; |
| 154. | 6-(2'-((3,3-difluoropiperidin-1-yl)methyl)-2,3,5,6-tetrafluoro-[1,1'-biphenyl]-4-yl)-2-methyl-1H-benzo[d]imidazole-4-carboxylic acid.2,2,2-trifluoroacetic acid; |
| 155. | 6-(3'-((cyclohexylamino)methyl)-2,3,5,6-tetrafluoro-[1,1'-biphenyl]-4-yl)-2-methyl-1H-benzo[d]imidazole-4-carboxylic acid.2,2,2-trifluoroacetic acid; and |
| 156. | 2-methyl-6-(2'-(((2-(methylsulfonyl)ethyl)amino)methyl)-[1,1'-biphenyl]-4-yl)-1H-benzo[d]imidazole-4-carboxylic acid.2,2,2-trifluoroacetic acid. |

11. A pharmaceutical composition comprising a therapeutically effective amount of a compound of formula (I) according to claim 1, or a pharmaceutically acceptable salt, solvate, tautomer, hydrate, stereoisomer and mixture of isomers, or N-oxide thereof, in admixture with at least one pharmaceutically acceptable carrier or excipient or mixtures thereof in all ratios.

12. The compound according to claim 1, wherein $R_2$ is an optionally substituted Het selected from pyrrole, pyrazole, pyridyl, and isoxazole; wherein the optional substituent, at each occurrence, is independently selected from one or more occurrences of $R_4$.

13. A method of treating a subject in need thereof, the method comprising administering to the subject a therapeutically effective amount of the compound of claim 1, or a pharmaceutically acceptable salt, solvate, tautomer, hydrate, stereoisomer and mixture of isomers, or N-oxide thereof, wherein the subject has leukemia.

14. A method of treating a subject in need thereof, the method comprising administering to the subject a therapeutically effective amount of the compound of claim 1, or a pharmaceutically acceptable salt, solvate, tautomer, hydrate, stereoisomer and mixture of isomers, or N-oxide thereof, wherein the subject has multiple sclerosis or rheumatoid arthritis.

15. A method of treating a subject in need thereof, the method comprising administering to the subject a therapeutically effective amount of the compound of claim 1, or a pharmaceutically acceptable salt, solvate, tautomer, hydrate, stereoisomer and mixture of isomers, or N-oxide thereof, wherein the subject has a dihydroorotate dehydrogenase mediated disease or disorder.

16. The method according to claim 15, wherein the dihydroorotate dehydrogenase mediated disease or disorder is an autoimmune disorder or condition associated with an overactive immune response.

* * * * *